(12) United States Patent
Statsyuk et al.

(10) Patent No.: US 10,590,462 B2
(45) Date of Patent: Mar. 17, 2020

(54) PROBES AND ASSAYS FOR MEASURING E3 LIGASE ACTIVITY

(71) Applicant: NORTHWESTERN UNIVERSITY, Evanston, IL (US)

(72) Inventors: Alexander V. Statsyuk, Evanston, IL (US); Sungjin Park, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 35 days.

(21) Appl. No.: 15/922,676

(22) Filed: Mar. 15, 2018

(65) Prior Publication Data
US 2018/0258462 A1 Sep. 13, 2018

Related U.S. Application Data

(62) Division of application No. 14/856,251, filed on Sep. 16, 2015, now Pat. No. 9,951,371.

(60) Provisional application No. 62/051,494, filed on Sep. 17, 2014.

(51) Int. Cl.
| | | |
|---|---|---|
| C12Q 1/25 | (2006.01) |
| C07K 14/47 | (2006.01) |
| G01N 33/542 | (2006.01) |
| C12N 9/00 | (2006.01) |
| C12N 9/10 | (2006.01) |

(52) U.S. Cl.
CPC .............. *C12Q 1/25* (2013.01); *C07K 14/47* (2013.01); *C12N 9/104* (2013.01); *C12N 9/93* (2013.01); *C12Y 603/02019* (2013.01); *G01N 33/542* (2013.01); *C07K 2319/95* (2013.01); *G01N 2333/9015* (2013.01); *G01N 2440/36* (2013.01); *G01N 2500/00* (2013.01)

(58) Field of Classification Search
None
See application file for complete search history.

(56) References Cited

U.S. PATENT DOCUMENTS

| 7,935,822 B2 | 5/2011 | Arden-Jacob et al. |
| 2003/0003486 A1 | 1/2003 | Sauer et al. |
| 2006/0179585 A1 | 8/2006 | Zilles et al. |
| 2008/0038768 A1 | 2/2008 | Filipuzzi |
| 2011/0172420 A1 | 7/2011 | Zilles et al. |
| 2011/0190486 A1 | 8/2011 | Zilles et al. |
| 2011/0223677 A1 | 9/2011 | Arden-Jacob et al. |
| 2016/0076074 A1 | 3/2016 | Statsyuk et al. |

FOREIGN PATENT DOCUMENTS

| WO | WO2000032787 A1 | 6/2000 |
| WO | WO2006060739 A2 | 6/2006 |
| WO | WO2011151826 A2 | 12/2011 |
| WO | WO2012139112 A1 | 10/2012 |
| WO | WO2016044451 | 3/2016 |

OTHER PUBLICATIONS

An et al., "Crosstalk between kinases and Nedd4 family ubiquitin ligases." Mol Biosyst. Jul. 2014;10(7):1643-57.
Andre et al., "WWP, a new amino acid motif present in single or multiple copies in various proteins including dystrophin and the SH3-binding Yes-associated protein YAP65." Biochem Biophys Res Commun. Dec. 15, 1994;205(2):1201-5.
Bernassola et al., "The HECT family of E3 ubiquitin ligases: multiple players in cancer development." Cancer Cell. Jul. 8, 2008;14(1):10-21.
Borodovsky et al., "Chemistry-based functional proteomics reveals novel members of the deubiquitinating enzyme family." Chem Biol. Oct. 2002;9(10):1149-59.
Dawson et al., "Synthesis of native proteins by chemical ligation." Annu Rev Biochem. 2000;69:923-60.
Dawson et al., "Synthesis of proteins by native chemical ligation." Science. Nov. 4, 1994;266(5186):776-9.
Deshaies et al., "Ring domain E3 ubiquitin ligases." Annu Rev Biochem. 2009;78:399-434.
Ellison et al., "Epitope-tagged ubiquitin. A new probe for analyzing ubiquitin function." J Biol Chem. Nov. 5, 1991;266(31):21150-7.
Ernst et al., "A strategy for modulation of enzymes in the ubiquitin system." Science. Feb. 1, 2013;339(6119):590-5.
Fang et al., "The potential role of ubiquitin c-terminal hydrolases in oncogenesis." Biochim Biophys Acta. Aug. 2010;1806(1):1-6.
Gates et al., "Rapid formal hydrolysis of peptide-αthioesters." Chem Commun (Camb). Jan. 28, 2013;49(8):786-8.
Haugland et al.,Molecular Probes Handbook of Fluorescent Probes and Research Chemicals (10th ed.), Sep. 2005. TOC Only, 3 pages, Applicants will provide specific passages upon Examiner request.
Hershko et al., "The ubiquitin system." Annu Rev Biochem. 1998;67:425-79.
Hochstrasser, "Lingering mysteries of ubiquitin-chain assembly." Cell. Jan. 13, 2006;124(1):27-34.
Huibregtse et al., "A family of proteins structurally and functionally related to the E6-AP ubiquitin-protein ligase." Proc Natl Acad Sci U S A. Mar. 28, 1995;92(7):2563-7.
Hurst-Kennedy et al., "Ubiquitin C-terminal hydrolase L1 in tumorigenesis." Biochem Res Int. 2012;2012:123706.
Kamadurai et al., "Insights into ubiquitin transfer cascades from a structure of a UbcH5B approximately ubiquitin-HECT(NEDD4L) complex." Mol Cell. Dec. 25, 2009;36(6):1095-102.
Kamadurai et al., Mechanism of ubiquitin ligation and lysine prioritization by a HECT E3' eLife 2013, 2:e00828.
Kee et al., "The deubiquitinating enzyme Ubp2 modulates Rsp5-dependent Lys63-linked polyubiquitin conjugates in *Saccharomyces cerevisiae*." J Biol Chem. Dec. 1, 2006;281(48):36724-31.

(Continued)

*Primary Examiner* — Anand U Desai
(74) *Attorney, Agent, or Firm* — Casimir Jones S.C.; Thomas Isenbarger

(57) ABSTRACT

Provided herein is technology relating to the biological process of protein ubiquitination and particularly, but not exclusively, to compositions and methods for studying protein ubiquitination and developing therapeutics to modulate protein ubiquitination.

14 Claims, 74 Drawing Sheets

Specification includes a Sequence Listing.

(56) References Cited

OTHER PUBLICATIONS

Kee et al., "The Rsp5 ubiquitin ligase is coupled to and antagonized by the Ubp2 deubiquitinating enzyme." EMBO J. Jul. 6, 2005;24(13):2414-24.
Kim et al., "Polyubiquitination by HECT E3s and the determinants of chain type specificity." Mol Cell Biol. Jun. 2009;29(12):3307-18.
Kleiger et al., "Perilous journey: a tour of the ubiquitin-proteasome system." Trends Cell Biol. Jun. 2014;24(6):352-9.
Larsen et al., Substrate specificity of deubiquitinating enzymes: ubiquitin C-terminal hydrolases. Biochemistry. Mar. 10, 1998;37(10):3358-68.
Lorenz et al., "Macromolecular juggling by ubiquitylation enzymes." BMC Biol. Jun. 25, 2013;11:65.
Love et al., "Ubiquitin C-terminal electrophiles are activity-based probes for identification and mechanistic study of ubiquitin conjugating machinery." ACS Chem Biol. Apr. 17, 2009;4(4):275-87.
Lydeard et al., "Building and remodelling Cullin-Ring E3 ubiquitin ligases." EMBO Rep. Dec. 2013;14(12):1050-61.
Maher, "The effects of stress and aging on glutathione metabolism." Ageing Res Rev. May 2005;4(2):288-314.
Maspero et al., "Structure of a ubiquitin-loaded HECT ligase reveals the molecular basis for catalytic priming." Nat Struct Mol Biol. Jun. 2013;20(6):696-701.
Maspero et al., "Structure of the HECT:ubiquitin complex and its role in ubiquitin chain elongation." EMBO Rep. Apr. 2011;12(4):342-9.
Park et al., "Mechanism-based small molecule cross-linkers of HECT E3 ubiquitin ligase-substrate pairs." Biochemistry. Oct. 23, 2012;51(42):8327-9.
Pickart, "Mechanisms underlying ubiquitination." Annu Rev Biochem. 2001;70:503-33.
Pickart et al., "Substrate properties of site-specific mutant ubiquitin protein (G76A) reveal unexpected mechanistic features of ubiquitin-activating enzyme (E1)." J Biol Chem. Mar. 11, 1994;269(10):7115-23.
Pickart et al., "Ubiquitin carboxyl-terminal hydrolase acts on ubiquitin carboxyl-terminal amides." J Biol Chem. Jul. 5, 1985;260(13):7903-10.
Pines, "Cubism and the cell cycle: the many faces of the APC/C." Nat Rev Mol Cell Biol. Jun. 2, 2011;12(7):427-38.
Ronchi et al., "The active form of E6-associated protein (E6AP)/UBE3A ubiquitin ligase is an oligomer." J Biol Chem. Jan. 10, 2014;289(2):1033-48.
Rose et al., "An enzyme with ubiquitin carboxy-terminal esterase activity from reticulocytes." Biochemistry. Aug. 30, 1983;22(18):4234-7.
Rotin et al., "Physiological functions of the HECT family of ubiquitin ligases." Nat Rev Mol Cell Biol. Jun. 2009;10(6):398-409.
Saeki et al., "Lysine 63-linked polyubiquitin chain may serve as a targeting signal for the 26S proteasome." EMBO J. Feb. 18, 2009;28(4):359-71.
Saeki et al., "Preparation of ubiquitinated substrates by the PY motif-insertion method for monitoring 26S proteasome activity." Methods Enzymol. 2005;399:215-27.
Salvat et al., "The -4 phenylalanine is required for substrate ubiquitination catalyzed by HECT ubiquitin ligases." J Biol Chem. Apr. 30, 2004;279(18):18935-43.
Scheffner et al., "Mammalian HECT ubiquitin-protein ligases: biological and pathophysiological aspects." Biochim Biophys Acta. Jan. 2014;1843(1):61-74.
Scheffner et al., "Protein ubiquitination involving an E1-E2-E3 enzyme ubiquitin thioester cascade." Nature. Jan. 5, 1995;373(6509):81-3.
Schwarz et al., "Characterization of human hect domain family members and their interaction with UbcH5 and UbcH7." J Biol Chem. May 15, 1998;273(20):12148-54.
Setsuie et al., "The functions of UCH-L1 and its relation to neurodegenerative diseases." Neurochem Int. Jul.-Sep. 2007;51(2-4):105-11.
Staub et al., "WW domains." Structure. May 15, 1996;4(5):495-9.
Varshavsky, "The ubiquitin system, an immense realm." Annu Rev Biochem. 2012;81:167-76.
Verdecia et al., "Conformational flexibility underlies ubiquitin ligation mediated by the WWP1 HECT domain E3 ligase." Mol Cell. Jan. 2003;11(1):249-59.
Vijay-Kumar et al., "Three-dimensional structure of ubiquitin at 2.8 A resolution." Proc Natl Acad Sci U S A. Jun. 1985;82(11):3582-5.
Wang et al., "Functional domains of the Rsp5 ubiquitin-protein ligase." Mol Cell Biol. Jan. 1999;19(1):342-52.
Wilkinson et al., "Derivitization of the C-terminus of ubiquitin and ubiquitin-like proteins using intein chemistry: methods and uses." Methods Enzymol. 2005;399:37-51.
Zhang et al., "Recombinant expression, reconstitution and structure of human anaphase-promoting complex (APC/C)." Biochem J. Jan. 15, 2013;449(2):365-71.
Lenk et al., "Ubiquitin-mediated proteolysis of a short-lived regulatory protein depends on its cellular localization." J Biol Chem. Dec. 15, 2000;275(50):39403-10.

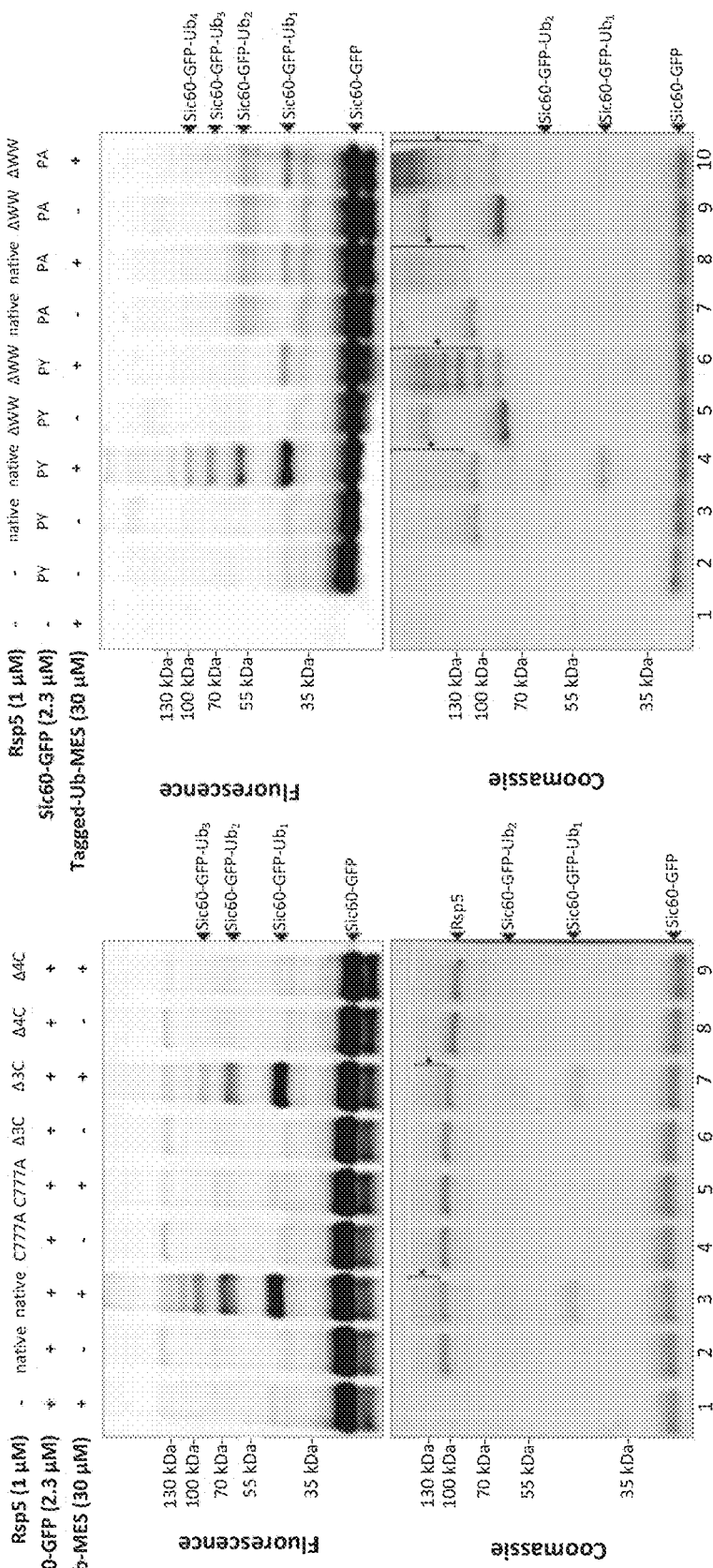

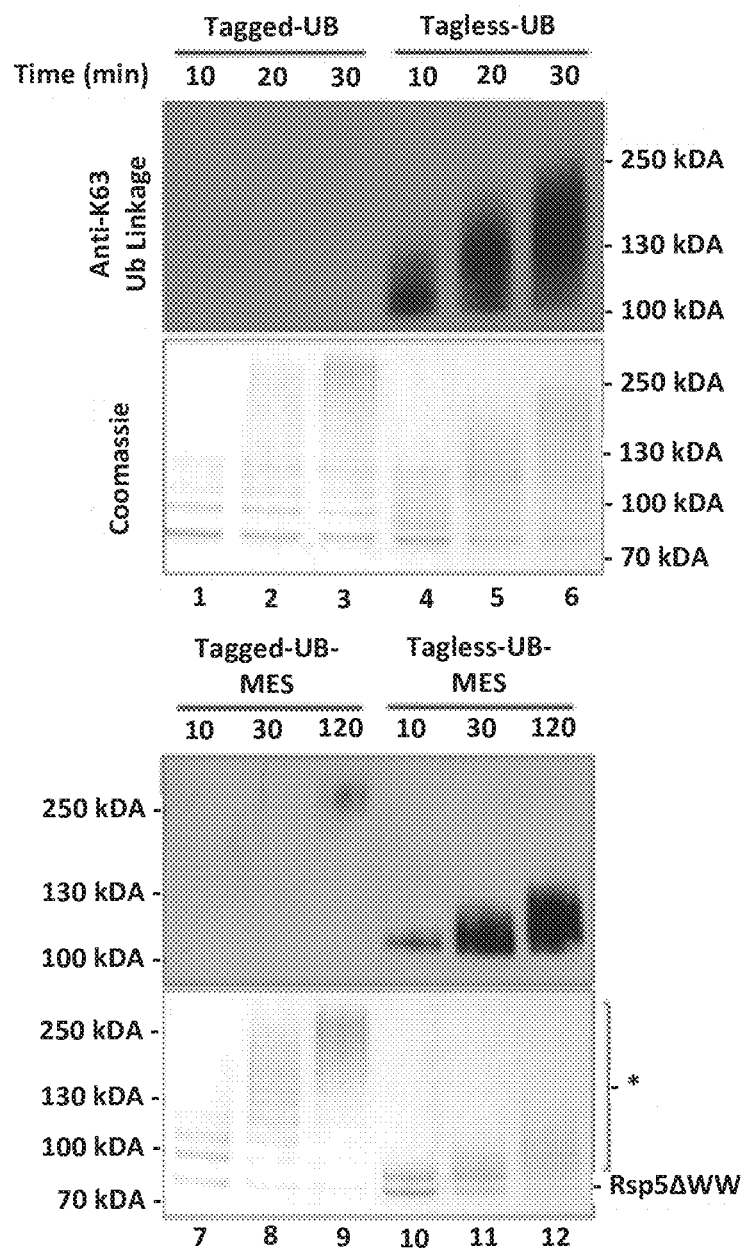

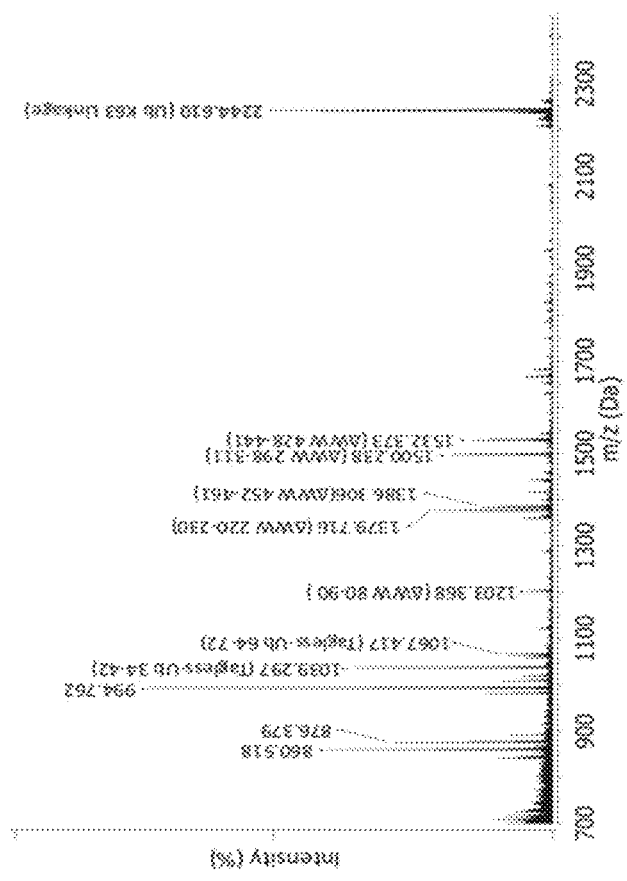
FIG. 5B  Tagged-Ub, Native cascade
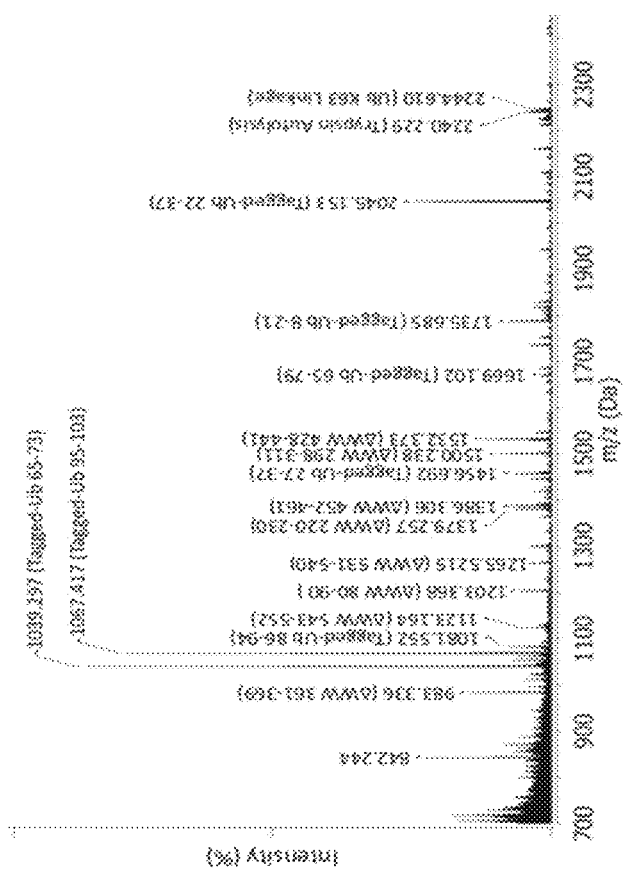
FIG. 5C  Tagless-Ub, Native cascade

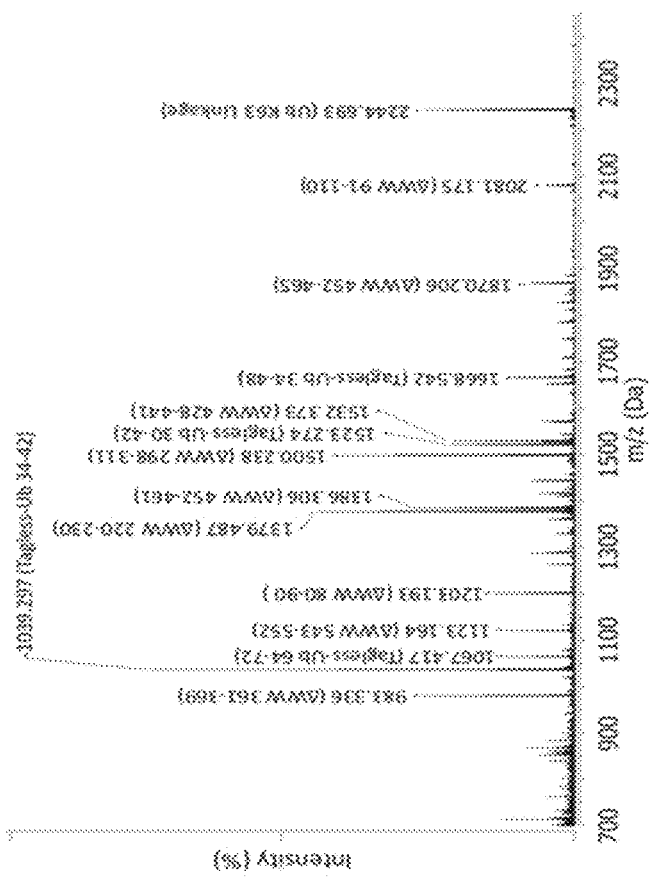
FIG.5D  Tagged-Ub-MES, ByS
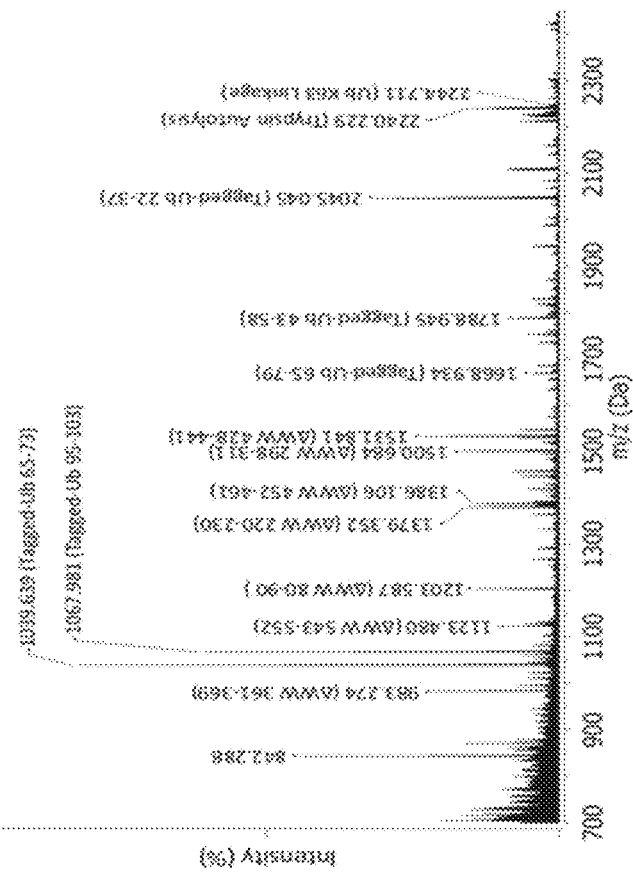
FIG.5E  Tagless-Ub-MES, ByS

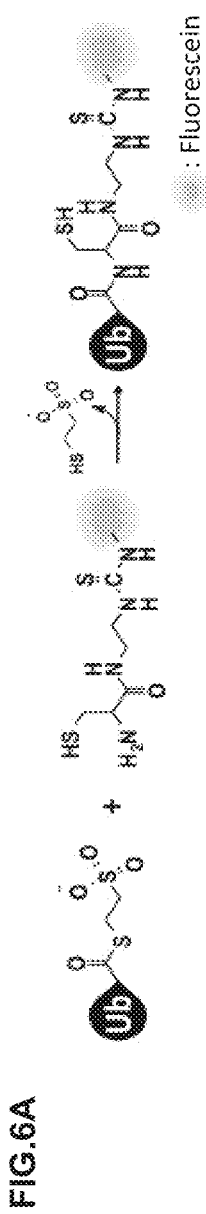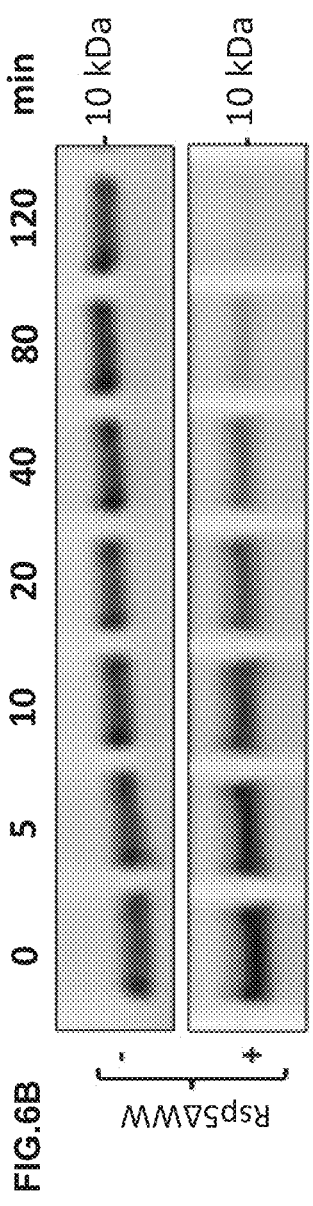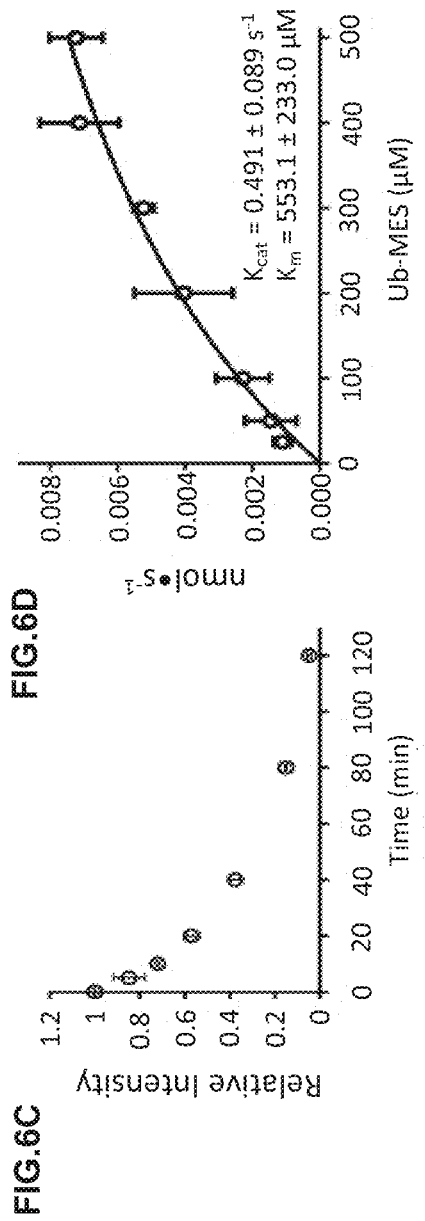
FIG. 6A
FIG. 6B
FIG. 6C
FIG. 6D

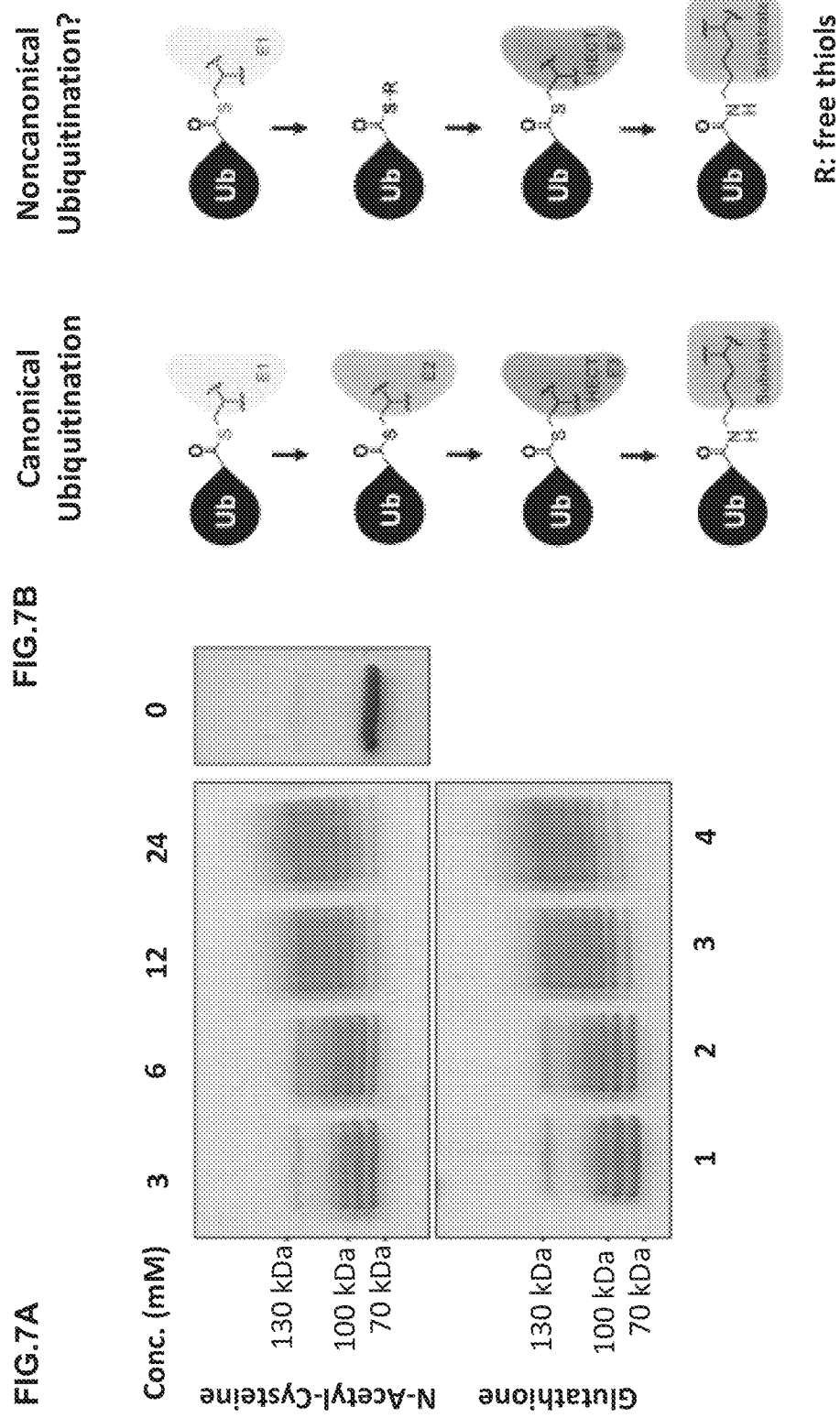

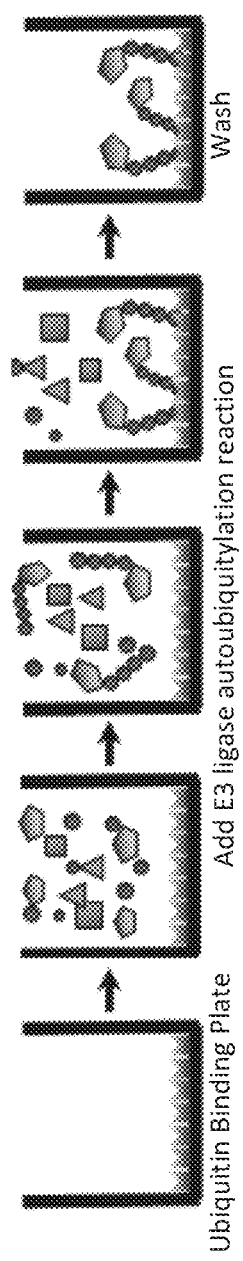
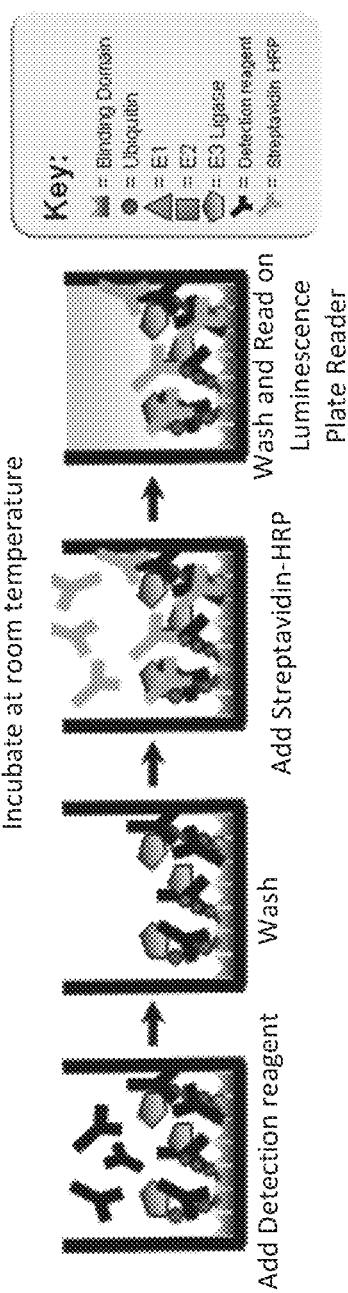
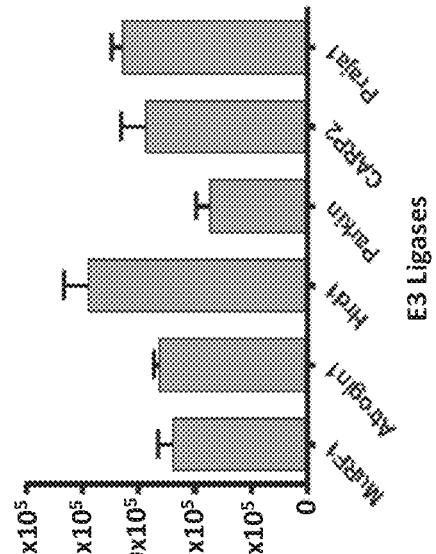
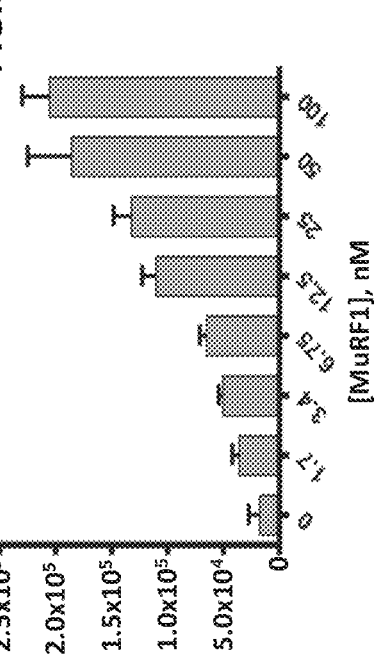
FIG. 8A
FIG. 8B
FIG. 8C

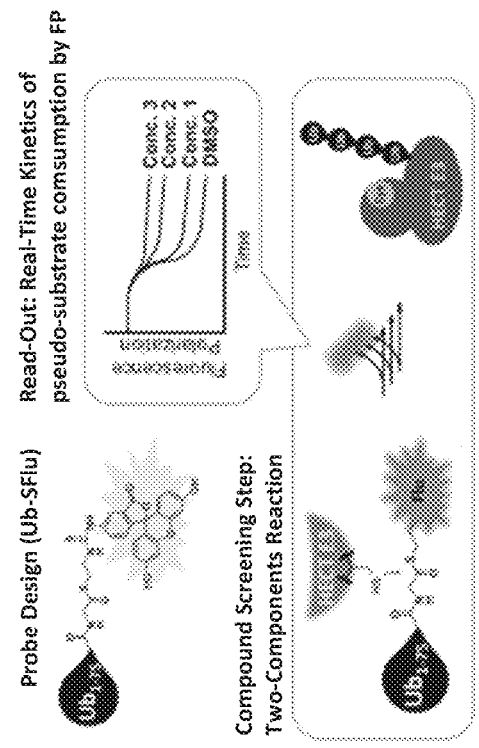
FIG.9A
FIG.9B
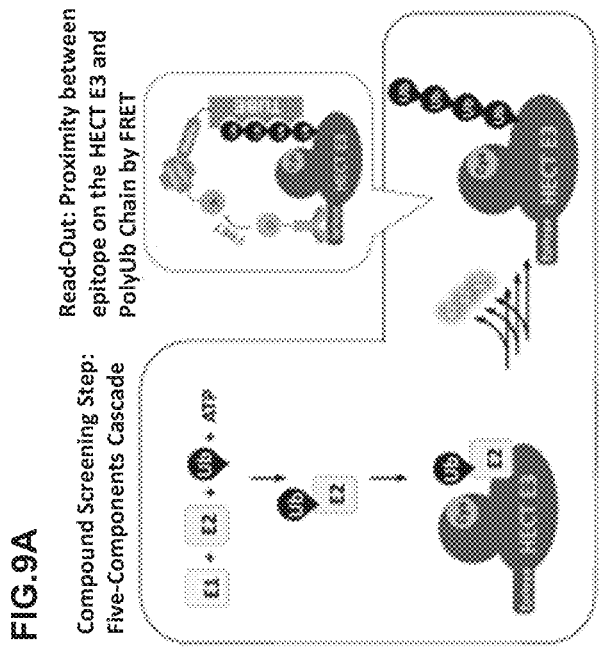
FIG.9C

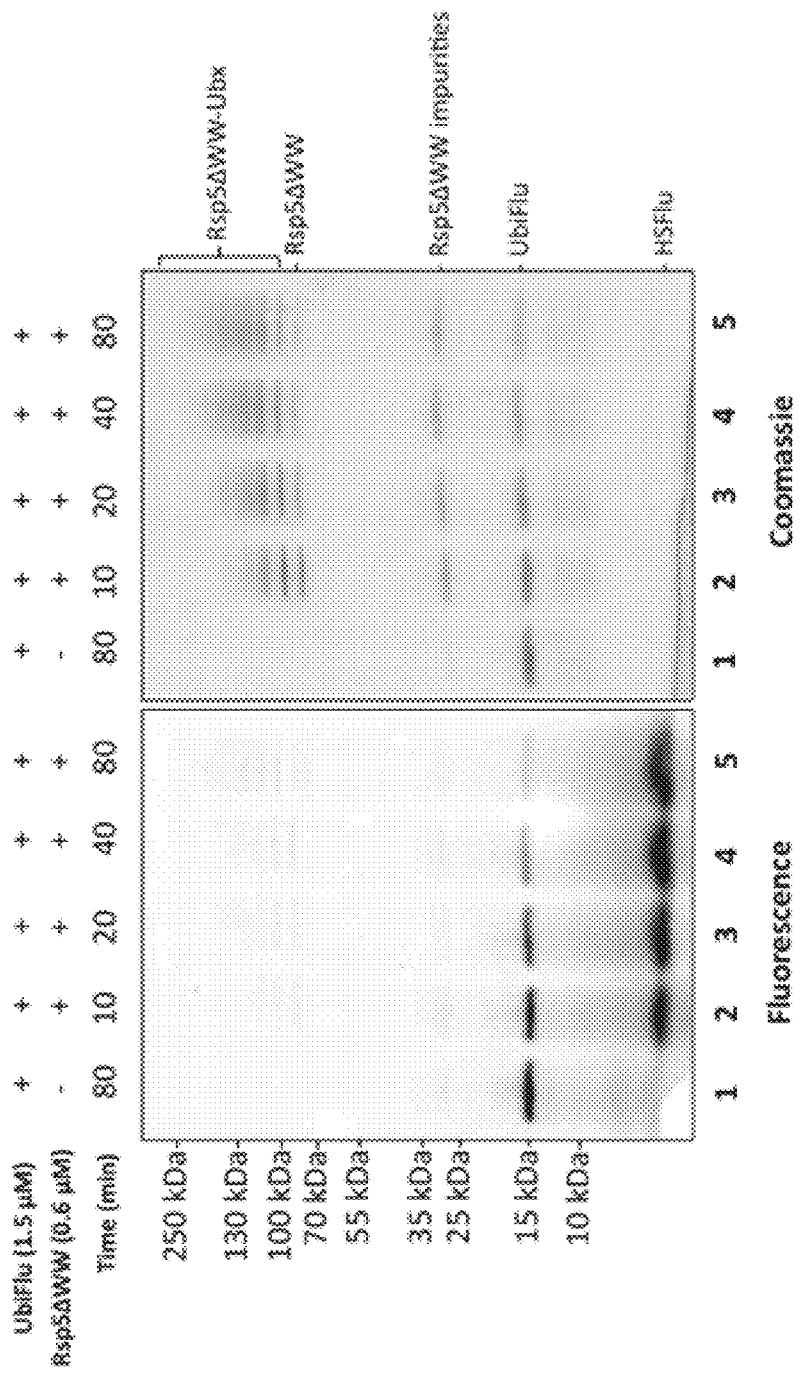

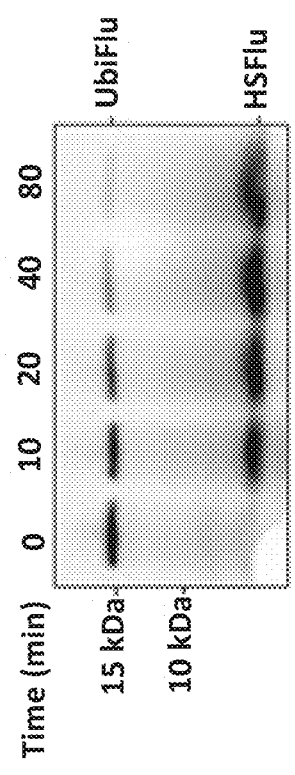
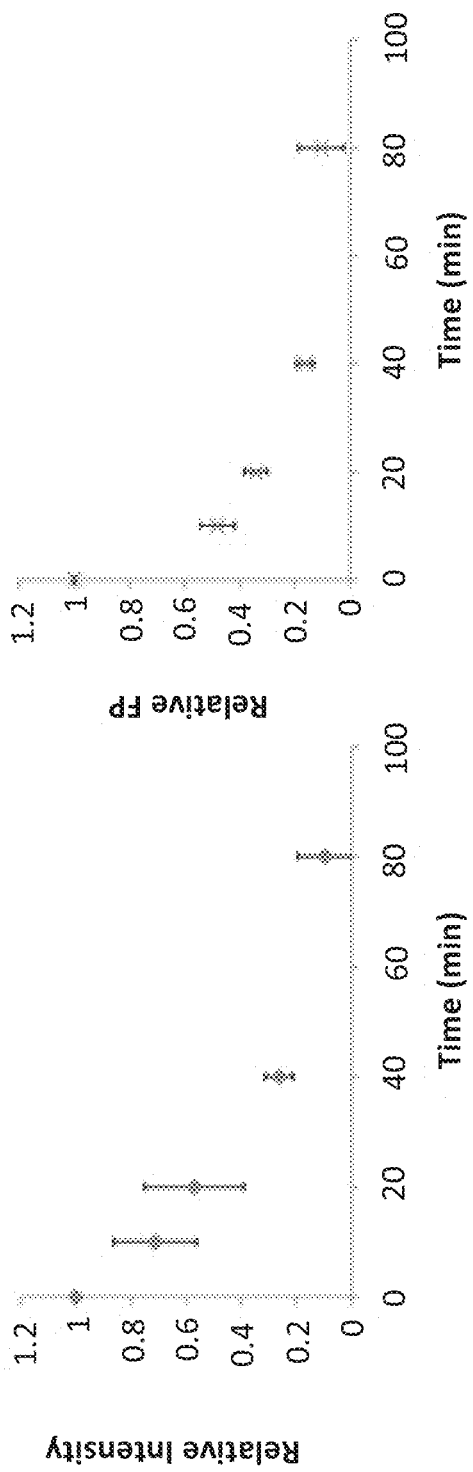
FIG. 11A
FIG. 11B
FIG. 11C

FIG. 17C Rsp5/ByS, Tagless Ub-MES
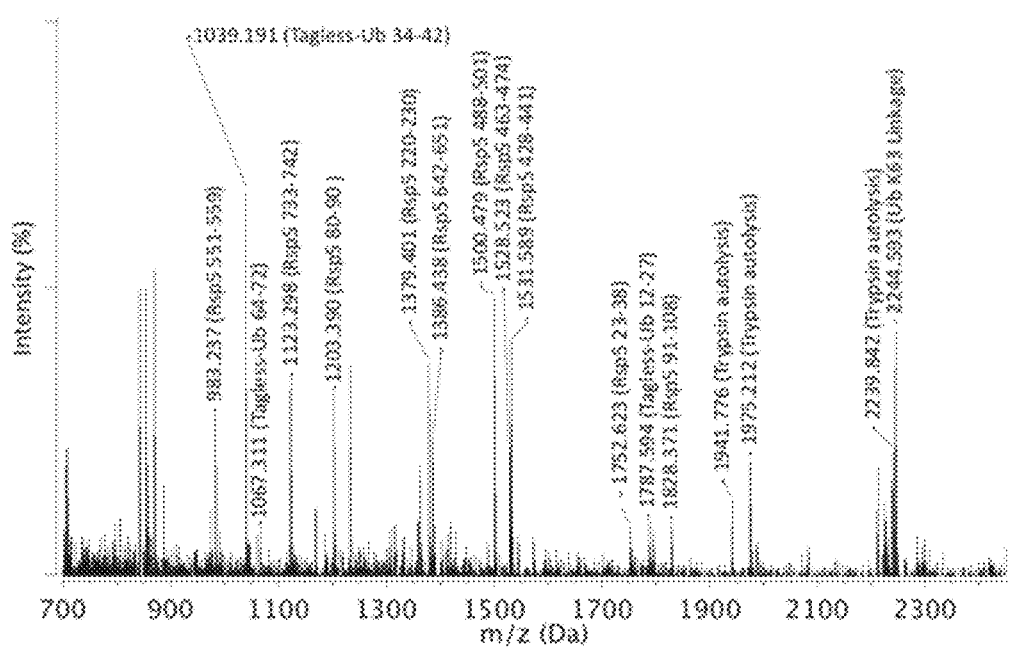
FIG. 17D Rsp5/ByS, Tagless Ub(K48R)-MES
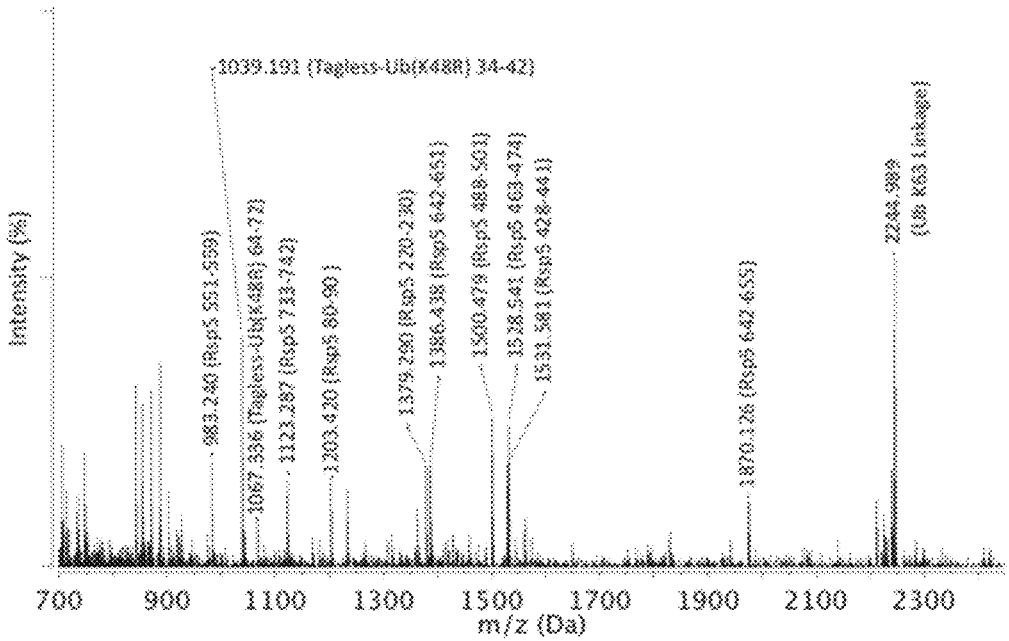

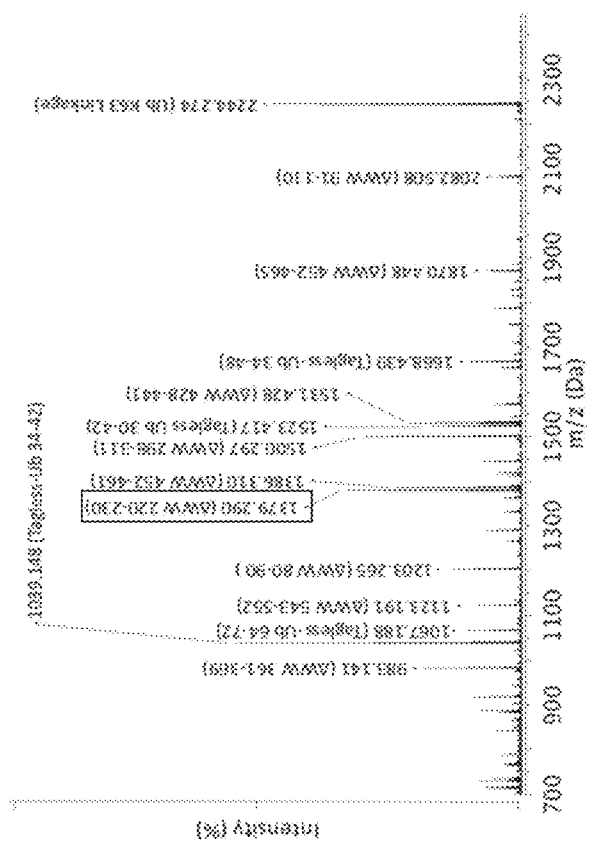
FIG.18B Rsp5ΔWW/ByS, Tagless-Ub-MES
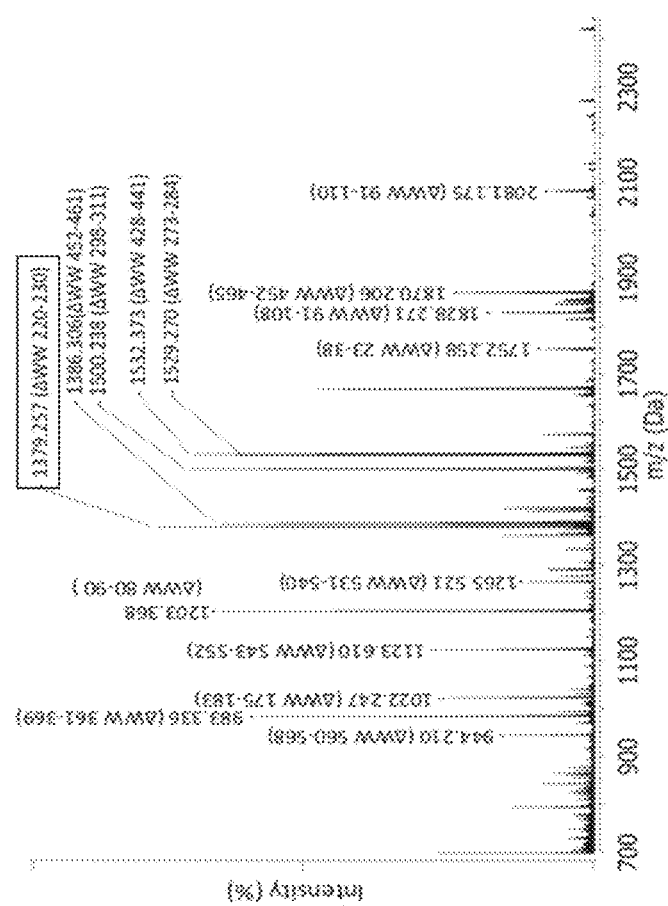
FIG.18A Rsp5ΔWW

Tagged-Ub(Met$^1$)-MES, ByS

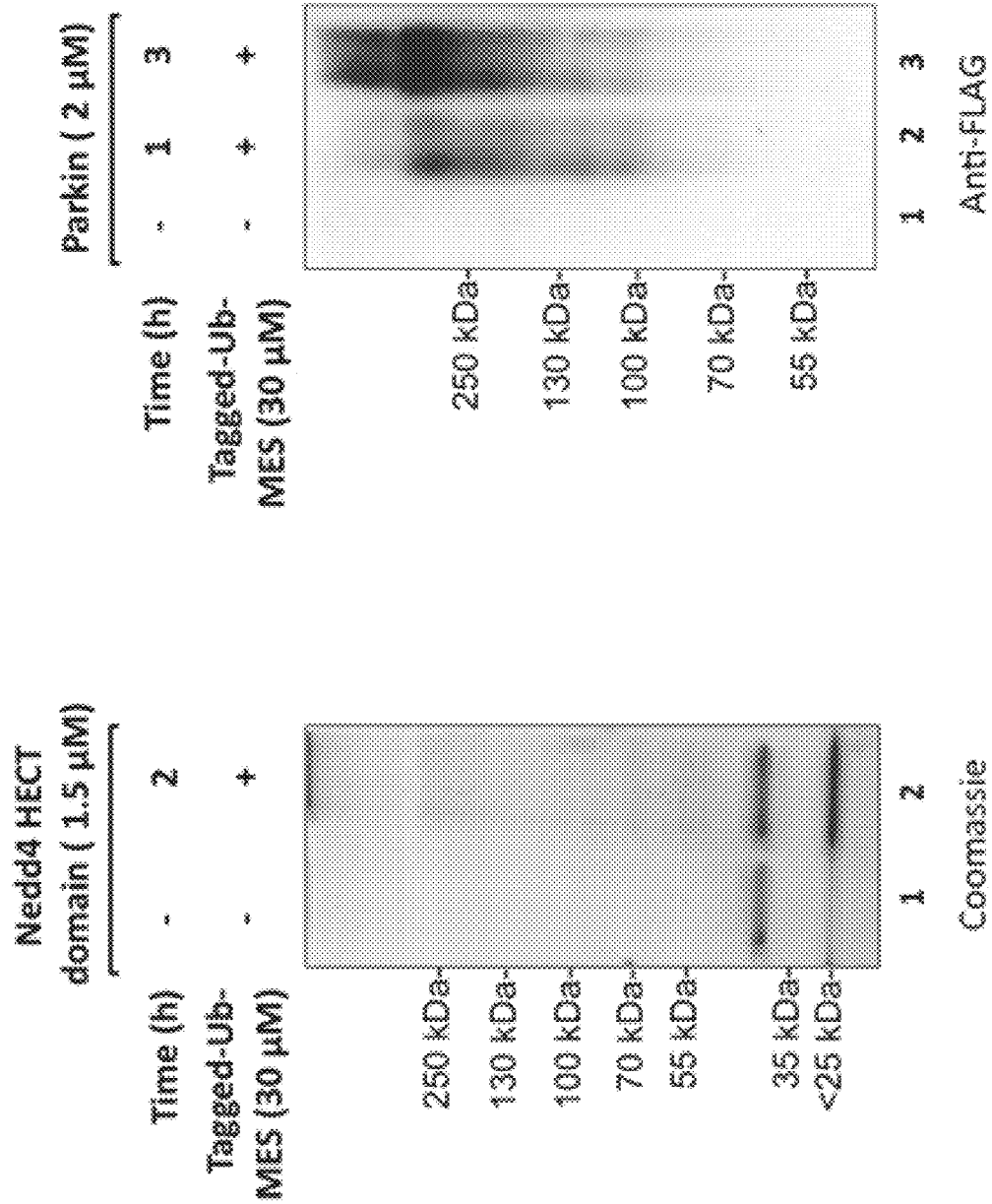

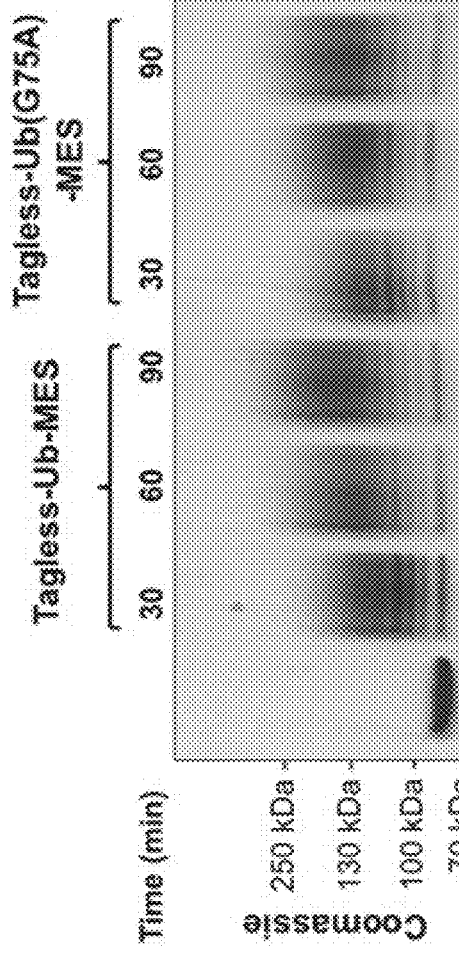
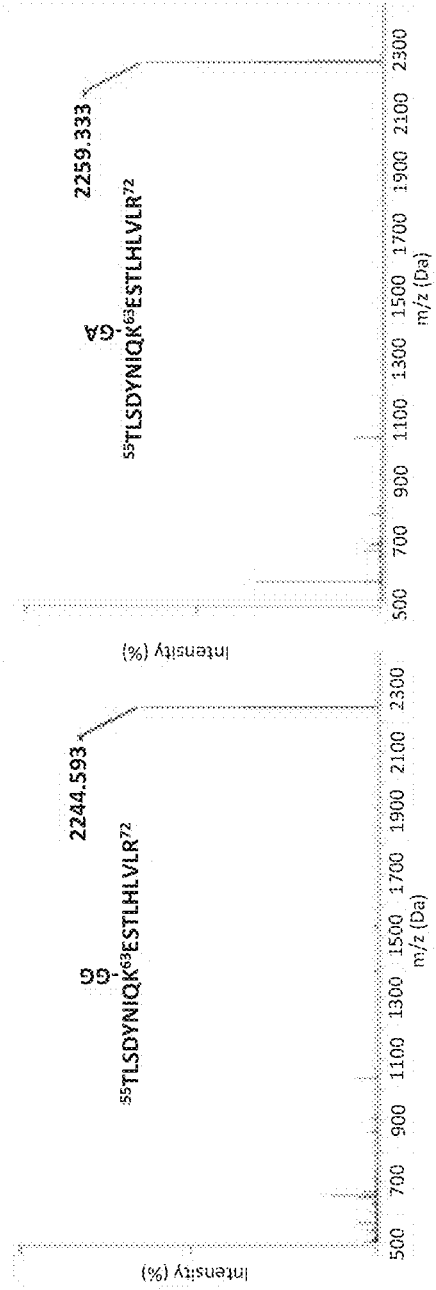
FIG. 26A
FIG. 26B
FIG. 26C

FIG. 27A

Amino acid sequence of hydrolyzed Tagged-Ub-MES (tag is marked with red color)

```
         10         20         30         40         50         60
MYEFDYKDHD GDYKDHDIDY KDDDDKHHHH HHQIFVKTLT GKTITLEVEP SDTIENVKAK
         70         80         90        100        107
IQDKEGIPPD QQRLIFAGKQ LEDGRTLSDY NIQKESTLHL VLRLRGG
```

Amino acid sequence of hydrolyzed Tagged-Ub(Met$^1$)-MES (Met$^1$ is inserted after the tag)

```
         10         20         30         40         50         60
MYEFDYKDHD GDYKDHDIDY KDDDDKHHHH HHM¹QIFVKTL TGKTITLEVE PSDTIENVKA
         70         80         90        100        108
KIQDKEGIPP DQQRLIFAGK QLEDGRTLSD YNIQKESTLH LVLRLRGG
```

Amino acid sequence of hydrolyzed Tagless-Ub-MES (wtUb)

```
         10         20         30         40         50         60
MQIFVKTLTG KTITLEVEPS DTIENVKAKI QDKEGIPPDQ QRLIFAGKQL EDGRTLSDYN
         70         76
IQKESTLHLV LRLRGG
```

Amino acid sequence of hydrolyzed Tagless-Ub(K48R)-MES

```
         10         20         30         40         50         60
MQIFVKTLTG KTITLEVEPS DTIENVKAKI QDKEGIPPDQ QRLIFAGKQL EDGRTLSDYN
         70         76
IQKESTLHLV LRLRGG
```

Amino acid sequence of hydrolyzed Tagless-Ub(K63R)-MES

```
         10         20         30         40         50         60
MQIFVKTLTG KTITLEVEPS DTIENVKAKI QDKEGIPPDQ QRLIFAGKQL EDGRTLSDYN
         70         76
IQKESTLHLV LRLRGG
```

Amino acid sequence of full length Rsp5 (three WW domains are marked with red color as annotated by UniProt P39940)

```
         10         20         30         40         50         60
MPSSISVKLV AAESLYKRDV FRSPDPFAVL TIDGYQTKST SAAKKTLNPY WNETFKFDDI
         70         80         90        100        110        120
NENSILTIQV FDQKKFKKKD QGFLGVVNVR VGDVLGHLDE DTATSSGRPR EETITRDLKK
        130        140        150        160        170        180
SNDGMAVSGR LIVVLSKLPS SSPHSQAPSG HTASSSTNTS STTRTNGHST SSTRNHSTSH
        190        200        210        220        230        240
PSRGTAQAVE STLQSGTTAA TNTATTSHRS TNSTSSATRQ YSSFEDQYGR LPPGWERRTD
        250        260        270        280        290        300
NFGRTYYVDH NTRTTTWKRP TLDQTEAERG NQLNANTELE RRQHRGRTLP GGSSDNSSVT
```

FIG. 27A continued

|  | 310 | 320 | 330 | 340 | 350 | 360 |
|---|---|---|---|---|---|---|
|  | VQVGGGSNIP | PVNGAAAAAF | AATGGTTSGL | GELPSGWEQR | FTPEGRAYFV | DHNTRTTTWV |
|  | 370 | 380 | 390 | 400 | 410 | 420 |
|  | DPRRQQYIRT | YGPTNTTIQQ | QPVSQLGPLP | SGWEMRLTNT | ARVYFVDHNT | KTTTWDDPRL |
|  | 430 | 440 | 450 | 460 | 470 | 480 |
|  | PSSLDQNVPQ | YKRDFRRKVI | YFRSQPALRI | LPGQCHIKVR | RKNIFEDAYQ | EIMRQTPEDL |
|  | 490 | 500 | 510 | 520 | 530 | 540 |
|  | KKRLMIKFDG | EEGLDYGGVS | REFFFLLSHE | MFNPFYCLFE | YSAYDNYTIQ | INPNSGINPE |
|  | 550 | 560 | 570 | 580 | 590 | 600 |
|  | HLNYFKFIGR | VVGLGVFHRR | FLDAFFVGAL | YKMMLRKKVV | LQDMEGVDAE | VYNSLNWMLE |
|  | 610 | 620 | 630 | 640 | 650 | 660 |
|  | NSIDGVLDLT | FSADDERFGE | VVTVDLKPDG | RNIEVTDGNK | KEYVELYTQW | RIVDRVQEQF |
|  | 670 | 680 | 690 | 700 | 710 | 720 |
|  | KAFMDGFNEL | IPEDLVTVFD | ERELELLIGG | IAEIDIEDWK | KHTDYRGYQE | SDEVIQWFWK |
|  | 730 | 740 | 750 | 760 | 770 | 780 |
|  | CVSEWDNEQR | ARLLQFTTGT | SRIPVNGFKD | LQGSDGPRRF | TIEKAGEVQQ | LPKSHTCFNR |
|  | 790 | 800 | 809 |  |  |  |
|  | VDLPQYVDYD | SMKQKLTLAV | EETIGFGQE |  |  |  |

Amino acid sequence of Rsp5ΔWW (amino acids 231-420 of full length Rsp5 were deleted to remove all three WW domains.)

|  | 10 | 20 | 30 | 40 | 50 | 60 |
|---|---|---|---|---|---|---|
|  | MPSSISVKLV | AAESLYKRDV | FRSPDPFAVL | TIDGYQTKST | SAAKKTLNPY | WNETFKFDDI |
|  | 70 | 80 | 90 | 100 | 110 | 120 |
|  | NENSILTIQV | FDQKKFKKKD | QGFLGVVNVR | VGDVLGHLDE | DTATSSGRPR | EETITRDLKK |
|  | 130 | 140 | 150 | 160 | 170 | 180 |
|  | SNDGMAVSGR | LIVVLSKLPS | SSPHSQAPSG | HTASSSTNTS | STTRTNGHST | SSTRNHSTSH |
|  | 190 | 200 | 210 | 220 | 230 | 240 |
|  | PSRGTAQAVE | STLQSGTTAA | TNTATTSHRS | TNSTSSATRQ | YSSFEDQYGR | PSSLDQNVPQ |
|  | 250 | 260 | 270 | 280 | 290 | 300 |
|  | YKRDFRRKVI | YFRSQPALRI | LPGQCHIKVR | RKDIFEDAYQ | EIMRQTPEDL | KKRLMIKFDG |
|  | 310 | 320 | 330 | 340 | 350 | 360 |
|  | EEGLDYGGVS | REFFFLLSHE | MSNPFYCLFE | YSAYDNYTIQ | INPNSGINPE | HLNYFKFIGR |
|  | 370 | 380 | 390 | 400 | 410 | 420 |
|  | VVGLGVFHRR | FLDAFFVGAL | YKMMLRKKVV | LQDMEGVDAE | VYNSLNWMLE | NSIDGVLDLT |
|  | 430 | 440 | 450 | 460 | 470 | 480 |
|  | FSADDERFGE | VVTVDLKPDG | RNIEVTDGNK | KEYVELYTQW | RIVDRVQEQF | KAFMDGFNEL |
|  | 490 | 500 | 510 | 520 | 530 | 540 |
|  | IPEDLVTVFD | ERELELLIGG | IAEIDIEDWK | KHTDYRGYQE | SDEVIQWFWK | CVSEWDNEQR |
|  | 550 | 560 | 570 | 580 | 590 | 600 |
|  | ARLLQFTTGT | SRIPVNGFKD | LQGSDGPRRF | TIEKAGEVQQ | LPKSHTCFNR | VDLPQYVDYD |
|  | 610 | 619 |  |  |  |  |
|  | SMKQKLTLAV | EETIGFGQE |  |  |  |  |

FIG. 27B

| # | Average MW | Position | Peptide Sequence |
|---|---|---|---|
| 1 | 5516.5383 | 502-546 | EFFFLLSHEMFNPFYCLFEYSAYDNYTIQINPNSGINPEH LNYFK |
| 2 | 4955.4041 | 288-340 | TLPGGSSDNSSVTVQVGGGSNIPPVNGAAAAAFAATGGTTSGLGELPSGWEQR |
| 3 | 4402.0377 | 579-617 | VVLQDMEGVDAEVYNSLNWMLENSIDGVLDLTFSADDER |
| 4 | 2986.4727 | 370-396 | TYGPTNTTIQQQPVSQLGPL PSGWEMR |
| 5 | 2670.2350 | 138-164 | LPSSSPHSQAPSGHTASSST NTSSTTR |
| 6 | 2562.2390 | 184-209 | GTAQAVESTLQSGTTAATNT ATTSHR |
| 7 | 2457.1642 | 662-682 | AFMDGFNELIPEDLVTVFDE R |
| 8 | 2139.0604 | 57-74 | FDDINENSILTIQVFDQK |
| 9 | 2082.0257 | 91-110 | VGDVLGHLDEDTATSSGRPR |
| 10 | 2056.0848 | 683-700 | ELELLIGGIAEIDIEDWK |
| 11 | 1869.9512 | 642-655 | EYVELYTQWRIVDR |
| 12 | 1828.8671 | 91-108 | VGDVLGHLDEDTATSSGR |
| 13 | 1814.8384 | 707-720 | GYQESDEVIQWFWK |
| 14 | 1751.8850 | 23-38 | SPDPFAVLTIDGYQTK |
| 15 | 1572.7250 | 781-793 | VDLPQYVDYDSMK |
| 16 | 1531.8123 | 428-441 | FGEVVTVVDLKPDGR |
| 17 | 1528.7100 | 463-474 | NIFEDAYQEIMR |
| 18 | 1506.7686 | 796-809 | LTLAVEETIGFGQE |
| 19 | 1500.6601 | 488-501 | FDGEEGLDYGGVSR |
| 20 | 1488.7693 | 420-432 | LPSSLDQNVPQYK |
| 21 | 1412.6845 | 46-56 | TLNPYWNETFK |
| 22 | 1390.7405 | 561-572 | FLDAFFVGALYK |
| 23 | 1386.6688 | 642-651 | EYVELYTQWR |
| 24 | 1379.5862 | 220-230 | QYSSFEDQYGR |
| 25 | 1358.6659 | 270-281 | GNQLNANTELER |
| 26 | 1265.5215 | 721-730 | CVSEWDNEQR |
| 27 | 1203.6480 | 80-90 | DQGFLGVVNVR |
| 28 | 1168.5381 | 245-253 | TYYVDHNTR |
| 29 | 1159.5589 | 260-269 | PTLDQTEAER |
| 30 | 1123.6106 | 733-742 | LLQFTTGTSR |
| 31 | 1122.5578 | 403-411 | VYFVDHNTK |
| 32 | 1122.5327 | 347-355 | AYFVDHNTR |
| 33 | 1106.6092 | 618-627 | FGEVVTVDLK |
| 34 | 1047.4814 | 165-174 | TNGHSTSSTR |
| 35 | 1022.4762 | 175-183 | NHSTSHPSR |
| 36 | 1011.4701 | 210-219 | STNSTSSATR |
| 37 | 1008.5659 | 450-458 | ILPGQCHIK |
| 38 | 993.5615 | 9-17 | LVAAESLYK |
| 39 | 993.4418 | 121-130 | SNDGMAVSGR |
| 40 | 991.4479 | 412-419 | TTTWDDPR |
| 41 | 989.4898 | 632-640 | NIEVTDGNK |
| 42 | 983.5785 | 551-559 | VVGLGVFHR |

FIG. 27B continued

| 43 | 975.4894 | 356-363 | TTTWVDPR |
|---|---|---|---|
| 44 | 969.5363 | 765-773 | AGEVQQLPK |
| 45 | 944.4432 | 750-758 | DLQGSDGPR |
| 46 | 864.3781 | 774-780 | SHTCFNR |
| 47 | 854.4519 | 231-237 | LPPGWER |
| 48 | 848.4546 | 1-8 | MPSSISVK |
| 49 | 830.4254 | 475-481 | QTPEDLK |
| 50 | 778.4094 | 656-661 | VQEQFK |
| 51 | 774.4508 | 743-749 | IPVNGFK |
| 52 | 771.5338 | 131-137 | LIVVLSK |
| 53 | 748.3835 | 111-116 | EETITR |
| 54 | 709.3264 | 239-244 | TDNFGR |
| 55 | 707.3835 | 365-369 | QQYIR |
| 56 | 706.3518 | 341-346 | FTPEGR |
| 57 | 697.4031 | 439-443 | VIYFR |
| 58 | 691.3158 | 702-706 | HTDYR |
| 59 | 675.3784 | 397-402 | LTNTAR |
| 60 | 671.3835 | 444-449 | SQPALR |
| 61 | 637.3555 | 760-764 | FTIEK |
| 62 | 636.3351 | 254-258 | TTTWK |
| 63 | 564.2987 | 39-44 | STSAAK |
| 64 | 550.2840 | 573-576 | MMLR |
| 65 | 536.2827 | 19-22 | DVFR |
| 66 | 504.3214 | 484-487 | LMIK |
| 67 | 502.2983 | 652-655 | IVDR |

FIG. 27C

| # | Average MW | Position | Peptide Sequence |
|---|---|---|---|
| 1 | 5456.5019 | 312-356 | EFFFLLSHEMSNPFYCLFEY SAYDNYTIQINPNSGINPEH LNYFK |
| 2 | 4402.0377 | 389-427 | VVLQDMEGVDAEVYNSLNWM LENSIDGVLDLTFSADDER |
| 3 | 2670.2350 | 138-164 | LPSSSPHSQAPSGHTASSST NTSSTTR |
| 4 | 2562.2390 | 184-209 | GTAQAVESTLQSGTTAATNT ATTSHR |
| 5 | 2457.1642 | 472-492 | AFMDGFNELIPEDLVTVFDE R |
| 6 | 2139.0604 | 57-74 | FDDINENSILTIQVFDQK |
| 7 | 2082.0201 | 91-110 | VGDVLGHLDEDTATSSGRPR |
| 8 | 2056.0848 | 493-510 | ELELLIGGIAEIDIEDWK |
| 9 | 1869.9512 | 452-465 | EYVELYTQWRIVDR |
| 10 | 1828.8671 | 91-108 | VGDVLGHLDEDTATSSGR |
| 11 | 1814.8384 | 517-530 | GYQESDEVIQWFWK |
| 12 | 1751.8850 | 23-38 | SPDPFAVLTIDGYQTK |
| 13 | 1660.937 | 254-268 | SQPALRILPGQCHIK |
| 14 | 1572.7250 | 591-603 | VDLPQYVDYDSMK |
| 15 | 1531.8182 | 428-441 | FGEVVTVDLKPDGR |
| 16 | 1529.6940 | 273-284 | DIFEDAYQEIMR |
| 17 | 1506.7686 | 606-619 | LTLAVEETIGFGQE |
| 18 | 1500.6601 | 298-311 | FDGEEGLDYGGVSR |
| 19 | 1412.6845 | 46-56 | TLNPYWNETFK |
| 20 | 1390.7405 | 371-382 | FLDAFFVGALYK |
| 21 | 1386.6688 | 452-461 | EYVELYTQWR |
| 22 | 1379.5862 | 220-230 | QYSSFEDQYGR |
| 23 | 1375.6852 | 231-242 | PSSLDQNVPQYK |
| 24 | 1265.5215 | 531-540 | CVSEWDNEQR |
| 25 | 1203.6480 | 80-90 | DQGFLGVVNVR |
| 26 | 1123.6106 | 543-552 | LLQFTTGTSR |
| 27 | 1106.6092 | 428-437 | FGEVVTVDLK |
| 28 | 1047.4814 | 165-174 | TNGHSTSSTR |
| 29 | 1022.4762 | 175-183 | NHSTSHPSR |
| 30 | 1011.4701 | 210-219 | STNSTSSATR |
| 31 | 1008.5659 | 260-268 | ILPGQCHIK |
| 32 | 993.5615 | 9-17 | LVAAESLYK |
| 33 | 993.4418 | 121-130 | SNDGMAVSGR |
| 34 | 989.4898 | 442-450 | NIEVTDGNK |
| 35 | 983.5785 | 361-369 | VVGLGVFHR |
| 36 | 969.5363 | 575-583 | AGEVQQLPK |
| 37 | 944.4432 | 560-568 | DLQGSDGPR |
| 38 | 864.3781 | 584-590 | SHTCFNR |
| 39 | 848.4546 | 1-8 | MPSSISVK |
| 40 | 830.4254 | 285-291 | QTPEDLK |
| 41 | 778.4094 | 466-471 | VQEQFK |
| 42 | 774.4508 | 553-559 | IPVNGFK |

FIG. 27C continued

| 43 | 771.5338 | 131-137 | LIVVLSK |
|---|---|---|---|
| 44 | 748.3835 | 111-116 | EETITR |
| 45 | 697.4031 | 249-253 | VIYFR |
| 46 | 691.3158 | 512-516 | HTDYR |
| 47 | 671.3835 | 254-259 | SQPALR |
| 48 | 637.3555 | 570-574 | FTIEK |
| 49 | 564.2987 | 39-44 | STSAAK |
| 50 | 550.2840 | 383-386 | MMLR |
| 51 | 536.2827 | 19-22 | DVFR |
| 52 | 504.3214 | 294-297 | LMIK |
| 53 | 502.2983 | 462-465 | IVDR |

FIG. 28A

| # | Average MW | Peptide Sequence |
|---|---|---|
| 1 | 1787.9273 | $^{12}$TITLEVEPSDTIENVK$^{27}$ |
| 2 | 1668.9126 | $^{34}$EGIPPDQQRLIFAGK$^{48}$ |
| 3 | 1523.7812 | $^{30}$IQDKEGIPPDQQR$^{42}$ |
| 4 | 1081.5524 | $^{55}$TLSDYNIQK$^{63}$ |
| 5 | 1067.6207 | $^{64}$ESTLHLVLR$^{72}$ |
| 6 | 1039.5167 | $^{34}$EGIPPDQQR$^{42}$ |
| 7 | 765.4327 | $^{1}$MQIFVK$^{6}$ |
| 8 | 717.3526 | $^{49}$QLEDGR$^{54}$ |
| 9 | 648.4079 | $^{43}$LIFAGK$^{48}$ |
| 10 | 519.3137 | $^{7}$TLTGK$^{11}$ |
| 11 | 503.2824 | $^{30}$IQDK$^{33}$ |

FIG. 28B

| Linkage | Average MW | Peptide Sequence |
|---|---|---|
| K6 | 1379.6765 | $^1$MQIFVK(GG)TLTGK$^{11}$ |
| K11 | 2402.6741 | $^7$TLTGK(GG)TITLEVEPSDTIENVK$^{27}$ |
| K27 | 2101.3325 | $^{12}$TITLEVEPSDTIENVK(GG)AK$^{29}$ |
| K29 | 815.9224 | $^{28}$AK(GG)IQDK$^{33}$ |
| K33 | 1637.7653 | $^{30}$IQDK(GG)EGIPPDQQR$^{42}$ |
| K48 | 1460.6488 | $^{43}$LIFAGK(GG)QLEDGR$^{54}$ |
| K63 | 2244.5259 | $^{55}$TLSDYNIQK(GG)ESTLHLVLR$^{72}$ |

FIG. 29A

| # | Average MW | Peptide Sequence |
|---|---|---|
| 1 | 1787.9273 | $^{12}$TITLEVEPSDTIENVK$^{27}$ |
| 2 | 1081.5524 | $^{55}$TLSDYNIQK$^{63}$ |
| 3 | 1067.6207 | $^{64}$ESTLHLVLR$^{72}$ |
| 4 | 1039.5167 | $^{34}$EGIPPDQQR$^{42}$ |
| 5 | 765.4327 | $^{1}$MQIFVK$^{6}$ |
| 6 | 717.3526 | $^{49}$QLEDGR$^{54}$ |
| 7 | 676.4140 | $^{43}$LIFAGR$^{48}$ |
| 8 | 519.3137 | $^{7}$TLTGK$^{11}$ |
| 9 | 503.2824 | $^{30}$IQDK$^{33}$ |

FIG. 29B

| Linkage | Average MW | Peptide Sequence |
|---|---|---|
| K6 | 1379.6765 | $^{1}$MQIFVK(GG)TLTGK$^{11}$ |
| K11 | 2402.6741 | $^{7}$TLTGK(GG)TITLEVEPSDTIENVK$^{27}$ |
| K27 | 2101.3325 | $^{12}$TITLEVEPSDTIENVK(GG)AK$^{29}$ |
| K29 | 815.9224 | $^{28}$AK(GG)IQDK$^{33}$ |
| K33 | 1637.7653 | $^{30}$IQDK(GG)EGIPPDQQR$^{42}$ |
| K63 | 2244.5259 | $^{55}$TLSDYNIQK(GG)ESTLHLVLR$^{72}$ |

FIG. 30A

| # | Average MW | Peptide Sequence |
|---|---|---|
| 1 | 1787.9273 | $^{12}$TITLEVEPSDTIENVK$^{27}$ |
| 2 | 1668.9126 | $^{34}$EGIPPDQQRLIFAGK$^{48}$ |
| 3 | 1109.5585 | $^{55}$TLSDYNIQR$^{63}$ |
| 4 | 1067.6207 | $^{64}$ESTLHLVLR$^{72}$ |
| 5 | 1039.5167 | $^{34}$EGIPPDQQR$^{42}$ |
| 6 | 765.4327 | $^{1}$MQIFVK$^{6}$ |
| 7 | 717.3526 | $^{49}$QLEDGR$^{54}$ |
| 8 | 648.4079 | $^{43}$LIFAGK$^{48}$ |
| 9 | 519.3137 | $^{7}$TLTGK$^{11}$ |
| 10 | 503.2824 | $^{30}$IQDK$^{33}$ |

FIG. 30B

| Linkage | Average MW | Peptide Sequence |
|---|---|---|
| K6 | 1379.6765 | $^{1}$MQIFVK(GG)TLTGK$^{11}$ |
| K11 | 2402.6741 | $^{7}$TLTGK(GG)TITLEVEPSDTIENVK$^{27}$ |
| K27 | 2101.3325 | $^{12}$TITLEVEPSDTIENVK(GG)AK$^{29}$ |
| K29 | 815.9224 | $^{28}$AK(GG)IQDK$^{33}$ |
| K33 | 1637.7653 | $^{30}$IQDK(GG)EGIPPDQQR$^{42}$ |
| K48 | 1460.6488 | $^{43}$LIFAGK(GG)QLEDGR$^{54}$ |

FIG. 31

| # | Average MW w/o Acetylation | Average MW w/ Acetylation | Protein | Peptide Sequence |
|---|---|---|---|---|
| 1 | 983.5785 | 1026.6235 | Rsp5ΔWW | $^{361}$VVGLGVFHR$^{369}$ |
| 2 | 1123.6106 | 1166.6556 | Rsp5ΔWW | $^{543}$TLTGK(GG)TITLEVEPSDTIENVK$^{552}$ |
| 3 | 1203.6480 | 1246.693 | Rsp5ΔWW | $^{80}$DQGFLGVVNVR$^{90}$ |
| 4 | 1379.5862 | 1422.6312 | Rsp5ΔWW | $^{220}$QYSSFEDQYGR$^{230}$ |
| 5 | 1386.6688 | 1429.7138 | Rsp5ΔWW | $^{452}$EYVELYTQWR$^{461}$ |
| 6 | 1500.6601 | 1543.7051 | Rsp5ΔWW | $^{298}$FDGEEGLDYGGVSR$^{311}$ |
| 7 | 1039.5167 | 1081.5617 | Tagless-Ub | $^{34}$EGIPPDQQR$^{42}$ |
| 8 | 1067.6207 | 1109.6657 | Tagless-Ub | $^{64}$ESTLHLVLR$^{72}$ |

FIG. 32A

| # | Average MW | Peptide Sequence |
|---|---|---|
| 1 | 2044.9484 | $^{22}$DDDDKHHHHHHQIFVK$^{37}$ |
| 2 | 1787.9273 | $^{43}$TITLEVEPSDTIENVK$^{58}$ |
| 3 | 1735.7194 | $^{8}$DHDGDYKDHDIDYK$^{21}$ |
| 4 | 1668.9126 | $^{65}$EGIPPDQQRLIFAGK$^{79}$ |
| 5 | 1456.7457 | $^{27}$HHHHHHQIFVK$^{37}$ |
| 6 | 1081.5524 | $^{86}$TLSDYNIQK$^{94}$ |
| 7 | 1067.6207 | $^{95}$ESTLHLVLR$^{103}$ |
| 8 | 1039.5167 | $^{65}$EGIPPDQQR$^{73}$ |
| 9 | 995.4179 | $^{1}$MYEFDYK$^{7}$ |
| 10 | 905.3999 | $^{15}$DHDIDYK$^{21}$ |
| 11 | 849.3373 | $^{8}$DHDGDYK$^{14}$ |
| 12 | 717.3526 | $^{80}$QLEDGR$^{85}$ |
| 13 | 648.4079 | $^{74}$LIFAGK$^{79}$ |
| 14 | 607.2205 | $^{22}$DDDDK$^{26}$ |
| 15 | 519.3137 | $^{38}$TLTGK$^{42}$ |
| 16 | 503.2824 | $^{61}$IQDK$^{64}$ |

FIG. 32B

| Linkage | Average MW | Peptide Sequence |
|---|---|---|
| K6 | 2071.3289 | $^{27}$HHHHHHQIFVK(GG)TLTGK$^{42}$ |
| K11 | 2402.6741 | $^{86}$TLTGK(GG)TITLEVEPSDTIENVK$^{103}$ |
| K27 | 2101.3325 | $^{43}$TITLEVEPSDTIENVK(GG)AK$^{60}$ |
| K29 | 815.9224 | $^{59}$AK(GG)IQDK$^{64}$ |
| K33 | 1637.7653 | $^{30}$IQDK(GG)EGIPPDQQR$^{42}$ |
| K48 | 1460.6488 | $^{43}$LIFAGK(GG)QLEDGR$^{54}$ |
| K63 | 2244.5259 | $^{55}$TLSDYNIQK(GG)ESTLHLVLR$^{72}$ |
| Tag 1 | 1940.0227 | $^{1}$MYEFDYK(GG)DHDGDYK$^{14}$ |
| Tag 2 | 1849.8401 | $^{8}$DHDGDYK(GG)DHDIDYK$^{21}$ |
| Tag 3 | 1607.5603 | $^{15}$DHDIDYK(GG)DDDDK$^{26}$ |
| Tag 4 | 2159.2620 | $^{22}$DDDDK(GG)HHHHHHQIFVK$^{37}$ |

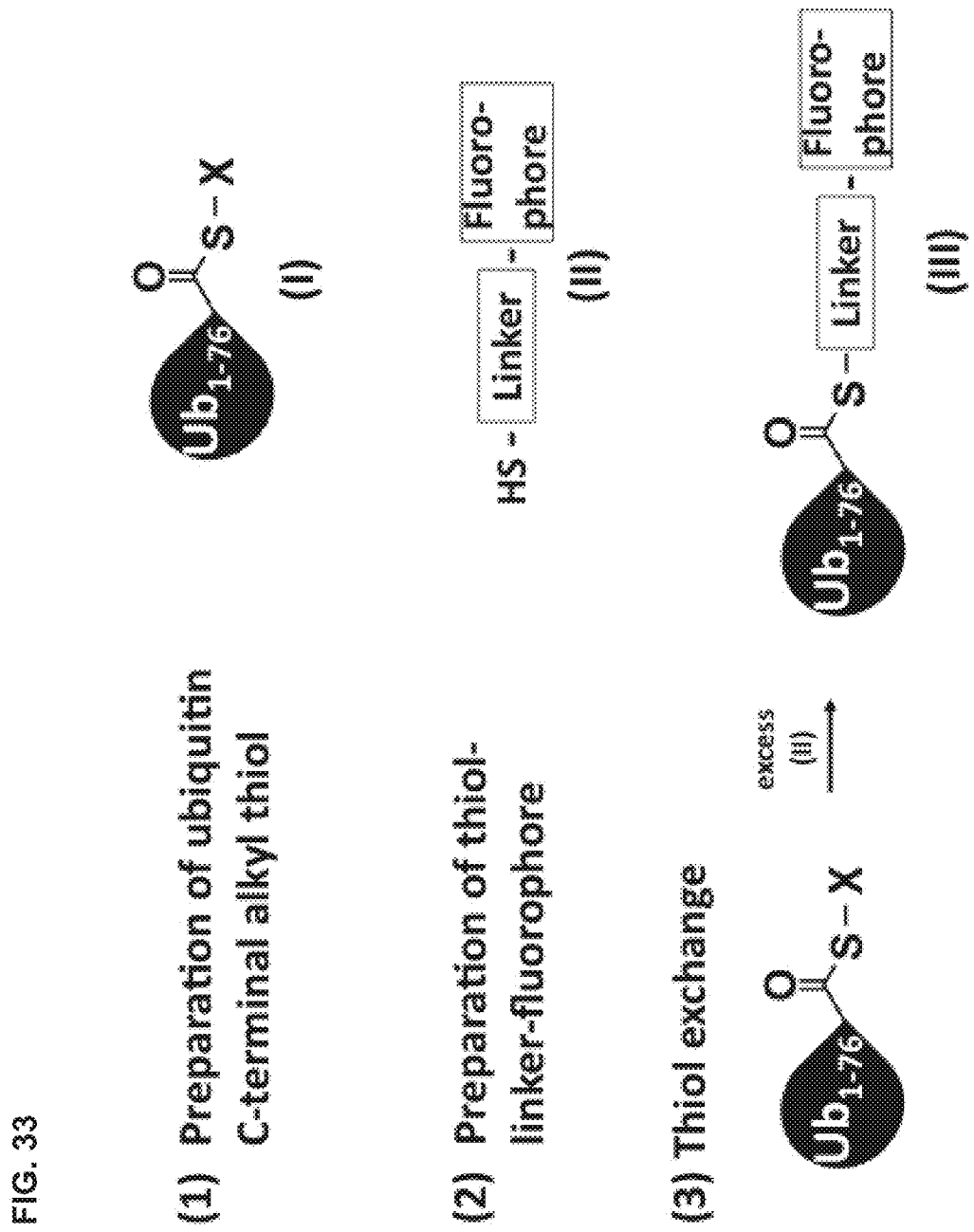

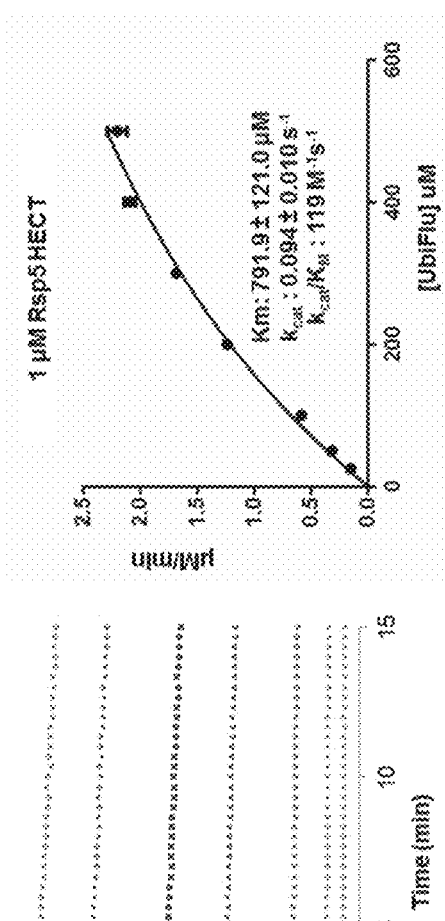
FIG. 36A
FIG. 36B
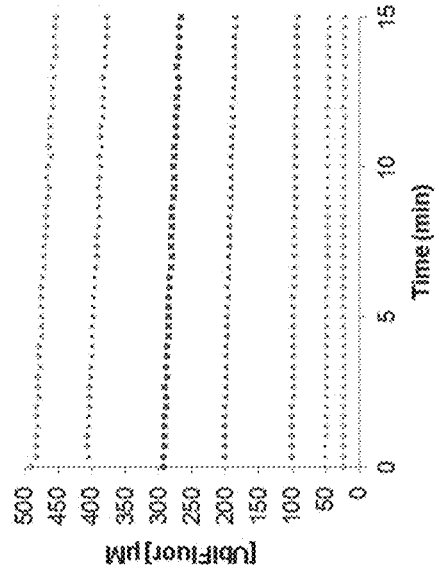
FIG. 36C
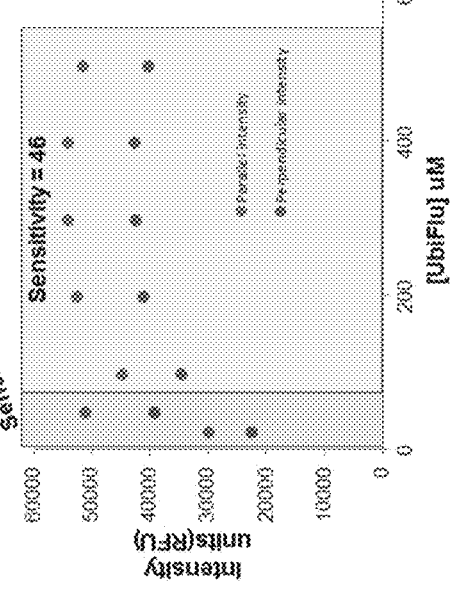
FIG. 36D

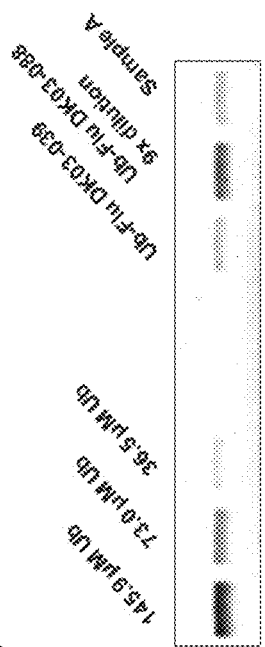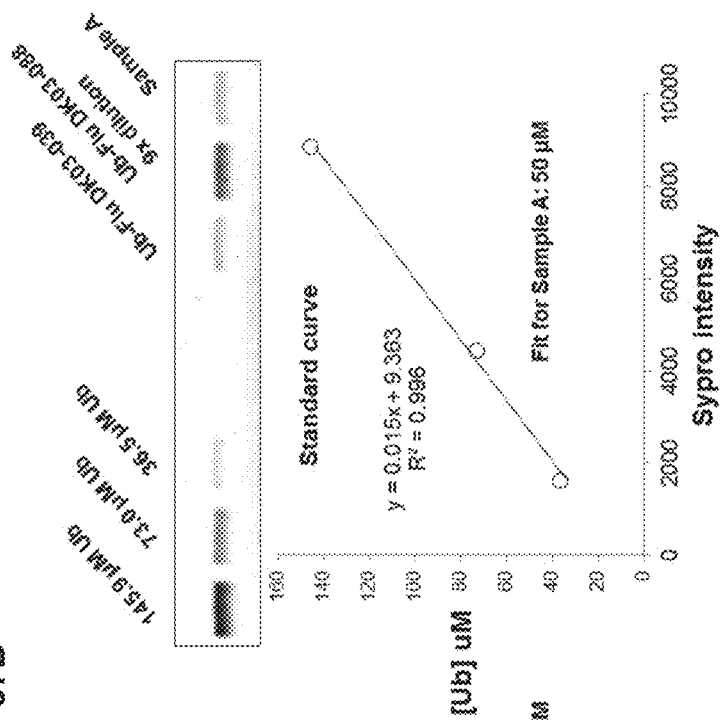
FIG. 37B
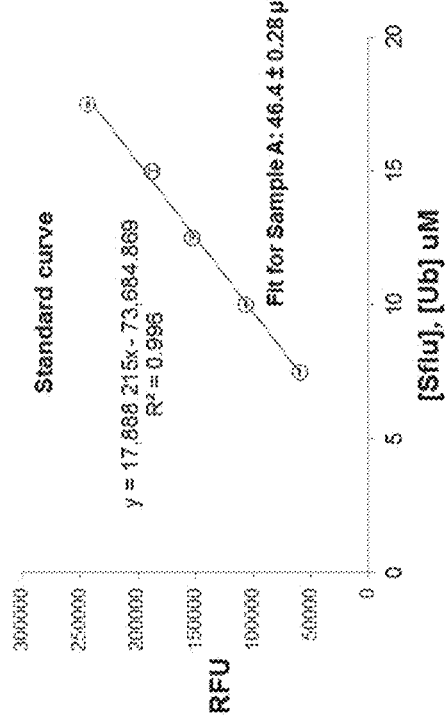
FIG. 37A

SEQUENCE LISTING

```
<160> NUMBER OF SEQ ID NOS: 1

<210> SEQ ID NO 1
<211> LENGTH: 76
<212> TYPE: PRT
<213> ORGANISM: Artificial sequence
<220> FEATURE:
<223> OTHER INFORMATION: Synthetic

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

PROBES AND ASSAYS FOR MEASURING E3 LIGASE ACTIVITY

This application is a divisional of U.S. application Ser. No. 14/856,251, filed Sep. 16, 2015, which claims priority to U.S. provisional patent application Ser. No. 62/051,494, filed Sep. 17, 2014. Each of which is incorporated herein by reference in its entirety.

FIELD

Provided herein is technology relating the biological process of protein ubiquitination and particularly, but not exclusively, to compositions and methods for studying protein ubiquitination and developing therapeutics to modulate protein ubiquitination.

BACKGROUND

Protein quitination is a highly conserved post-translational modification that regulates fundamental cellular processes.[1-3] Ubiquitin conjugation is controlled by the sequential action of three enzymes: ubiquitin activating enzyme 1 (E1, 2 known), ubiquitin conjugating enzyme 2 (E2, ~37 known), and ubiquitin ligase enzyme 3 (E3, ~600 known).[3] Among these, E3 enzymes stand out due to the astonishing complexity and diversity of biochemical reactions they catalyze. E3 enzymes control polyubiquitin chain linkages and polyubiquitin chain length, select specific substrates and specific residues to be ubiquitinated, as well as select and activate specific E2~Ub thioesters for subsequent ubiquitin transfer events.[4] Such complexity makes it difficult to study the biochemical properties of E3 enzymes, and to design assays to discover and to characterize pharmacological modulators of E3s. Typical biochemical assays to study E3 enzymes require at least three enzymes E1/E2/E3, ubiquitin, and ATP in the simplest case. The situation is more complex in the case of multi-subunit E3s such as cullin-RING E3s and APC/C E3, where up to 3-15 protein subunits are required to assemble the functional E3 enzyme.[5-7] As such, studying protein ubiquitination and developing therapeutics targeting protein ubiquitination are difficult due to the complexity of the E1→E2→E3 ubiquitination cascade.

SUMMARY

Provided herein is technology related to the surprising discovery that C-terminal ubiquitin thioesters can undergo a direct transthiolation reaction with the catalytic cysteine of the model HECT E3 ubiquitin ligase Rsp5 and form a catalytically active Rsp5~Ub thioester. This is achieved in the absence of the E1 and E2 enzymes and ATP. The resulting Rsp5~Ub thioester undergoes efficient autoubiquitination, ubiquitinates protein substrates, and synthesizes polyubiquitin chains with specific isopeptide linkages. Since the developed chemical system bypasses the need for ATP, and E1, and E2 enzymes, it is named "bypassing system" ("ByS"). Herein it is shown that the newly discovered bypassing system recapitulates the enzymatic mechanism of the native ubiquitination reaction. Importantly, the developed bypassing system provides the direct evidence that E2 enzymes are dispensable for the K-63 specific isopeptide bond formation between ubiquitin molecules by Rsp5 in vitro. It has been found that two other E3 enzymes, Nedd4-1 HECT E3 and RBR E3 Parkin, were also active under the ByS reaction conditions. In addition, it was discovered that small molecule thiols, such as glutathione can act as E2 enzyme mimics in the native E1→E2→E3 ubiquitination cascade, leading to the efficient E3 enzyme autoubiquitination. Therefore, the discovered ubiquitination cascade may occur under physiologically relevant conditions. The reported findings provide general mechanistic insights on protein ubiquitination, and offer new strategies for assay development to discover pharmacological modulators of E3 enzymes. Based on these discoveries, a novel fluorescent probe "UbFluor" (also referred to similar names such as the name "UbiFlu") has been developed, which is used to design fluorescent high throughput screening assays to find inhibitors or activators of E3 ligases with catalytic cysteines such as HECT E3s, RBR E3s, and NEL E3s.

Accordingly, provided herein are embodiments of technologies related to a composition comprising a ubiquitin C-terminal thioester fluorophore. For example, in some embodiments the ubiquitin C-terminal thioester fluorophore comprises a ubiquitin covalently attached to a fluorophore by a thioester. In some embodiments, the ubiquitin C-terminal thioester fluorophore comprises a ubiquitin covalently attached to a linker and a linker covalently attached to the fluorophore. The technology is not limited in the fluorophore that is used; e.g., in some embodiments the fluorophore is Fluorescein, Rhodamine, BODIPY, Alexa Fluor 488, Oregon Green 488, or Alexa Fluor 594, and other types of fluorescent molecules. The technology is not limited in the linker that is used; e.g., in some embodiments the linker is an alkyl, cycloalkyl, aryl, heteroaryl, heteroalkyl, cyclic heterocycle, polymer, carbon nanotube, quantum dot, or nanoparticle. In some embodiments, the ubiquitin comprises amino acids 1-76 of the protein ubiquitin polypeptide (SEQ ID NO: 1). Embodiments relate to using the ubiquitin C-terminal thioester fluorophore to measure the activity of an E3 ligase. Accordingly, in some embodiments compositions further comprise an E3 ligase, e.g., NEDD4, NEDD4L, ITCH, WWP1, WWP2, SMURF1, SMURF2, NEDL1, NEDL2, E6AP, HECTD2, KIAA0614, TRIP12, G2E3, EDD, HACE1, HECTD1, UBE3B, UBE3C, KIAA0317, HUWE1, HECTD3, HERC1, HERC2, HERC3, HERC4, HERC5, HERC6, SopA, NIeL, ARIH1, ARIH2, CUL9, ANKIB1, PARK2, RNF144A, RNF144B, RBCK1, RNF19A, RNF19B, RNF31, RNF216, RNF14, RNF217, SspH2, IpaH1.4, or Ipa3. In some embodiments, the composition finds use in testing and/or screening for molecular entities (e.g., small molecules, drugs, pharmaceuticals, etc.) that modulate (e.g., increase the activity of, decrease the activity of) E3 ligase. Accordingly, in some embodiments the compositions further comprise a modulator of E3 ligase. In some embodiments, the ubiquitin C-terminal thioester fluorophore reacts with the E3 ligase to release the fluorophore. Thus, in some embodiments the compositions further comprise free fluorophore and/or further comprise activated E3~Ub thioester.

In additional embodiments, the technology relates to a method of screening for modulators of E3 ligase activity, the method comprising providing a test composition comprising an E3 ligase, a ubiquitin C-terminal thioester fluorophore, and a molecule to test for the ability to modulate the activity of the E3 ligase; and monitoring the fluorescence (e.g., the fluorescence polarization) of the fluorophore in the test composition. Some embodiments further provide comparing the fluorescence polarization of the test composition to a control composition. Thus, in some embodiments the technology further comprises comparing the fluorescence (e.g., the fluorescence polarization) of the fluorophore in the test composition to the fluorescence (e.g., the fluorescence polarization) of a control composition comprising the E3 ligase and the ubiquitin C-terminal thioester fluorophore, but not comprising the molecule, to test for the ability to modulate the activity of the E3 ligase by the molecule. And, additionally, some embodiments further provide identifying the molecule to test as a molecule that modulates the activity of E3 ligase when the fluorescence (e.g., the fluorescence polarization) of the fluorophore in the test composition is different than the fluorescence (e.g., the fluorescence polarization) of the fluorophore in the control composition. In some particular embodiments, the technology finds use in testing the activity of an E3 ligase, e.g., an E3 ligase that is NEDD4, NEDD4L, ITCH, WWP1, WWP2, SMURF1, SMURF2, NEDL1, NEDL2, E6AP, HECTD2, KIAA0614, TRIP12, G2E3, EDD, HACE1, HECTD1, UBE3B, UBE3C, KIAA0317, HUWE1, HECTD3, HERC1, HERC2, HERC3, HERC4, HERC5, HERC6, SopA, NIeL, ARIH1, ARIH2, CUL9, ANKI1, PARK2, RNF144A, RNF144B, RBCK1, RNF19A, RNF19B, RNF31, RNF216, RNF14, RNF217, SspH2, IpaH1.4. or Ipa3. In some embodiments, the E3 ligase is a mutant E3 ligase, e.g., the E3 ligase comprises one or more substitutions, insertions, and/or deletions.

In some embodiments, the E3 ligase (e.g., a mutant E3 ligase and/or a wild-type E3 ligase) is associated with a disease (e.g., a human disease), e.g., a hypertensive disorder, a neurodegenerative disease, a cancer, an autoimmune disorder, a development disorder, a viral infection, or a bacterial infection.

Further, some embodiments provide a method of measuring E3 ligase activity, the method comprising providing a test composition comprising an E3 ligase and a ubiquitin C-terminal thioester fluorophore; and monitoring the fluorescence (e.g., the fluorescence polarization) of the fluorophore in the test composition.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

(FIG. 1A) C-terminal ubiquitin thioester Ub-MES can form a catalytically active HECT E3~Ub thioester adduct and conjugate ubiquitin to the protein substrates, bypassing ATP, E1, and E2. (FIG. 1B) A time course of Sic60-GFP ubiquitination by Rsp5 and Tagged-Ub-MES. Reaction mixtures were incubated at room temperature for indicated times, quenched with Laemmli buffer, resolved by SDS-PAGE and imaged with in-gel fluorescence scanning and Coomassie staining.

FIG. 2A-2B shows ubiquitination via Rsp5/ByS depends on catalytic cysteine of Rsp5 and enzyme/substrate recognition. FIG. 2A) Rsp5/ByS is dependent on the presence of the Rsp5 catalytic cysteine. Ubiquitination of Sic60-GFP by Rsp5 mutants via ByS was analyzed by in-gel fluorescence scanning. Rsp5 variants without the catalytic cysteine ($Cys^{777}$) are marked with red color. Autoubiquitinated Rsp5 is marked with *. (FIG. 2B) Ubiquitination of Sic60-GFP via Rsp5/ByS depends on the enzyme-substrate recognition. Ubiquitination of Sic60-GFP or Sic60PA-GFP in the presence of Rsp5 or Rsp5ΔWW was analyzed by in-gel fluorescence scanning. Rsp5ΔWW and Sic60PA-GFP are marked with red color. Autoubiquitinated Rsp5 and Rsp5ΔWW are marked with *.

(FIG. 3B) $Rsp5^{806stop}$ forms inactive thioester adduct with Tagged-Ub-MES ($Rsp5^{806stop}$~Tagged-Ub). The formation of $Rsp5^{806stop}$~Tagged-Ub in the $Rsp5^{806stop}$/ByS reaction was confirmed by Western-blotting with Anti-FLAG antibody and Coomassie staining. Reaction mixtures were incubated for 45 minutes at room temperature and quenched by either non-reducing Laemmli buffer or reducing Laemmli buffer containing $NH_2OH$ (20 mM, final concentration). The band corresponding to $Rsp5^{806stop}$~Tagged-Ub adduct is marked as *.

(FIG. 4A) K63-linked polyubiquitin chains formed by Rsp5ΔWW and Tagless-Ub-MES were visualized by Western-blotting with K63-linkage specific anti-ubiquitin antibodies. A mixture of Rsp5ΔWW (1.8 μM) and each Ub-MES mutant was incubated for indicated times and analyzed by Coomassie staining and Western-blotting. The MALDI-TOF analysis was performed for the higher MW bands produced in the reaction. MALDI-TOF analysis was performed for polyubiquitin chains formed by Rsp5ΔWW with (FIG. 4B) Tagless-Ub-MES (lane 4), (FIG. 4C) Tagless-Ub(K48R)-MES (lane 7), and (FIG. 4D) Tagless-Ub(K63R)-MES (lane 10). The band region of 100-250 kDa from lane 4, 7, and 10 was excised for the MALDI-TOF analysis. Any peak corresponding to the calculated polyubiquitin linkage signal (Table S2-S4) is marked with red color. Autoubiquitinated Rsp5ΔWW is marked with *.

FIG. 5A-5E shows N-terminal tags on the ubiquitin (Tagged-Ub) interfere with the formation of K63-polyubiquitin chains by Rsp5ΔWW under native and ByS reaction conditions. (FIG. 5A) The presence of K63-linkages in polyubiquitin chains formed by Rsp5 with Tagged- and Tagless-ubiquitin under both native cascade and ByS condition was detected with Western-blotting using anti-K63-linkage antibody. Native ubiquitination reactions contained UBE1 (0.09 μM), UbcH5a (1.0 μM), hydrolyzed Tagged- or Tagless-ubiquitin (90 μM), Rsp5ΔWW (2.0 μM) and ATP (4 mM). For ByS reaction, the solution of Rsp5ΔWW (2.0 μM) was treated with Tagless-Ub-MES (50 μM) or Tagged-Ub-MES (40 μM) and incubated at room temperature for indicated times. MALDI-TOF analysis was performed for polyubiquitin chains farmed by Rsp5ΔWW with (FIG. 5B) Tagged-Ub via native cascade (lane 3), (FIG. 5C) Tagless-Ub via native cascade (lane 6), (FIG. 5D) Tagged-Ub-MES via ByS (lane 9) and (FIG. 5E) Tagless-Ub-MES via ByS (lane 12). The gel region ranging 100 kDa-250 kDa in lanes 3, 6, 9 and 12 from Coomassie stained gel was excised, digested by trypsin and analyzed by MALDI-TOF. Any peak corresponding to calculated polyubiquitin linkage signals (Supplementary Table 2 and 5.) is marked with red color. Autoubiquitinated Rsp5ΔWW is marked with *.

FIG. 6A-6I) shows Kinetic characterization of Rsp5/ByS. (FIG. 6A) Native chemical ligation between Tagless-Ub-MES with FCys. Reaction mixtures were quenched at different time points and the remaining Tagless-Ub-MES was labeled with FCys, followed by quantification. (FIG. 6B) Tagless-Ub-MES (250 μM) was incubated for indicated times without Rsp5ΔWW (upper panel) or with Rsp5ΔWW (lower panel, 1.5 μM) (FIG. 6C) Consumption rate of Tagless-Ub-MES (250 μM) by Rsp5ΔWW (1.5 μM). (FIG. 6D) The initial reaction rates at different Ub-MES concentration were plotted vs substrate concentration, and $k_{cat}$ and $K_m$ values calculated.

FIG. 7A-7B shows Small molecule thiols as E2 enzyme mimics. (FIG. 7A) A mixture of E1 (0.16 μM), Rsp5ΔWW (2 μM), ATP (4 mM) and ubiquitin (100 μM), was treated with the indicated small molecular thiols followed by incubation for 2 hours at room temperature. Coomassie stain shows autoubiquitinated Rsp5. (FIG. 7B) Shown are canonical ubiquitination cascade that requires E1, E2, and E3 enzymes, and non-canonical ubiquitination cascade, in which E2 enzyme can be replaced with small molecule thiol.

FIG. 8A-8C (FIG. 8A) shows a schematic of an existing technology in which numerous components are needed for screening for E3 ligase inhibitors (e.g., Progenra's approach sold under the commercial name E3LITE). FIG. 8B is a bar plot indicating that the existing technology generates a dose-dependent signal with increasing concentrations of MuRF1. FIG. 8C shows use of the existing technology with multiple classes of E3s.

FIG. 9A-9C shows (FIG. 9A) FRET based approaches to measure autoubiquitinated E3. (FIG. 9B) UbiFlu (e.g., UbFluor) proposed approach to detect enzymatic activity of HECT E3s using UbiFlu (e.g., UbFluor), (FIG. 9C) Comparison of the existing approaches with the newly invented approach to screen for inhibitors or activators of E3 ligases.

FIG. 10A-10B shows (FIG. 10A) Synthesis of UbiFlu (designated Ub-SFlu or UbFluor). (FIG. 10B) Activity of UbiFlu (e.g., UbFluor) probe in the presence of Rsp5. UbiFlu (1.5 uM) and Rsp5ΔWW (0.6 μM) were incubated for indicated times and quenched with Laemmli buffer, resolved by SDS-PAGE and imaged with in-gel fluorescence scanning and Coomassie staining.

FIG. 11A-11C shows (FIG. 1A) time dependent fluorescence decrease in UbiFlu (1.5 μM) treated with Rsp5ΔWW (0.6 μM). (FIG. 11B) relative fluorescent intensity of UbiFlu plotted against time. (FIG. 11C) relative fluorescence polarization of the UbiFlu and Rsp5ΔWW reaction mixture.

(FIG. 12A) Tagged-Ub is inserted into the pTYB1 vector and expressed with BL21 (DE3) cells. The resulting recombinant Tagged-Ub-Intein-CBD fusion protein was isolated using chitin beads. Chitin beads were washed and treated with sodium mercaptoethansulfonate (MESNa) solution to cleave and elute Tagged-Ub-MES. Tagged-Ub-MES is further purified using HPLC and analyzed by ESI-MS. (FIG. 12B) Coomassie staining showing all protein fractions. Ub-MES undergoes hydrolysis during the cleavage by MESNa. The usual yield after HPLC purification is ~2 mg from 1 L of cell culture. (FIG. 12C) Molecular weight of the Tagged-Ub-MES, Tagless-Ub-MES and Tagged- or Tagless Ub. ESI-MS of purified (FIG. 12D) Tagged-Ub-MES and (FIG. 12E) Tagless-Ub-MES.

(FIG. 13A) The domain structure of HECT E3 ligase Rsp5 and fluorescent substrate (Sic60-GFP) shown. Rsp5 contains a characteristic set of protein domains shared by Nedd4 subfamily: C2 domain, three WW domains and the catalytic HECT domain that harbors the catalytic cysteine (Cys$^{777}$). The three WW domains of Rsp5 interact with the proline rich PPPY motif in Sic60-GFP, which facilitates the transfer of ubiquitin onto the lysines of the protein substrate. (FIG. 13B) Ubiquitination of Sic60-GFP by the native E1-E2-Rsp5 cascade can be detected by in-gel fluorescence scanning and Coomassie staining Reaction mixtures containing UBE1 (0.24 μg, 60 nM), UbcH5a (1.4 μg, 2.7 μM), ubiquitin (40 μg, 155 μM), Rsp5 (1.0 μg, 0.4 μM) and Sic60-GFP (1.2 μg, 1.2 μM) with or without ATP (4.0 mM) in ubiquitination buffer I were incubated at room temperature for 1 hour, followed by addition with 6× reducing Laemmlie loading buffer, resolving protein bands by SDS-PAGE (12%), followed by in-gel fluorescence scanning or Coomassie staining (FIG. 13C) Coomassie stained gel of expressed wild type full length Rsp5 or its mutants. Rsp5 and its mutants have lower MW impurities (~20 or ~25 kDa).

(FIG. 15A) The ubiquitination reaction was performed with UBE1 (0.09 μM), UbcH5a (1.0 μM), Rsp5ΔWW (1.5 μM), ATP (4 mM) and Sic60-GFP (0.5 μM) with wild-type ubiquitin (wtUb), ubiquitin K48R (Ub (K48R)), and ubiquitin K63R (Ub(K63R)) ubiquitination buffer I. The reaction was quenched by 6× reducing buffer containing NH$_2$OH (20 mM, final), resolved by SDS-PAGE and imaged by Coomassie staining. The region between MW 130~250 kDa was isolated and digested with trypsin. The MALDI-TOF analysis of polyubiquitin chains formed with (FIG. 15B) wtUb, (FIG. 15C) Ub(K48R) and (FIG. 15D) Ub(K63R) were shown.

FIG. 17A-17E shows Western blotting and MALDI-TOF analysis of polyubiquitin chain formed in autoubiquitination of the full length Rsp5 via ByS. (FIG. 17A) The presence of K63-linkage in polyubiquitin chains formed by the full length Rsp5 and Tagless-Ub-MES (autoubiquitination) was confirmed by Western-blotting with anti-K63-linkage specific antibody. (FIG. 17B) MALDI-TOF analysis of full length Rsp5 (lane 1). The band at ~100 kDa from lane 1 was excised, digested by trypsin and analyzed by MALDI-TOF. The same MALDI-TOF analysis was performed for the polyubiquitin chains formed by the full length Rsp5 autoubiquitination with (FIG. 17C) Tagless wtUb-MES (lane 2), (FIG. 17D) Tagless-Ub(K48R)-MES (lane 3), and (FIG. 17E) Tagless-Ub(K63R)-MES (lane 4). The region 100 kDa-250 kDa from lane 2, 3 and 4 were excised, in-gel digested by trypsin and analyzed by MALDI-TOF to confirm the presence of K63-linkage signal. Any peak corresponding to calculated polyubiquitin linkage signal (Table S2-S4) is marked with red color. There are three tryptic peptides of full length Rsp5 that appears at similar m/z, region: (1) $^{733}$LLQFTTGTSR$^{742}$ (m/z=1123.6106), (2) $^{403}$VYFVDHNTK$^{411}$ (m/z=1122.5578) and (3) $^{347}$AYFVDHNTR$^{355}$ (m/z=1122.5327).

FIG. 18A-18D shows MALDI-TOF analysis of acetylated tryptic peptides of Rsp5ΔWW and Rsp5ΔWW/ByS autoubiquitination. (FIG. 18A) The band at ~80 kDa of 1 of FIG. 3(A) was excised, in-gel digested by trypsin and analyzed by MALDI-TOF. Representative m/z signal corresponding to $^{220}$QYSSFEDQYGR$^{230}$ Rsp5 peptide (calculated average m/z=1379.402) is marked with the red rectangle. (FIG. 18B) The same $^{220}$QYSSFEDQYGR$^{230}$ signal was detected in the 100-250 kDa region from lane 4 of FIG. 3A. However, the calculated m/z value for the K6-polyubiquitin linkage signal ($^{1}$MQIFVK$^{6}$(GG)TLTGK$^{11}$. m/z=1379.6765) is close to the m/z 1379.402 value of Rsp5 peptide, which precludes the clear distinction between these peptides. To test if the signal from K6-polyubiquitin linkage is present, tryptic peptides from both reactions were treated with the acetic anhydride (Table S5). The tryptic peptide from Rsp5ΔWW has only one free amine at the N-terminus of the peptide ($^{220}$QYSSFEDQYGR$^{230}$), whereas that of K6-linked polyubiquitin chain has two ($^{1}$MQIFVK$^{6}$(GG)TLTGK$^{11}$). Therefore, the expected acetylation pattern is different for two peptides: Ac-$^{220}$QYSSFEDQYGR$^{230}$ (m/z=1421.424) and Ac-$^{1}$MQIFVK$^{6}$(GG)TLTGK(Ac)$^{11}$ (m/z=1463.8086), which can be distinguished. Indeed, MALDI-TOF analysis of acetylated tryptic peptides of both (FIG. 18C) Rsp5ΔWW and (FIG. 18D) polyubiquitin chain formed by Rsp5/ByS with Tagless-Ub-MES showed the signal that corresponds to singly acetylated peptide of Rsp5ΔWW. We did not detect the signal for the doubly acetylated K6-linkage Ub peptide, which suggest that Rsp5ΔWW is not likely to form K6-linked polyubiquitin chains.

(FIG. 19A) Time dependence of Sic60-GFP ubiquitination by Rsp5 and Tagless-Ub-MES. The reaction mixtures were incubated at room temperature for indicated times, quenched with 6× reducing Laemmli buffer (NH$_2$OH, 20 mM final), resolved by SDS-PAGE (7.5% gel) and imaged by in-gel fluorescence scanning and Coomassie staining. (FIG. 19B) Protein ubiquitination via Rsp5/Bys with Tagless-Ub-MES depends on the catalytic cysteine of Rsp5. The ubiquitination of Sic60-GFP by Rsp5 or Rsp5 cysteine to alanine mutants in the presence of Tagless-Ub-MES was analyzed by in-gel fluorescence scanning. Rsp5 mutants without the catalytic cysteine (Cys$^{777}$) are marked with red color. Reactions were incubated for 4 hours at room temperature, quenched with 6× reducing Laemmli buffer (NH$_2$OH, 20 mM final), resolved by SDS-PAGE (7.5% gel) and imaged by in-gel fluorescence scanning and Coomassie staining. (FIG. 19C) Protein ubiquitination via Rsp5/Bys with Tagless-Ub-MES is dependent on the enzyme-substrate binding interaction. Sic60-GFP and its mutants were incubated with Rsp5 or Rsp5 mutants under ByS reaction conditions for 4 h, quenched with 6× reducing Laemmli buffer (NH$_2$OH, 20 mM final), resolved by SDS-PAGE (7.5% gel) and imaged by in-gel fluorescence scanning and Coomassie staining. Mutants of Rsp5 and substrates, which recognition motif is deleted (ΔWW and PA, respectively) are marked with red color. (FIG. 19D) Protein ubiquitination via Rsp5/Bys with Tagless-Ub-MES is dependent on the last four amino acids of Rsp5. Ubiquitination of Sic60-GFP via Rsp5$^{806stop}$/ByS is analyzed by in-gel fluorescence scanning and Coomassie staining. The reaction mixture was incubated for 4 hours at room temperature, quenched with 6× reducing Laemmli buffer (NH2OH, 20 mM final), resolved by SDS-PAGE (7.5% gel) and imaged by in-gel fluorescence scanning and Coomassie staining. (FIG. 19E) Rsp5$^{806stop}$ forms thioester adduct with Tagless-Ub-MES (Rsp5$^{806stop}$~Tagged-Ub). The formation of Rsp5$^{806stop}$~Tagless-Ub was confirmed by Western-blotting with Anti-Ub antibody. The reaction mixtures of Rsp5$^{806stop}$ (1.0 μM) and Tagless-Ub (50 μM) were incubated for 45 minutes at room temperature and quenched with either 6× non-reducing Laemmli buffer or 6× reducing Laemmli buffer without NH$_2$OH. For this experiments, we did not use NH$_2$OH to exclude the possibility that NH$_2$OH could cleave the stable isopeptide adduct between Rsp5$^{806stop}$ and Ub. The presence or absence of NH$_2$OH, however, did not affect our conclusions. The band corresponding to adduct of Rsp5$^{806stop}$ and Tagless-Ub is marked with "*".

(FIG. 20A) For ByS reactions, Rsp5ΔWW (1.8 μM) was incubated with 90 μM of each ubiquitin-MES mutants in ubiquitination buffer I. (FIG. 20B) 100-250 kDa region from lane 9 was excised, in-gel digested by trypsin and analyzed by MALDI-TOF (FIG. 20C) For native cascade reactions, the hydrolyzed Ub-MES mutants (100 μM) were mixed with UBE1 (0.09 μM), UbcH5a (1.0 μM), Rsp5 (1.5 μM) and ATP (4 mM) at room temperature for indicated times. (FIG. 20D) The 100-250 kDa region of lane 8 was excised, in-gel digested by trypsin and analyzed by MALDI-TOF. All reactions were incubated for indicated times in room temperature, and quenched by 6× reducing Laemmli buffer containing NH$_2$OH (20 mM, final). Reactions were resolved by 4-20% SDS-PAGE gel (Biorad), and the amounts of polyubiquitinated proteins were detected with Coomassie staining or Western blotting with anti-K63 linkage antibody.

(FIG. 23B) The loading amount of Ub-FCys linearly correlates in the range of 50 ng-2.0 ug. The plot represents mean values±s.d. for three independent experiments.

(FIG. 24A) Initial reaction rates (0 to 5 minutes) at different concentration of Tagless-Ub-MES. Total nmol of Ub-MES consumed by Rsp5 (1.5 µM in 30 µL reaction, 0.045 nmol) was plotted against time. Three sets of experiment were fitted to Michaelis-Menten equation using Prism 6.0 (FIG. 6D). (FIG. 24B) The reaction rate depends on the concentration of Rsp5. The reaction was performed at fixed concentration of Ub-MES (200 µM). When Rsp5 was not added, the amount of Ub-MES did not change. The plot represents mean values±s.d. for three independent experiments.

FIG. 25A-25B shows Nedd4-1 and Parkin are active under ByS reaction conditions. (FIG. 25A) Nedd4-1, a human homologue for Rsp5, was treated with Tagged-Ub-MES, for 2 hours at room temperature, quenched with the reducing Laemmli buffer containing $NH_2OH$ (20 mM, final), and resolved by 7.5% SDS-PAGE gel. The amount of polyubiquitinated proteins was probed with Coomassie staining. (FIG. 25B) Parkin, a human Ring-Between-Ring ligase was treated with Tagged-Ub-MES, for 1 or 3 hours at room temperature, and quenched with the reducing 6× Laemmli buffer containing $NH_2OH$ (20 mM, final). Proteins were resolved by SDS-PAGE (7.5% gel) and polyubiquitnated proteins were detected with Anti-FLAG antibody.

FIG. 26A-26C shows Rsp5ΔWW can form polyUb (G75A) chain. (FIG. 26A) For ByS reactions, Rsp5ΔWW (1.8 µM) was incubated with 100 µM of Tagless-Ub-MES or Tagless-Ub(G75A)-MES in ubiquitination buffer I. All reactions were incubated for indicated times in room temperature, and quenched by 6× reducing Laemmli buffer containing $NH_2OH$ (20 mM, final). Reactions were resolved by 4-20% SDS-PAGE gel (Biorad). 100-250 kDa region from lane 4 and 7 was excised, in-gel digested by trypsin and analyzed by MALDI-TOF (FIG. 26B and FIG. 26C, respectively). All reactions were incubated for indicated times in room temperature, and quenched by 6× reducing Laemmli buffer containing $NH_2OH$ (20 mM, final). Reactions were resolved by 4-20% SDS-PAGE gel (Biorad).

FIG. 27A-27C (FIG. 27A) shows full amino acids sequences for proteins described herein. (FIG. 27B) Calculated average MW for tryptic peptides of full length Rsp5. (FIG. 27C) Calculated average MW for tryptic peptides of Rsp5ΔWW.

FIG. 28A-28B shows calculated tryptic peptide and polyubiquitin-linkage peptides of Tagless-Ub-MES and wtUb). (A) Calculated Average MW for tryptic peptides of Tagless-Ub-MES and wtUb. (FIG. 28B) Calculated average MW for polyubiquitin-linkage peptides of Tagless-Ub-MES and wtUb.

FIG. 29A-29B shows Calculated tryptic peptide and polyubiquitin-linkage peptides of Tagless-Ub(K48R)-MES and Ub(K48R). (FIG. 29A) Calculated MW for tryptic peptides of Tagless-Ub(K48R)-MES and Ub(K48R). (FIG. 29B) Calculated MW for polyubiquitin-linkage peptides of Tagless-Ub(K48R)-MES and Ub(K48R).

FIG. 30A-30B shows calculated tryptic peptide and polyubiquitin-linkage peptides of Tagless-Ub(K63R)-MES and Ub(K63R). (FIG. 30A) Calculated MW for tryptic peptides of Tagless-Ub(K63R)-MES and Ub(K63R). (FIG. 30B) Calculated MW for polyubiquitin-linkage peptides of Tagless-Ub(K63R)-MES and Ub(K63R).

FIG. 31 shows calculated MW for acetylated peptides.

FIG. 32A-32B shows calculated tryptic peptides and polyubiquitin-linkage peptides of Tagged-Ub-MES. (FIG. 32A) Calculated tryptic peptides of Tagged-Ub-MES. (FIG. 32B) Calculated MW for polyubiquitin-linkage peptides of Tagged-Ub-MES.

FIG. 33 shows preparation of an embodiment of the UbiFlu probe.

FIG. 34A shows decrease of Ubi-Flu in terms of pmol as a function of time; FIG. 34B shows the decrease in fluorescence polarization as a function of time; FIG. 34C shows the progress of the ubiquitination reaction by gel electrophoresis.

FIG. 36A-36D shows that Rsp5HECT-UbiFlu can be modeled with Michaelis-Menton kinetics. (FIG. 36A) Reactions contained WT Rsp5 HECT (1 µM) and UbiFlu in 50 mM HEPES 7.5, 150 mM NaCl, 6 µM Tween-20, 0.5 mM TCEP at 25° C. Reactions were monitored for 20 minutes, taking FP measurements every 20 seconds. Each data point was subtracted against a 'no enzyme' control with the same UbiFlu concentration. (FIG. 36B) Data from (FIG. 36A) were fit with Prism software. Triplicate experiments were performed at each concentration. (FIG. 36C) Averaged fluorescence intensities are plotted from the experiments in (FIG. 36A). (FIG. 36D) Mixtures of UbiFlu, Ub, S-Flu, and Rsp5 HECT C777A (1 µM) were incubated in 150 mM NaCl, 50 mM HEPES pH 7.5, 6 µM Tween-20, and 0.5 mM TCEP. The solutions were loaded to wells in a 384 well low volume, low binding plate. Fluorescence polarization was read on a Synergy4 plate reader over 2 minutes and averaged. Sensitivity was set to 46.

FIG. 37A-37B shows methods to determine UbiFlu concentration. (FIG. 37A) Equal concentrations of SFluor and commercial ubiquitin were incubated in 1× PBS with 20 mM β-ME and analyzed with a NanoDrop 3300 fluorospectrometer to make a standard curve. UbiFlu (Sample A) was diluted with a fourfold excess of the PBS/6-ME buffer and was incubated at room temperature for over 1 hour while the standard curve was generated. (FIG. 37B) Ubiquitin Sigma-Aldrich or UbiFlu was diluted seven-fold in 1× PBS with 20 mM β-ME and incubated at 37° C. for 60 minutes. Samples were then mixed with 6× reducing Laemmli buffer and boiled for 5 minutes at 95° C. The resulting solutions were then loaded (1833 ng for 1.25 mg/ml sample) to an 18% acrylamide gel (1.5 mm). Following SDS-PAGE, the gel was stained with Sypro Orange and imaged with the Typhoon 9400 scanner.

(FIG. 38A) The slopes of these curves allow conversion of polarization (x) to UbiFluor concentration (y) under single turnover conditions. They are based upon the observance that polarization at maximal UbiFlu concentration=~155 mP under single turnover conditions. (FIG. 38B) A separate set of curves is generated for the multiturnover condition where maximal polarization=~138 mP. Under both conditions, the minimal polarization after complete UbiFlu conversion=~30 mP.

(FIG. 39A) HECT Rsp5 and its corresponding mutants were reacted with UbiFlu under single turnover reaction conditions. (FIG. 39B) HECT Rsp5 and its corresponding mutants were reacted with UbFluor under multiple turnover reaction conditions. In both cases (FIG. 39A) and (FIG. 39B), enzyme efficiency is represented in the form of $k_{cat}/k_M$ ratio. L771A, E801A, E802A, T803A, V591A, L609A, H775A, T776A, and E778A mutations are defective in transthiolation in the native cascade. E491A, E502A, and 806stop are mutations that cause defects in isopeptide ligation. E618A is the mutation that inhibits HECT E3 processivity, and N779A and 1804A are mutations that were not previously investigated in the native cascade. (FIG. 39C) Representative map of biochemical point mutations scattered throughout the catalytic HECT domain.

Figure 1A:
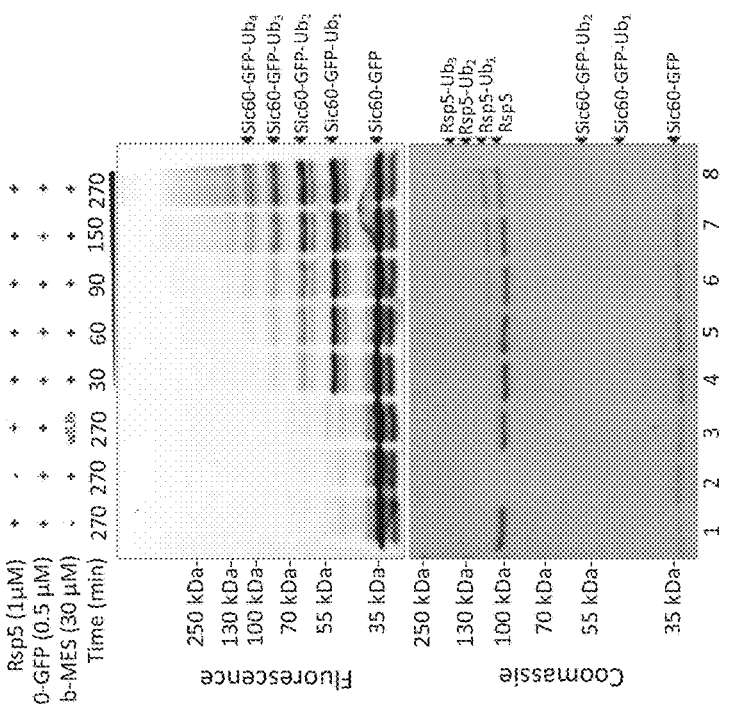
FIG. 1A-1B shows the Bypassing system ByS.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to the biological process of protein ubiquitination and particularly, but not exclusively, to compositions and methods for studying protein ubiquitination and developing therapeutics to modulate protein ubiquitination.

The section headings used herein are for organizational purposes only and are be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

Figure 41:
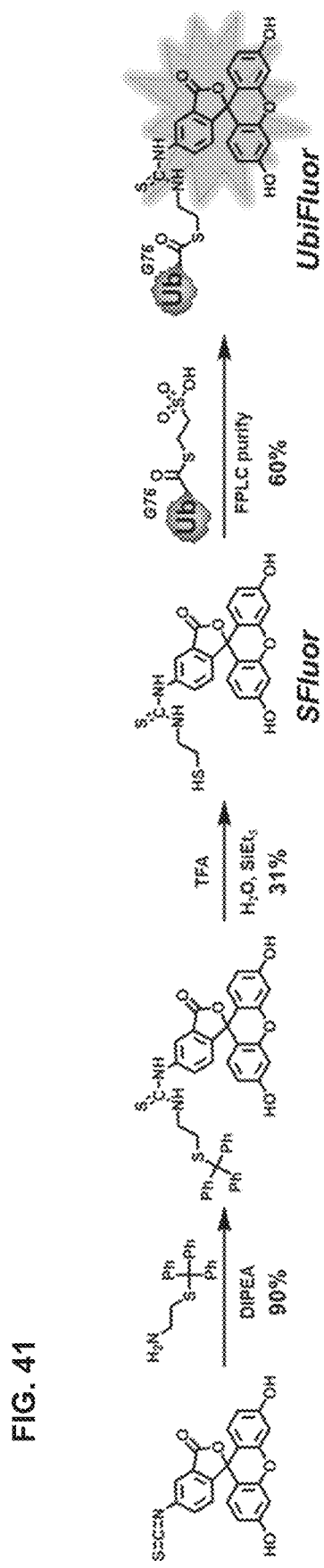
FIG. 41 shows a synthesis scheme for an embodiment of UbiFlu.

As used herein, the terms "UbFlu", "UbiFlu", "Ub-Flu", "Ubi-Flu", "UbFluor", "UbiFluor", "UbSFlu", "UbiSFlu", "Ub-SFlu", "Ubi-SFlu", "UbSFluor", "UbiSFluor", and the like are used interchangeably to refer to the fluorescent ubiquitin probe molecules described herein, e.g., ubiquitin thioester fluorophores (e.g., a ubiquitin C-terminal thioester fluorophore), e.g., as exemplified in FIG. 33 as molecule "III" and/or as the final product of the synthesis scheme shown in FIG. 10 or FIG. 41.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

Ubiquitin has the amino acid sequence SEQ ID NO: 1):

```
MQIFVKTLTGKTITLEVEPSDTIENVKAKIQDKEGIPP
DQQRLIFAGKQLEDGRTLSDYNIQKESTLHLVLRLRGG
```

Description

The technology provided herein is directed to simplifying the highly complex E1→E2→E3 enzymatic cascade for the development of tools to decipher physiological roles of protein ubiquitination. In particular, developing a ubiquitination system without ATP, the E1 enzyme, and the E2 enzyme would provide such a tool.

Initially, efforts were focused on Homologous to E6-AP Carboxyl Terminus (HECT) E3 ubiquitin ligases, which have a catalytic cysteine and form a mandatory HECT E3~Ub thioester complex during the E1-E2-HECT E3 enzymatic cascade.[8-10] HECT E3 ubiquitin ligases are frequently misregulated in cancers and neurodegenerative diseases and therefore tools to study the biochemistry and physiological functions of these enzymes are of significant importance.[11-13] In addition, HECT E3 ubiquitin ligases frequently cross-talk with disease relevant kinase signaling pathways, suggesting the emerging therapeutic importance of HECT E3s.[14]

In the HECT E3 ubiquitination cascade, E1 enzymes activate the C-terminus of the ubiquitin by forming a high energy E1~Ub thioester adduct, while E2 enzymes transfer the ubiquitin from E1 enzymes and onto the catalytic cysteine of HECT E3 ubiquitin ligases (FIG. 1A).[9]

Thus, for ubiquitin to travel from the E1 enzyme to the E3 enzyme, two transthiolation reactions are needed. Since E1 enzymes activate the C-terminus of the ubiquitin, it was contemplated that C-terminal ubiquitin thioesters, such as Ub-MES (mercaptoethanesulfonate)[15], mimic E1~Ub thioesters, thus providing a system that eliminates the E1 enzyme and ATP. Further, C-terminal ubiquitin thioesters undergo a transthiolation reaction with the catalytic cysteine of HECT E3; accordingly, such a ubiquitin thioester mimics the similar function of E2~Ub thioester in the native ubiquitination cascade and provides for a technology that does not comprise the E2 enzyme.

According to the technology provided herein, C-terminal ubiquitin thioesters (e.g., Ub-MES) monoubiquitinate and polyubiquitinate protein substrates in the presence of HECT E3 enzyme in the absence of E1 enzyme, E2 enzyme, and ATP (FIG. 1A). Further, the technology provides Ub-MES probes that are fundamentally different from current activity-based ubiquitin probes for HECT E3 enzymes and deubiquitinating enzymes, which are based on C-terminal ubiquitin electrophiles such as Ub-VME.[16] While Ub-VME acts as a suicide inhibitor of these enzymes, the Ub-MES probes provided herein produce a catalytically active HECT E3~Ub covalent complex.

In some embodiments, the technologies provided herein relate to a system for investigating the mechanism of polyubiquitin chain formation. Currently, proposed models for the polyubiquitin chain formation by HECT E3s are based on the sequential addition model (currently favored) or other models such as the indexation model and the seesaw model.[17] The first model implies that HECT E3s catalyze the formation of isopeptide linkages between ubiquitin molecules and are the primary determinants of the polyubiquitin chain specificity. In this case, HECT E3s assemble polyubiquitin chains via the sequential transfer of ubiquitins from the catalytic cysteine of HECT E3s onto the lysines of the acceptor ubiquitin at the end of the growing polyubiquitin chain. Other models imply that E2 and E3 enzymes pre-assemble polyubiquitin chains with specific linkages on the catalytic cysteines, followed by en bloc transfer of the preassembled polyubiquitin chains from the E3 enzyme onto the protein substrate. To this end, the bypassing system provides a very direct and simple experimental design to dissect these questions.

Additionally, bypassing system facilitates the development of cheap and sensitive assays to screen for small molecule modulators of HECT E3 enzymes. The advantage of these assays is their low cost, since E1 and E2 enzymes are not present in the reaction mixture, and a lower number of false positives associated with the off-target inhibition of E1 and E2 enzymes.

To address these needs, provided herein are embodiments of technologies related to the discovery of a novel two-component enzymatic reaction in which C-terminal ubiquitin thioester Ub-MES directly reacts with the model HECT E3 Rsp5, producing Rsp5~Ub thioester, which ubiquitinates protein substrates, autoubiquitinates, and synthesizes polyubiquitin chains with specific isopeptide linkages. The discovery provides direct evidence that E2 enzymes are dispensable for the formation of K63-specific Ub-Ub isopeptide linkage formation by HECT E3s in vitro. The technology is general since HECT E3 Nedd4-1 and RBR E3 Parkin are also active under these reaction conditions.

Moreover, the discovery of ByS supported the development of a rationally designed hybrid organocatalytic enzymatic cascade in which small molecule thiols, such as glutathione, replace E2 enzymes in the native E1→E2→E3 ubiquitination cascade, leading to efficient E3 enzyme autoubiquitination. In addition, the technology provides embodiments of a novel class of fluorescent probes ("Ubi-Flu") that find use, e.g., in high-throughput assays to screen for inhibitors or activators of HECT E3s, RBR E3s, or NELs, and, in some embodiments, E2 enzymes.

Using Rsp5 HECT E3 as a model ubiquitin ligase, experiments conducted during the development of technologies described herein surprisingly indicated that protein ubiquitination and polyubiquitin chain synthesis occur in the absence of ATP, E1 and E2 enzymes, and require only the E3 enzyme and chemically activated ubiquitin. Such a result was unexpected because the prevailing models based on auto- and substrate ubiquitination require ATP, E1, E2, E3 enzymes, and ubiquitin. In contrast to the native ubiquitination cascade, experiments conducted during the development of technologies provided herein produced a technology for ubiquitination lacking two enzymes and in which the energy of the ATP is converted to the energy of a chemically distinct thioester bond. It was surprising that the described systems provide a protein ubiquitination reaction in spite of these radical chemical transformations relative to previous technologies and the natural processes. Further, the technology described herein relating to the bypassing system recapitulates the mechanism and the isopeptide linkage specificity of the native ubiquitination reaction in vitro. Accordingly, provided herein are embodiments of a technology related to a novel two-component ubiquitination reaction, e.g., for mono-ubiquitination and polyubiquitination of substrates. Importantly, the system requires only two components to ubiquitinate protein substrates, thereby significantly simplifying biochemical studies. The technology bypasses the need for ATP, E1, and E2 enzymes and thus is named a "Bypassing System" or "ByS".

Experiments conducted during the development of technologies described herein indicated that Ub-MES undergoes transthiolation reaction with the catalytic cysteine of Rsp5, and forms an active Rsp5~Ub enzymatic intermediate. Rsp5~Ub thioester formed under these reaction conditions ubiquitinates protein substrates, autoubiquitinates, and synthesizes polyubiquitin chains with specific isopeptide linkages in the absence of E1, E2 enzymes and ATP. This reaction mechanism indicated that the developed two-component ubiquitination reaction is generally applicable to other E3 ligases, which have catalytic cysteines. Additional experiments indicated that HECT E3 Nedd4-1, a human homologue of Rsp5, and Ring Between Ring finger (RBR) E3 ligase Parkin are also active under the bypassing reaction conditions (FIG. 25). As such, the data indicate that C-terminal Ub-thioester probes provide a general and useful tool to study biochemical properties of E3s, such as HECT E3s, NEL E3s, and RBR E3s, in, e.g., protein ubiquitination and polyubiquitin chain formation reactions.

Experiments using the Ub-MES probe indicated that E2 enzymes are dispensable for the formation K-63 linked polyubiquitin chains by Rsp5 in vitro. While not being bound by theory, the data are consistent with both a model based on sequential mechanism of polyubiquitin chain synthesis by Rsp5 HECT E3 and alternative mechanisms that involve oligomeric forms of E3 ligases.[48] Important assumptions of the sequential addition model are that HECT E3s are solely responsible for the (1) $K^{63}$-chain type specificity as well as (2) catalysis of isopeptide bond formation reactions between the ubiquitin molecules. Although previous work demonstrates that HECT domain alone can encode the chain type specificity,[31,44,45] data collected during the development of embodiments of the present technology indicated that E2s are dispensable for Rsp5 catalyzed Ub-Ub isopeptide bond formation reactions regardless of the model, e.g., sequential or en bloc transfer, used to describe ubiquitination of proteins.

Accordingly, ByS finds use as a useful platform to study other biochemical properties of HECT E3~Ub and perhaps RBR E3~Ub thioesters by decoupling ubiquitin ligation from the preceding steps mediated by E1 and E2 enzymes. For example, point mutation approaches to study the role of surface residues of ubiquitin during the ubiquitin ligation step have been difficult to implement because the mutated ubiquitin has to be compatible with E1 and E2 enzymes, which is not always the case.[46] As a consequence, biochemical point mutation studies have been focused on studying the role of surface residues in HECT E3 ligases during the ubiquitin ligation, but not those of ubiquitin.

Using a ubiquitin mutant (e.g., Ub(G75A)-MES), experiments conducted during the development of technologies provided herein indicated that Rsp5 utilized the mutated ubiquitin to form polyubiquitin chains (FIG. 26). Thus, the tools and technologies provided herein form the basis for further mutational studies of ubiquitin to uncover functional significance of various parts of the ubiquitin surface for polyubiquitin chain formation and substrate ubiquitination by HECT E3s.

Alternatively, embodiments provide a Ub-MES with a surface that is engineered to bind particular E3 enzymes, followed by substrate ubiquitination.[47] Such ubiquitin probes find use to identify protein substrates of HECT E3s and other E3s harboring the catalytic cysteines. Although Ub-MES is a less efficient substrate for Rsp5 compared to ubiquitin charged UbcH5a~Ub thioester (FIG. 21), Ub~MES is easier to prepare and has a longer half-life (e.g., can be stored for months) compared to E2~Ub thioesters. Thus, Ub~MES is a convenient reagent for biochemical studies.

Further experiments conducted during the development or embodiments of the technology indicated that small molecule thiols (e.g., glutathione) can replace E2 enzymes in the E1→E2→HECT E3 ubiquitination cascade, serve as E2 enzyme mimics, and act as cyclers between E1 and HECT E3 enzymes similar to the native E2 enzymes. These data indicate that the C-terminal ubiquitin-glutathione thioesters form in cells and thus provide substrates for HECT E3s to ubiquitinate proteins. In accordance with the experimental data, deubiquitinating enzymes regulate non-canonical or aberrant ubiquitination pathways by hydrolyzing C-terminal ubiquitin thioesters to prevent non-specific protein ubiquitination.

Finally, in some embodiments the technology provided herein finds use to design assays for discovering and characterizing HECT E3 and RBR E3 enzyme modulators (e.g., inhibitors, activators). Current assays require E1 and E2 enzymes present in the reaction mixture, which often leads to false positive results. In contrast, the technology described herein provides a simple and elegant solution to this problem by obviating the need to use E1, E2 enzymes and ATP. In particular, data collected during the development of technologies described herein indicated that N-terminally tagged Ub-MES is active in substrate ubiquitination and autoubiquitination assays; thus, embodiments of the technology provide different types of labels installed on the N-terminus of the Ub-MES for high-throughput compatibility purposes. Consequently, methods for assessing the enzymatic activity of HECT E3 are useful for understanding the mechanism of action of these inhibitors or activators.

Thus, in some embodiments are provided UbiFlu probes that find use in designing high-throughput fluorescent assays for screening for modulators (e.g., inhibitors or activators) of HECT E3s. In various embodiments, different fluorophores are attached to UbiFlu, thus producing fluorescent probes with different exitation/emission properties.

The technology is not limited in the fluorophore used in the UbiFlu probe. Thus, in some embodiments, the fluorophore comprises a dye, wherein the dye is a xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610ALEXA FLUOR® 633, ALEXA FLUOR® 647, ALEXA, FLUOR® 660, ALEXA FLUOR® 680, ALEXA FLUOR® 700, ALEXA FLUOR® 750, Oregon Green 488, a fluorescent semiconductor crystal, or a squaraine dye. In some embodiments, fluorophore is described in, e.g., Haugland (September 2005) MOLECULAR PROBES HANDBOOK OF FLUORESCENT PROBES AND RESEARCH CHEMICALS (10th ed.), which is herein incorporated by reference in its entirety.

In some embodiments the fluorophore is one available from ATTO-TEC GmbH (Am Eichenhang 50, 57076 Siegen, Germany), e.g., as described in U.S. Pat. Appl. Pub. Nos. 20110223677, 20110190486, 20110172420, 20060179585, and 20030003486; and in U.S. Pat. No. 7,935,822, all of which are incorporated herein by reference.

In some embodiments, the UbiFlu comprises a linker such as an alkyl, cycloalkyl, aryl, heteroaryl, polymer, carbon nanotube, quantum dot, nanoparticle, etc.

The technology is related to ubiquitination enzymes and pathways. In some embodiments, the technology comprises use of an enzyme that is a HECT or a RBR ("ring between ring fingers") E3s. Exemplary HECT E3 ligases include, e.g., NEDD4, NEDD4L, ITCH, WWP1, WWP2, SMURF1, SMURF2, NEDL1, NEDL2, E6AP, HECTD2, KIAA0614, TRIP12, G2E3, EDD, HACE1, HECTD1, UBE3B, UBE3C, KIAA0317, HUWE1, HECTD3, HERC1, HERC2, HERC3, HERC4, HERC5, and HERC6. Exemplary bacterial HECT-like ligases include, e.g., SopA and NleL. Exemplary ring between ring finger (RBR) ligases include, e.g., ARIH1, ARIH2, CUL9, ANKI1, PARK2, RNF144A, RNF144B, RBCK1, RNF19A, RNF19B, RNF31, RNF216, RNF14, RNF217.

In some embodiments, the technology comprises use of an enzyme that is an E2 enzyme, e.g., UbcH10, UBE2K, UbcH5a, UbcH5b, UbcH5c, UbcH7, or another E2 enzyme such as those that comprise or are characterized by the ubiquitin conjugating E2 enzyme fold (Ubc fold).

In some embodiments, preparation of the UbiFlu probe comprises preparation of ubiquitin C-terminal alkyl thiol (molecule I), preparation of thiol-linker-fluorophore (molecule II) and thiol exchange to produce the flourescent thioester (molecule III) (see, e.g., FIG. 33).

In some embodiments, the ubiquitin c-terminal thioester (molecule I) is prepared via two methods, e.g., either (a) intein technology or (b) E1-mediated method. In the first method (a), the ubiquitin is expressed in E. coli as a recombinant protein with engineered intein-chitin binding domain (Ub-intein-CBD). The Ub-intein-CBD is then captured by chitin beads followed by incubation with small molecular thiols (e.g., mercaptoethansulfate and thioglycolic acid, or other small molecule thiols). Thiol mediated cleavage overnight produces ubiquitin from the recombinant protein in a form of ubiquitin C-terminal thioester (molecule I). In the second method (b), the ubiquitin is incubated with E1 in the presence of ATP and small molecular thiols (e.g. mercaptoethansulfate). The ubiquitin C-terminal thioester is purified by cathion exchange. With either method, the end product is a ubiquitin C-terminal thioester (molecule I).

Then, the thiol-linker-fluorophore (e.g., molecule II comprising a free thiol, linker, and fluorophore) is produced using any coupling chemistry such as, but not limited to, amide conjugation, isocyanate, or isothiocyanate chemistry to conjugate the free thiol, linker, and fluorophore.

Finally, in some embodiments thiol exchange is used to produce ubiqutin C-terminal thioester fluorophore (molecule III, "UbiFlu"). In some embodiments, the molecule III is prepared by incubating molecule I and excess of II in lower pH (e.g., at approximately a pH of 6.5 to 7.0) for 1 hour at room temperature. The excess of small molecules is removed upon desalting using PD10 or Zebaspin columns, leading to fluorescent thioester III.

In some embodiments, the fluorescent ubiquitin probes (UbiFlu) are used to screen for modulators (e.g., inhibitors or activators) for E3 ligases listed above. For example, in some embodiments a high-throughput screening assay is based on Ub-SFlu. In this assay, above mentioned E3s are incubated in 394-well plates and treated with small molecules followed by addition of Ub-SFlu. Reaction mixtures are incubated for one hour at room temperature, followed by quenching with 6M GdnHCl. As E3s react with UbiFlu they cleave the fluorophore from the ubiquitin, which leads to changes in detectable fluorescent polarization. Reaction mixtures are then analyzed by Synergy Fluorecence Microplate Reader (BioTek) to obtain the fluorescence polarization change. The relative changes in fluorescence polarization in each well are then used to score the potency of small molecule inhibitors that are screened. Once initial hits are selected, then the secondary assay is performed using the real-time fluorescence polarization kinetics with UbiFlu to analyze the mode of inhibition of identified inhibitors.

In additional embodiments, UbiFlu is used to assess quantitatively the effect of disease-related point mutations in E3 ligases on their biochemical properties via real-time kinetic experiments. The ligases with disease-related mutations are expressed and incubated with Ub-Sflu, which leads to the cleavage of the fluorophore from the ubiquitin, and the formation of the catalytically active E3~Ub thioester, which undergoes a further isopeptide ligation step. Progress of the reaction is monitored with by real time fluorescence polarization kinetics. Using the proposed method, both transthiolation and isopeptide ligation step can be determined.

Although the disclosure herein refers to certain illustrated embodiments, it is to be understood that these embodiments are presented by way of example and not by way of limitation.

REFERENCES

1 A. Varshavsky, *Annu. Rev. Biochem.*, 2012, 81, 167.
2 A. Hershko, A. Ciechanover, *Annu. Rev. Biochem.*, 1998, 67, 425.
3 C. M. Pickart, *Annu. Rev. Biochem.*, 2001, 70, 503.
4 R. J. Deshaies, C. A. Joazeiro, *Annu. Rev. Biochem.*, 2009, 78, 399.
5 J. R. Lydeard, B. A. Schulman, J. W. Harper, *EMBO Rep.*, 2013, 14 (12), 1050-61.
6 J. Pines, *Nat. Rev. Mol. Cell. Biol.*, 2011, 12, 427.
7 Z. Zhang, J. Yang, E. H. Kong, W. C. Chao, E. P. Morris, P. C. da Fonseca, D. Barford, *Biochem. J.*, 2013, 449, 365.
8 J. M. Huibregtse, M. Scheffner, S. Beaudenon, P. M. Howley, *Proc. Natl. Acad. Sci. U.S.A.* 1995, 92, 2563.
9 M. Scheffner, U. Nuber, J. M. Huibregtse, *Nature*, 1995, 373, 81.
10 S. E. Schwarz, J. L. Rosa, M. Scheffner, *J. Biol. Chem.*, 1998, 273, 12148.
11 M. Scheffner, S. Kumar, *Biochim. Biophys. Acta*, 2014, 1843, 61.
12 F. Bernassola, M. Karin, A. Ciechanover, G. Melino, *Cancer Cell*, 2008, 14, 10.
13 D. Rotin, S. Kumar, *Nat. Rev. Mol. Cell. Biol.*, 2009, 10, 398.
14 H. An, D. T. Krist, A. V. Statsyuk, *Mol. Biosyst.*, 2014, 10, 1643-1657.
15 K. D. Wilkinson, T. Gan-Erdene, N. Kolli, *Methods Enzymol.*, 2005, 399, 37
16 a) A. Borodovsky, H. Ovaa, N. Kolli, T. Gan-Erdene, K. D. Wilkinson, H. L. Ploegh, B. M. Kessler, *Chem. Biol.*, 2002, 9, 1149-59. b) K. R. Love, R. K. Pandya, E. Spooner, H. L. Ploegh, *ACS Chem. Biol.*, 2009, 4, 275.
17 M. Hochstrasser, *Cell*, 2006, 124, 27.
18 S. Park, I. Ntai, P. Thomas, E. Konischeva, N. L. Kelleher, A. V. Statsuk, *Biochemistry* 2012, 51, 8327.
19 Y. Saeki, E. Isono, E. A. Toh, *Methods Enzymol.*, 2005, 399, 215.
20 G. Wang, J. Yang, J. M. Huibregtse, *Mol. Cell Biol.* 1999, 19, 342.
21 B. Andre, J. Y. Springael, *Biochem. Biophys. Res. Commun.* 1994, 205, 1201.
22 O. Staub, D. Rotin, *Structure*, (London, England: 1993) 1996, 4, 495.
23 H. B. Kamadurai, Y. Qiu, A. Deng, J. S. Harrison, C. Macdonald, M. Actis, P. Rodrigues, D. J. Miller, J. Souphron, S. M. Lewis, I. Kurinov, N. Fujii, M. Hammel, R. Piper, B. Kuhlman, B. A. Schulman, *eLife* 2013, 2:e00828.
24 S. Lorenz, A. J. Cantor, M. Rape, J. Kuriyan, *BMC Biology*, 2013, 11, 65.
25 M. A. Verdecia, C. A. Joazeiro, N. J. Wells, J. L. Ferrer, M. E. Bowman, T. Hunter, J. P. Noel, *Mol. Cell*, 2003, 11, 249.
26 H. B. Kamadurai, J. Souphron, D. C. Scott, D. M. Duda, D. J. Miller, D. Stringer, R. C. Piper, B. A. Schulman, *Mol. Cell*, 2009, 36, 1095.
27 C. Salvat, G. Wang, A. Dastur, N. Lyon, J. M. Huibregtse, *J. Biol. Chem.*, 2004, 279, 18935.
28 Y. Kee, N. Lyon, J. M. Huibregtse, *EMBO J.*, 2005, 24, 2414.
29 Y. Kee, W. Munoz, N. Lyon, J. M. Huibregtse, *J. Biol. Chem.*, 2006, 281, 36724.
30 Y. Saeki, T. Kudo, T. Sone, Y. Kikuchi, H. Yokosawa, A. Toh-e, K. Tanaka, *EMBO J.* 2009, 28, 359.
31 H. C. Kim, J. M. Huibregtse, *Mol. Cell. Biol.* 2009, 29, 3307.
32 Z. P. Gates, J. R. Stephan, D. J. Lee, S. B. H. Kent, *Chem. Commun.* 2013, 49, 786.
33 S. Vijay-Kumar, C. E. Bugg, K. D. Wilkinson, W. J. Cook, *Proc. Natl. Acad. Sci. U.S.A.*, 1985, 82, 3582.
34 M. J. Ellison, M. Hochstrasser, *J. Biol. Chem.*, 1991, 266, 21150.

35 P. E. Dawson, T. W. Muir, I. Clark-Lewis, S. B. Kent, *Science,* 1994, 266 (5186), 776.
36 P. E. Dawson, S. B. Kent., *Annu. Rev. Biochem.* 2000, 69, 923.
37 C. M. Pickart, L. A. Rose, *J. Biol. Chem.* 1985, 260, 7903.
38 L. A. Rose, J. V. B. Warms, *Biochemistry,* 1983, 22, 4234.
39 P. Maher, *Ageing Res. Rev.,* 2005, 4 (2), 288.
40 C. N. Larsen, B. A. Krantz, K. D. Wilkinson, *Biochemistry,* 1998, 37, 3358.
41 Y. Fang, D. Fu, X. Z. Shen, *BBA-Rev. Cancer,* 2010, 1806, 1.
42 J. Hurst-Kennedy, L. S. Chin, L. Li, *Biochem. Res. Int.,* 2012, 123706.
43 R. Setsuie, K. Wada, *Neurochem. Int.* 2007, 51, 105.
44 E. Maspero, S. Mari, E. Valentini, A. Musacchio, A. Fish, S. Pasqualato, S. Polo, *EMBO Rep.,* 2011, 12, 342.
45 E. Maspero, E. Valentini, S. Mari, V. Cecatiello, P. Soffientini, S. Pasqualato, S. Polo, *Nat. Struct. Mol. Biol.* 2013, 20, 696.
46 C. M. Pickart, E. M. Kasperek, R. Beal, A. Kim, *J. Biol. Chem.,* 1994, 269, 7115.
47 A. Ernst, G. Avvakumov, J. Tong, Y. Fan, Y. Zhao, P. Alberts, A. Persaud, J. R. Walker, A. M. Neculai, D. Neculai, A. Vorobyov, P. Garg, L. Beatty, P. K. Chan, Y. C. Juang, M. C. Landry, C. Yeh, E. Zeqiraj, K. Karamboulas, A. Allali-Hassani, M. Vedadi, M. Tyers, J. Moffat, F. Sicheri, L. Pelletier, D. Durocher, B. Raught, D. Rotin, J. Yang, M. F. Moran, S. Dhe-Paganon, S. S. Sidhu, *Science* 2013, 339, 590.
48 V. P. Ronchi, J. M. Klein, D. J. Edwards, A. L. Haas, *J. Biol. Chem.* 2014, 289 (2):1033-48.

EXAMPLES

Methods
General

Yeast UBE1, Human UbcH5a (E2-616-100), SUMO1, Nedd8 and all ubiquitin mutants were purchased from R&D Systems. Sodium 2-mercaptoethanesulfonate (MESNa) and wildtype Ubiquitin from bovine erythrocytes was purchased from Sigma-Aldrich. Restriction enzymes (NdeI and SapI) and Chitin beads were purchased from New England Biolabs. Purchased proteins and chemicals were used without further purifications. All biochemical reactions were performed in the ubiquitination buffer. For the native E1-E2-Rsp5 protein ubiquitination reaction, UBE1 (0.09 µM), UbcH5a (1.0 µM), ubiquitin (150 µM), Rsp5 (1.5 µM), ATP (4 mM) and Sic60-GFP (0.5 µM) were used, unless specified otherwise. In-gel fluorescence scanning was performed using Typhoon 9600 (GE Healthcare). All Coomassie images were obtained with the Instantblue stain (Expedeon). Anti-Ub rabbit antibody and anti-DYKDDDDK tag (FLAG-tag) rabbit antibody were purchased from Cell Signaling Technology. Anti-K63-linkage antibody was purchased from Millipore. Goat Anti-Rabbit IgG (H+L)-HRP Conjugate antibody was purchased from Bio-Rad. GST-Rsp5 in pGEX-6p-1 and Cat6-Sic60PY-GFP-6× His in pET3a vectors were gifts from Prof. Andreas Matouschek, and Rsp5ΔWW in pGEX-6p-1 vector was a gift from Prof. Linda Hicke. The original 3× FLAG-6× His-Ub1-75 cloned into PTXB1 vector was a gift from Prof. David O. Morgan, UCSF. All mutations were performed using the Quickchange II kit (Agilent Technologies). The amount of protein was assessed by BioSpec-nano (Shimadzu) or Bradford assay (Biorad).

Buffers

Ubiquitination buffer I: HEPES (25 mM, pH 7.8), NaCl (50 mM), and MgCl2 (4 mM).

Ubiquitination buffer II: HEPES (25 mM, pH 7.8) and NaCl (50 mM).

Lysis buffer I: HEPES (20 mM, pH 6.5), Sodium Acetate (50 mM) and NaCl (75 mM).

Cleavage buffer I: MESNa (100 mM) in lysis buffer I, pH 6.5.

PreScission Protease Buffer: HEPES (50 mM, pH 7.0), NaCl (150 mM) and EDTA (0.1 mM).

6× His purification Buffer A: NaPO4 (50 mM, pH 7) and NaCl (300 mM).

6× His purification Buffer B: NaPO4 (50 mM, pH 7), NaCl (300 mM) and imidazole (10 mM).

6× His purification Buffer C: NaPO4 (50 mM, pH 7), NaCl (300 mM) and imidazole (150 mM).

6× His purification buffer D: HEPES (50 mM, pH 7), NaCl (150 mM) and EDTA (0.1 mM).

6× reducing laemmlie loading buffer: Tris (60 mM, pH 6.8), SDS (120 mg/mL), Glycerol (47% v/v), Bromophenol blue (0.6 mg/mL) and DTT (600 mM).

2× FCys Stop Buffer: HEPES (50 mM, pH 7.0), Urea (10 M), FCys (2 mM), TCEP (3 mM)

Preparation of Ub-MES

The 3× FLAG-6× His-Ub1-75 region of 3× FLAG-6× His-Ub1-75 cloned into PTXB1 vector was amplified by PCR. The amplified fragment was cloned into the pTYB1 vector by NdeI and SapI restriction digestion of insert and vector. Digested DNA fragments were purified with the standard PCR purification kit (Qiagen), followed by ligation using DNA ligase (New England Biolabs). Using the Quickchange II kit (Agilent Technologies), an extra glycine was inserted to the C-terminus of Gly75 of the inserted protein. The nucleotide sequence of the resulting construct was validated. DNA constructs were then transformed into BL21 (DE3) cells. Cells were grown in 1 L of LB media, which was supplemented with 100 µg/mL ampicillin. When the culture reached OD600 of 0.6, protein expression was induced with 0.2 mM (final concentration) of IPTG, and grown for 18 hours at 15° C. Cells were harvested by centrifugation at 8,000 g, for 20 minutes at 4° C. and resuspended in lysis buffer I containing protease inhibitors (Roche complete protease inhibitor cocktail). Suspended cells were sonicated (5 cycles, 1 min each cycle with 1 min delay in between) on ice. The resulting cell lysates were centrifuged at 18,000 rpm, for 30 minutes at 4° C., and the resulting supernatants were collected. In parallel, 10 mL of chitin bead slurry (New England Biolabs) was washed with lysis buffer I by preincubating chitin beads with the lysis buffer I at 37° C. for 30 minutes. Cell lysates were then incubated with chitin beads for 1 hour at 37° C. with shaking at 150 RPM. Chitin beads were subsequently washed with 5×20 mL of lysis buffer I and incubated with 5 mL of cleavage buffer I with shaking (125 rpm) at 30° C. for at least 12 hours. Eluates were collected and chitin beads were washed with lysis buffer (2×5 mL). Combined eluates were concentrated with Amicon Ultra (MWCO 3,000, Millipore) to 2 mL total volume. Concentrated Tagged-Ub-MES was further purified using HPLC, using C18 column, 5 µm, 250×21.2 mm (Restek) with solvent B gradient (5% to 95%) for 40 minutes (solvent A is 95:5 H2O:CH3CN and 0.1% TFA; solvent B 5:95 H2O:CH3CN and 0.1% TFA). Collected fractions were pooled and freeze-dried overnight to obtain white powder. The typical yield of Tagged-Ub-MES is 1-2 mg/L. The dried Tagged-Ub-MES was reconstituted in diluted lysis buffer (HEPES 10 mM, Sodium Acetate 25 mM, NaCl 38 mM, pH 6.5) on ice, aliquoted, snap-freezed and stored at −80° C. We have found that the Tagged-Ub-MES could be stored for months. All other UB-MES variants were prepared using the same experimental procedure as above.

Preparation of Rsp5

BL21(DE3) cells (Novagen) were transformed with GST-Rsp5 cloned into pGEX-6p-1 vector and GST-Rsp5 expression was induced with IPTG (0.5 mM) at 18° C. overnight. Cells were then harvested by centrifugation, resuspended in PBS (Complete Mini Protease Inhibitor Cocktail, Roche) and lysed with sonication. The glutathione agarose beads (Pierce Biotechnology) were washed with PBS at 37° C. for 1 hour prior to subsequent incubation with cell lysate for 1-2 h at 4° C. Glutathione beads were washed (3×10 mL PBS), and Rsp5 was eluted by cleavage by PreScission Protease in PreScission Protease buffer overnight at 4° C. All Rsp5 mutants were prepared using the same experimental procedure.

Preparation of His-tagged Sic60-GFP

BL21(DE3)pLysS cells (Novagen) were transformed with Cat6-Sic60PY-GFP-6× His in pET3a vector, and the cell cultures were grown to OD600=0.6, followed by the induction of Sic60-GFP with IPTG (1.0 mM) at 37° C. for 4 hours. Cells were then harvested, resuspended in 6× His purification Buffer A, which was supplemented with protease inhibitors (Complete Mini Protease Inhibitor Cocktail, EDTA free, Roche). After centrifugation, the resulting supernatant was incubated with HisPur Ni-NTA Resin (Pierce Biotechnology) for 1-2 h at 4° C. Beads were washed with PBS and 6× His purification Buffer B. Bound proteins were eluted with 6× His purification Buffer C. The elutate was dialyzed against 6× His purification buffer D overnight and stored at −80° C. All other Sic60-GFP mutants were prepared using the same experimental procedure.

Protein Ubiquitination Via Rsp5/ByS.

All reactions (30 μL total volume) were performed in the ubiquitination buffer described in General information section. Protein ubiquitination were initiated by adding Tagged- or Tagless-Ub-MES to the reaction mixtures. All reactions were performed at room temperature for indicated amounts of time and were quenched with reducing Laemmli buffer containing 20 mM of hydroxylamine to remove remaining thioesters, unless specified otherwise. To analyze thioester adducts of Rsp5806stop~Ub, non-reducing Laemmli buffer was used. Sample mixtures (7.0 μL total volume) were resolved by 7.5% SDS-PAGE, unless specified otherwise. The ubiquitination of Sic60-GFP was monitored by in-gel fluorescence scanning. DYKDDDDK FLAG tag antibody (Cell Signaling Technology) and K63-polyubiquitin chain antibody (Millipore) were used according to the manufacturer's protocol.

MALDI-TOF Analysis.

Protein bands on SDS-PAGE gel were visualized using Coomassie staining, excised, and in-gel digested with trypsin for 12-16 hours according to protocol released by the Virginia Tech Center for Genomics. 1 Digested peptides were analyzed by MALDI-TOF (Bruker Autoflex III MALDI, reflectron positive mode, α-Cyano-4-hydroxycinnamic acid as a matrix). The tryptic peptides are predicted using Swiss-prot software. All molecular masses of peptides derived from branching at any lysines on Tagged-Ub-MES, Tagless-Ub-MES, Tagless-Ub(K48R)-MES, Tagless-Ub(K63R)-MES were calculated as listed (FIGS. 28-31). In order to acetylate tryptic peptides, the 10 μL of digested solution was treated with 25 μL of acetic anhydride in Methanol (1:3 v/v) for one hour, followed by evaporating solution with Speed-vac, reconstituting in water (0.1% TFA) and desalting with ZipTip (Millipore) for subsequent MALDI-TOF analysis.

Pulse-chase Assay

The Ub~UbcH5a was prepared as previously described. 2 E1 enzyme UBA1 (250 nM), UbcH5a (2.0 μM), ubiquitin (5 μM) and ATP (1 mM) were incubated for 40 min at room temperature in the ubiquitination buffer I. The reaction mixture was quenched by adding 5 mM of EDTA, followed by buffer exchange with ubiquitination buffer II using Zeba spin desalting column. 10 μL of the resulting solution was treated with 10 μL of Rsp5ΔWW (3.0 μM) in ubiquitination buffer II to initiate the reaction. Similarly, 10 μL of Tagless-Ub-MES (2.0 μM) in ubiquitination buffer II were treated with the 10 μL of Rsp5ΔWW (3.0 μM) in ubiquitination buffer II to initiate reaction.

Metal Affinity Purification of Ubiquitinated Sic60-GFP

Slurry (100 μL) of Talon Metal Affinity Resin (Clontech) is washed with PBS 2×1 mL. The resin is then resuspended in 100 μL of PBS and 15 μL of this slurry was added to the 60 μL of ByS reaction mixture that contained Rsp5, GFP-Sic60 and Taggless-Ub-MES. After incubation at room temperature for 5 minutes with mild shaking, beads were centrifuged for 2 minutes at 15 kG, followed by supernatant removal. Beads were washed with PBS (pH 7.4, 300 μL), wash buffer (25 mM imidazole in PBS, pH 7.4, 300 μL), and bound proteins were eluted with 50 μL of elution buffer (250 mM imidazole in PBS, pH 7.4). Eluted proteins were treated with the 6× reducing Laemmlie buffer that contained 20 mM NH2OH, and resolved by SDS-PAGE.

Kinetic Analysis

All reactions were performed in room temperature. At indicated time points, 5 μL of the reaction mixture was mixed with 5 μL of 2× FCys stop buffer. The mixture was incubated at 37° C. for 16 hours and quenched by adding 2 μL of 6× reducing Laemmli buffer. The mixture was further diluted with 1× reducing Laemmli buffer so that 7 μL of sample loading to each well contains 1-2 μg of ubiquitin-MES. 18% SDS-PAGE gel was used to maximize the separation between free FCys and labeled ubiquitin that appears at ~10 kDa, followed by in-gel fluorescence scanning. The fluorescence intensity of each band was quantified using ImageJ. The relative intensities against the 0 min band were multiplied by total nmol of Ub-MES in the reaction mixture. For each data point, 3 independent experiments were performed. Data sets were fitted to Michaelis-Menten equation using Graphpad Prism 6 to obtain Kcat, Vmax and Km values.

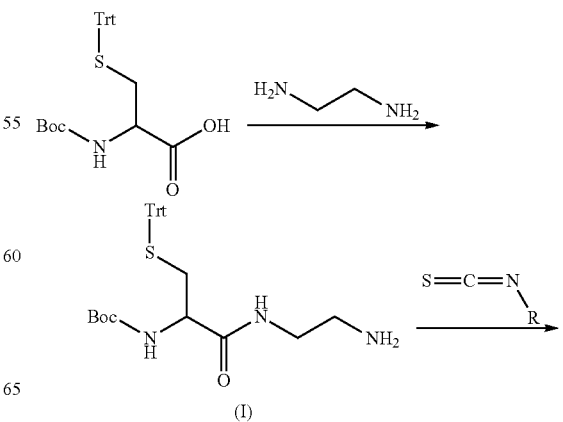

Scheme S1-Synthesis of FCys

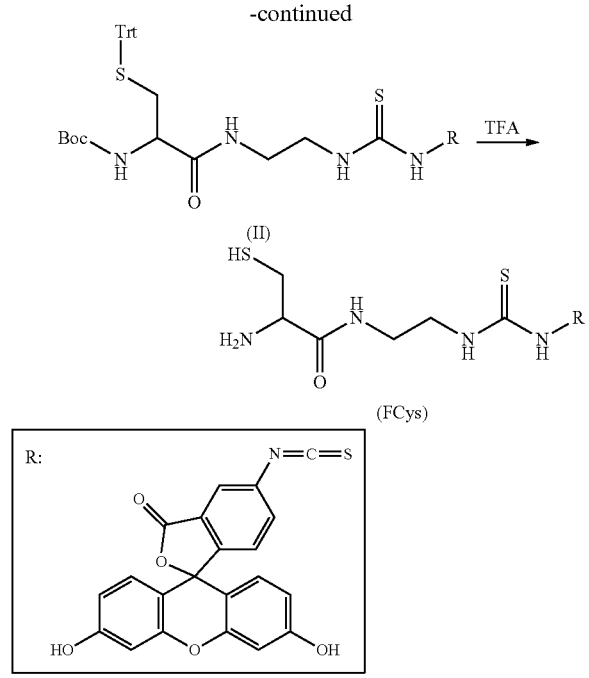

(FCys)

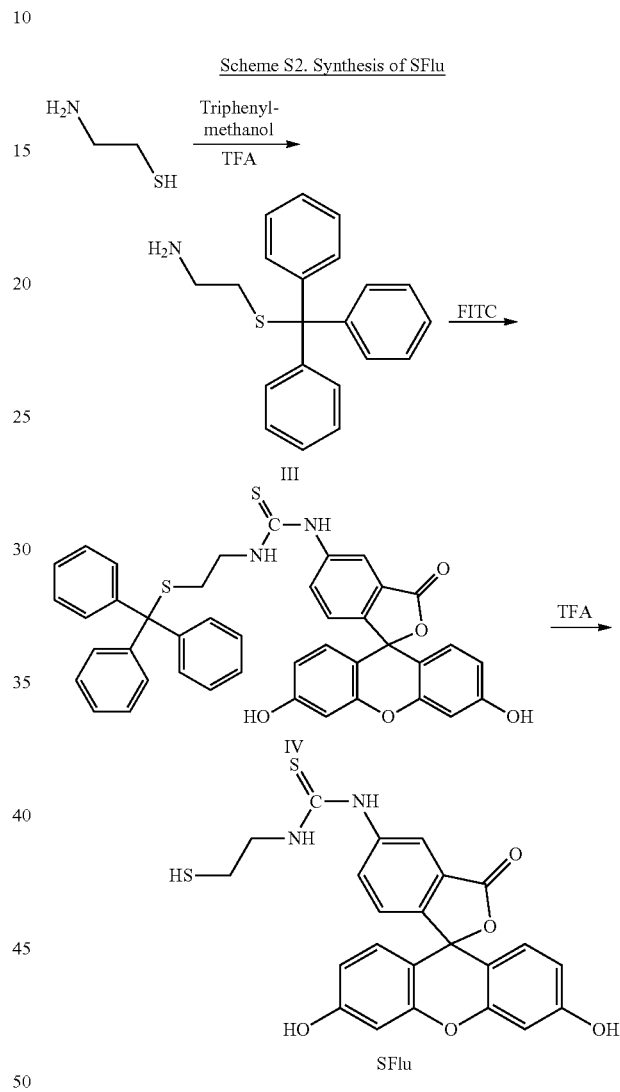

N-Boc-S-Trityl-N-2-aminoethyl-L-cysteinamide (I). To the DMF solution (10 mL) of N-Boc-S-trityl-L-cysteine (1.0 g), carbonyl diimidazole (430 mg) was added and stirred for 30 min at room temperature. The ethylene diamine (1.4 mL) was added and stirred further for 2 hours at room temperature. Dichloromethane (50 mL) was added to the solution and washed with water (5×50 mL) and brine (1×50 mL). The solution is further dried with anhydrous magnesium sulfate and concentrated in vacuo until white crystalline of compound I precipitate. The precipitated crystalline was collected and dried in vacuo (750 mg, 68%). 1H NMR (500 MHz, CDCl3): δ 7.25 (6H, d), 7.12 (6H, t), 7.06 (3H, t), 6.20 (1H, t), 4.7 (1H, d), 3.69 (1H, dd), 3.07 (2H, ddd), 2.58 (3H, m), 2.37 (1H, dd), 1.42 (9H, s); 13C NMR (500 MHz, CDCl3): δ 170.7, 155.4, 144.4, 129.6, 128.0, 126.1, 80.3, 53.7, 46.1, 42.3 41.3, 33.9, 28.3.

N-Boc-t-Trityl-N-[2-[[[(fluorescein-5-yl)amino]-thioxomethyl]amino]ethyl]-L-cysteinamide (II). Fluorescein isothiocyanate (54.0 mg) was added to a solution of the compound I (70.13 mg) in DMF (2 mL) and stirred for 16 hours at room temperature. Reaction mixture was diluted with dichloromethane (30 mL), and washed with water (2×30 mL) and brine (1×30 mL). Organic layers were dried over anhydrous magnesium sulfate and the organic layer was concentrated in vacuo. The residue was purified by silica gel chromatography (EA:H=3:1, 3% MeOH) to afford orange red solid (II). 1H NMR (500 MHz, DMSO-d6), δ 8.17 (1H, s), 8.0 (1H, s), 7.72 (1H, d), 7.35-7.22 (15H, m), 7.17 (1H, d), 6.69 (2H, d), 6.60-6.64 (4H, m), 3.95 (1H, m), 3.56 (2H, m), 3.29 (2H, t), 2.37 (2H, d), 1.31 (9H, s); 13C NMR (500 MHz, CD3OD) δ 181.1, 172.8, 170.9, 169.1, 159.9, 15, 152.3, 144.8, 141.6, 129.8, 129.5, 128.7, 128.6, 127.2, 127.1, 126.6, 125.0, 120.0, 113.1, 110.2, 102.7, 83.4, 78.8, 60.2, 53.9, 43.9, 38.3, 34.5, 28.6.

N-[2-[[[(Fluoroscein-5-yl)amino]thioxomethyl]amino] ethyl]-L-cysteinamide (FCys). 50 mg of compound II was treated with 1 mL of TFA containing water (2.5 v/v %) and triisopropylsilane (2.5 v/v %) under nitrogen. The reaction mixture was stirred at room temperature for 1 hour. The reaction mixture was transferred to 50 mL of cold diethyl ether and precipitated by centrifugation at 4000 g (10 min). After decanting the ether layer, the orange precipitate was dissolved in MeOH and transferred to a glass scintillation vial and concentrated in vacuo (25 mg, 83%). The stock solution in DMSO (200 mM) was prepared and saturated aqueous sodium bicarbonate solution was slowly added until the color of solution turns to be dark orange red. This stock solution was stored at −20° C. until use.

Scheme S2. Synthesis of SFlu

Synthesis of compound (III). To the mixture of cysteamine hydrochloride (1 g, 8.8 mmol) and TFA (1.3 mL, 17 mmol) in CH2Cl2 (30 mL), was added tritylchloride (2.4 g, 8.8 mmol). The reaction mixture was stirred for 16 hours at room temperature. The reaction was quenched by the 1 M NaOH solution (20 mL) and the organic phase was diluted with methylene chloride (50 mL), washed with brine (20 mL) and dried over magnesium sulfate. The white crystalline was obtained from ether/n-pentane precipitation (455 mg, 1.42 mmol, 16% yield). 1H NMR (400 MHz, CDCl3); δ 7.43-7.42 (d, 6H), 7.29-7.26 (t, 3H), 7.21-7.19 (t, 3H), 7.16-7.11 (m, 3H), 2.62 (t, 2H), 2.23 (t, 2H). 13C NMR (400 MHz, CDCl3); δ 144.4, 129.8, 128.6, 127.4. 67.7, 36.9, 29.4.

Synthesis of compound (IV). To the mixture of compound III (330 mg, 1.0 mmol) and DIPEA (345.7 μl, 2.0 mmol) in DMF (2 mL), was added FITC (400 mg, 1.0 mmol). The reaction mixture was stirred at room temperature for 16 hours. The reaction was treated with water (20 ml) and extracted with methylene chloride (3×20 mL). The combined methylene chloride solution was washed with brine (20 mL) and dried over magnesium sulfate. After the concentration, the residue was purified with flash column (ethylene acetate, 8% MeOH) to afford dark orange solid (354 mg, 0.5 mmol, 50% yield). 1H NMR (400 MHz, CDCl3); δ 7.43-7.42 (d, 6H), 7.29-7.26 (t, 3H), 7.21-7.19 (t, 3H), 7.16-7.11 (m, 3H), 2.62 (t, 2H), 2.23 (t, 2H). 13C NMR (400 MHz, CDCl3 ); δ 144.4, 129.8, 128.6, 127.4, 67.7, 36.9, 29.4.

Synthesis of SFlu. To the compound IV (30 mg, 0.042 mmol) in the flask, was added 1 mL of TFA solution (2.5% triethylsilane and 2.5% water). The mixture was stirred for one hour at room temperature and poured into the 50 mL of cold diethyl ether. The cloudy mixture was precipitated with centrifuge (4,000 g, 10 min) to obtain orange pellet (16.3 mg, 0.035 mmol, 83% yield).

Preparation of Ub-SFlu.

Reaction

SFlu stock solution (1:1 DMSO-Water, 50 mM) was treated with the aqueous solution of $NaHCO_3$ (1.0 M) until color changed to dark red and a thiol odor arose. This stock solution was used to prepare UbiFlu. Final reaction mixture contained the following components: 1 M HEPES (110 μL, pH 7.5), 100 mM TCEP (100 μL aqueous solution), 50 mM SFlu stock solution (300 μL), 6 M Gdn-HCl (300 μL) and Ub-MES (300 μL). The reaction mixture was shaken for 1 hour at room temp on vortex.

Purification

The slurry of CM52 (1 g) was prepared with 50 mM NaOAc (pH 4.5, 15 ml) and incubated for 30 minutes at room temp in the column. The reaction was diluted to 5% final DMSO content, concentrated, and then desalted (Zeba spin column). The desalted solution was diluted with 50 mM NaOAc (pH 4.5, 50 mL). The column was washed with 50 mM NaOAc (pH 4.5, 15 mL). The hydrolyzed Ub was washed with 50 mM NaOAc (pH 5.5, ~10 ml) until the fluorescent product started eluting out (monitored with BiospecNano). To elute Ub-SFlu, 50 mM NaOAc (pH 7.5, 20 mL) was added. The eluate was concentrated with Amicon and buffer exchanged with storage buffer (12.5 mM HEPES, PH 6.8, 25 mM NaCl).

Measurement of Concentration

The standard curve was obtained using series FITC dilution in the characterization buffer (1× PBS, 10 mM BME) and measuring absorption at 498 nm with BiospecNano. The prepared Ub-SFlu was diluted to 10 fold with the characterization buffer and measured absorption at 498 nm to confirm the concentration with obtained standard curve.

Example 1

Rsp5 Ubiquitinates Sic60-GFP in the Presence of Ub-MES

Figure 1B:
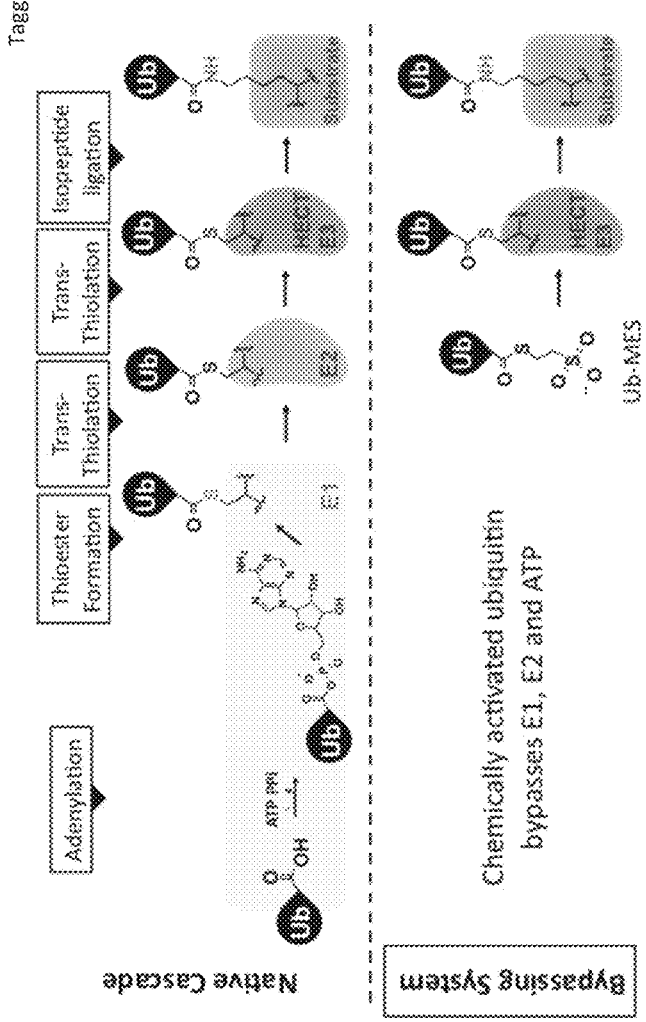
Figure 13A:
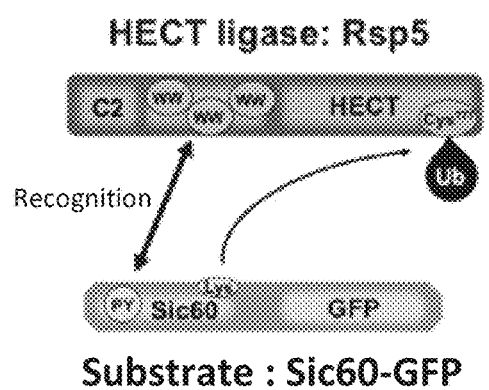
FIG. 13A-13C shows preparation of the model system.
Figure 13B:
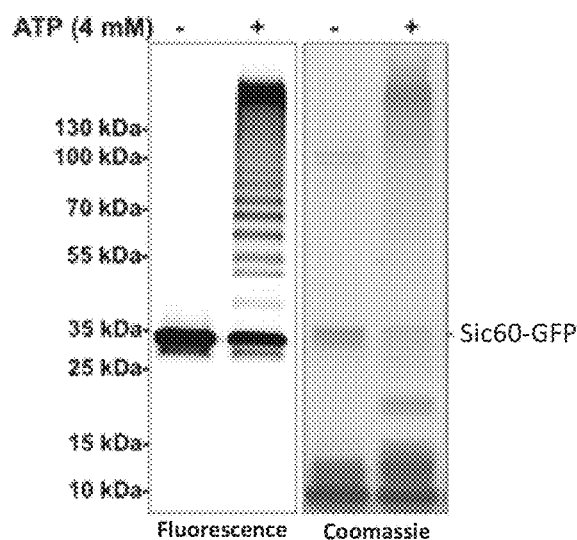
Figure 13C:
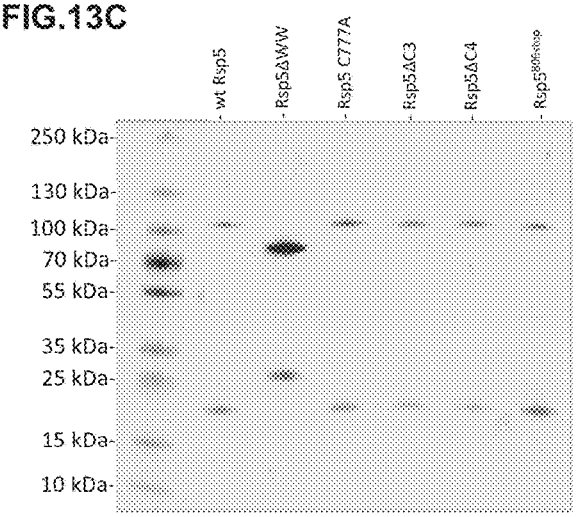

During the development of embodiments of the technology provided herein experiments were conducted using N-terminal 3× FLAG-6× His tagged ubiquitin 1-76 mercaptoethanesulfonate thioester (Tagged-Ub-MES, MW 12.5 kDa) (FIG. 12).[15] Rsp5 was used as a model HECT E3 ubiquitin ligase in addition to a yeast homolog of human HECT E3 (Nedd4-1) and a fluorescent substrate (Sic60-GFP) as described previously (FIG. 13).[18,19] Treatment of Rsp5 and Sic60-GFP with Tagged-Ub-MES produced higher molecular weight fluorescent bands that corresponded to the combined molecular weights of Sic60-GFP (35 kDa) and increments of the Tagged-Ubiquitin (12.5 kDa) (FIG. 1B).

Figure 14:
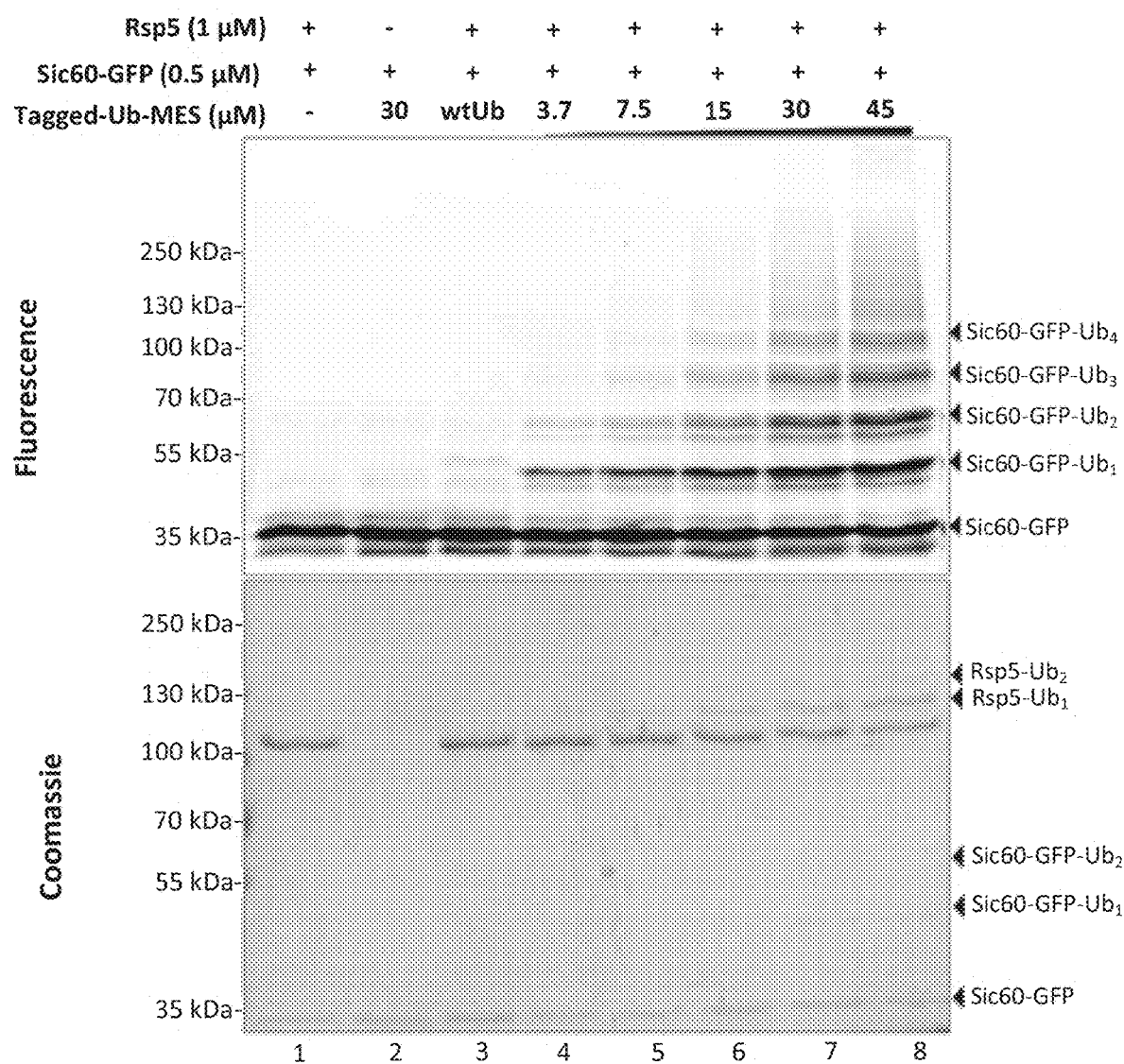
FIG. 14 shows ubiquitination of Sic60-GFP is dependent on the concentration of Tagged-Ub-MES. Rsp5 and Sic60-GFP were treated with increasing amounts of Tagged-Ub-MES in ubiquitination buffer I. The reaction was incubated for 2 hours at room temperature, followed by quenching with 6× reducing Laemmli buffer containing hydroxylamine (20 mM final concentration), resolved by 7.5% SDS-PAGE gel and analyzed by in-gel fluorescence scanning and Coomassie staining. The fluorescence scanning (upper) and Coomassie staining (lower) of SDS-PAGE gel showed higher molecular weight bands that correspond to the combined mass of Sic60-GFP-Ub$_x$ and Rsp5-Ub$_x$.
Figure 15A:
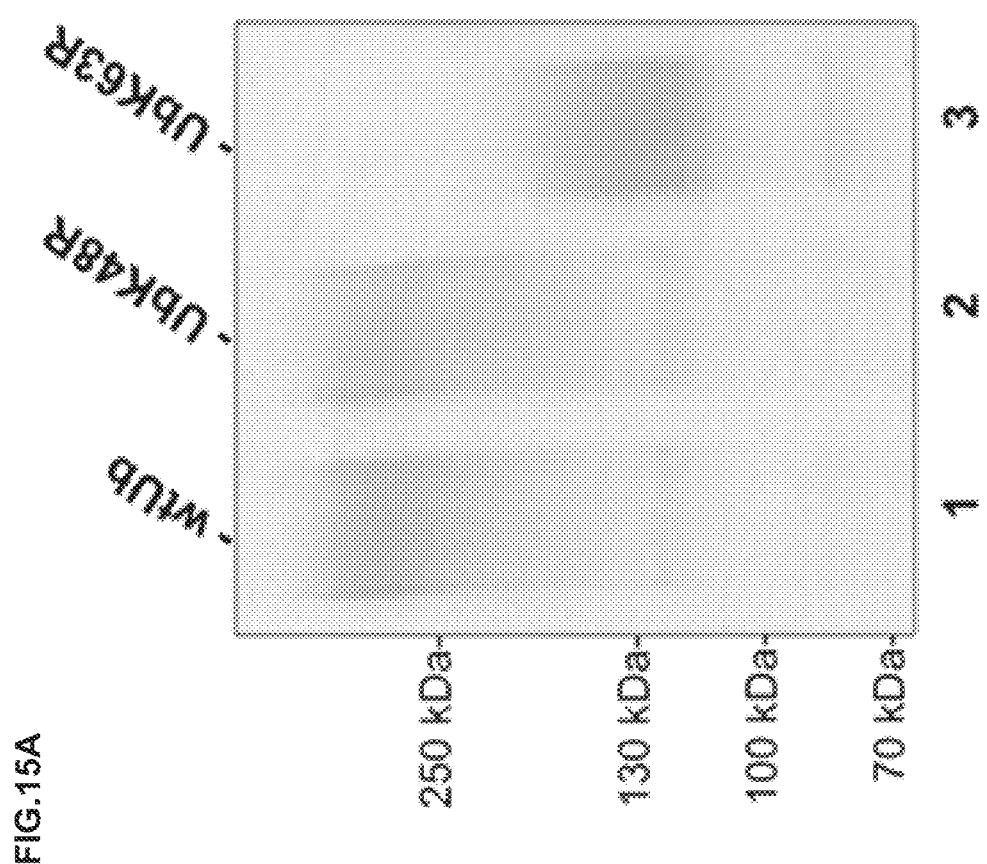
FIG. 15A-15D shows MALDI-TOF analysis of polyubiquitin chain formed by Rsp5ΔWW via native cascade.
Figure 15B:
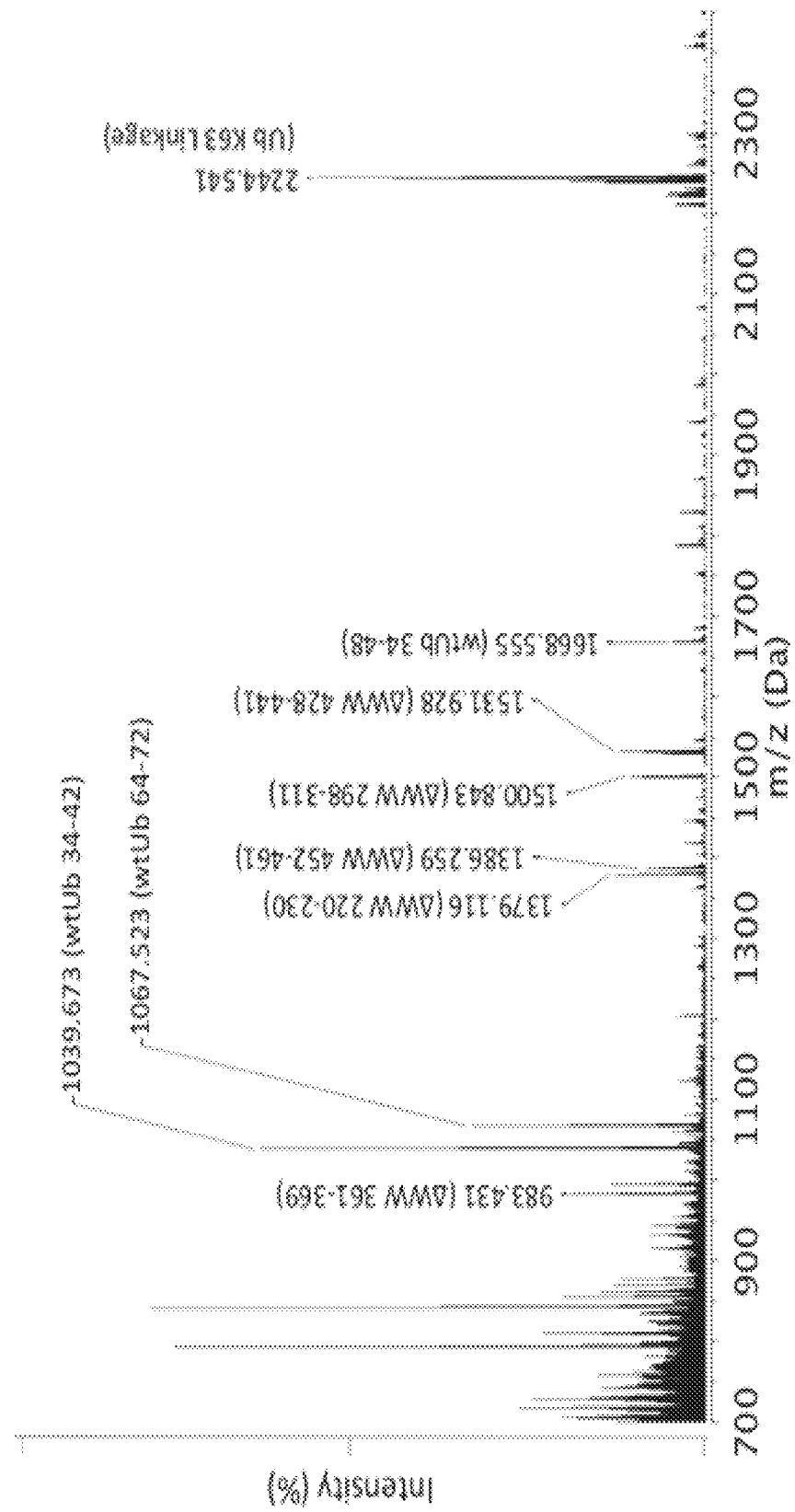
Figure 15C:
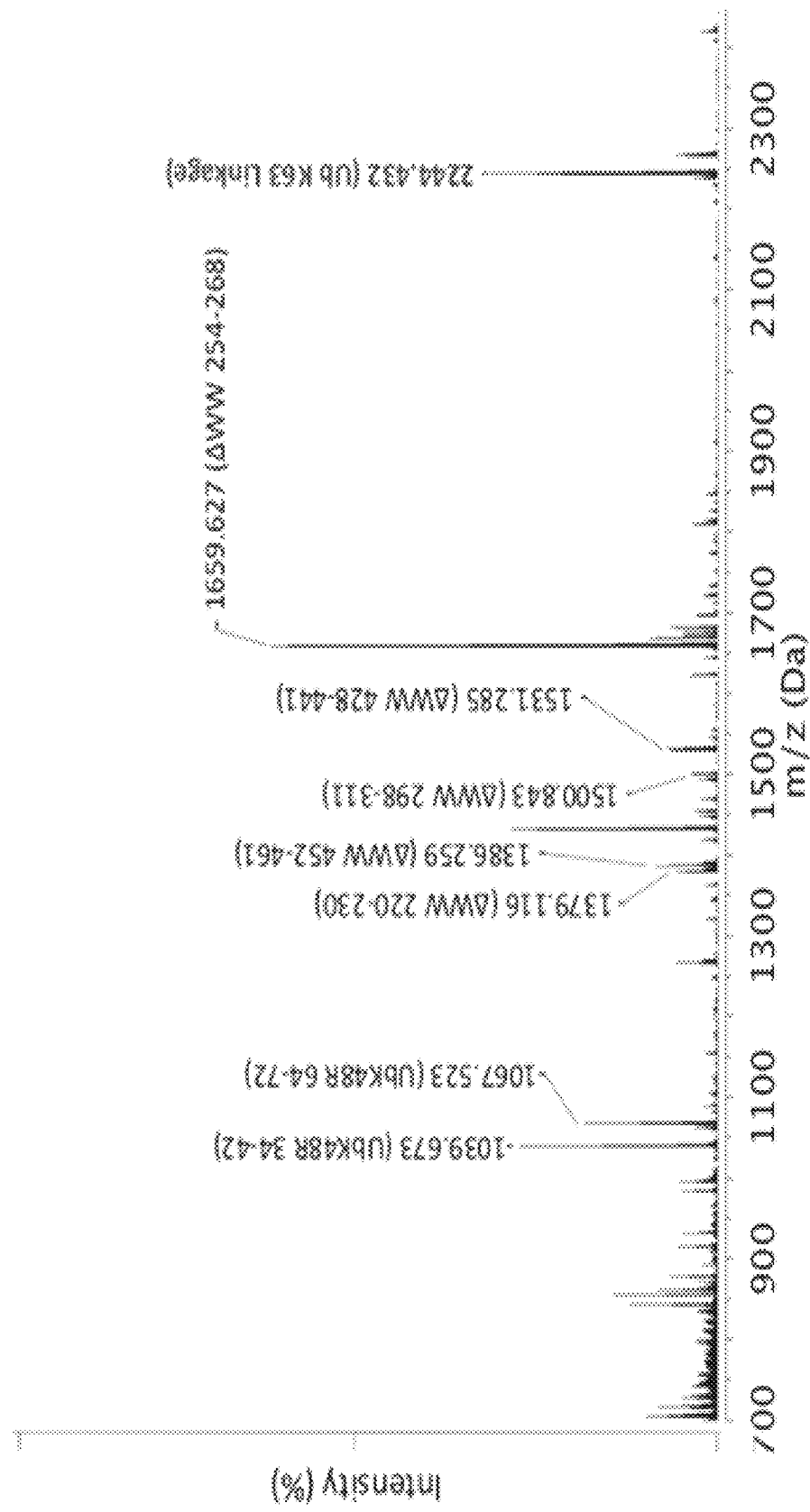
Figure 15D:
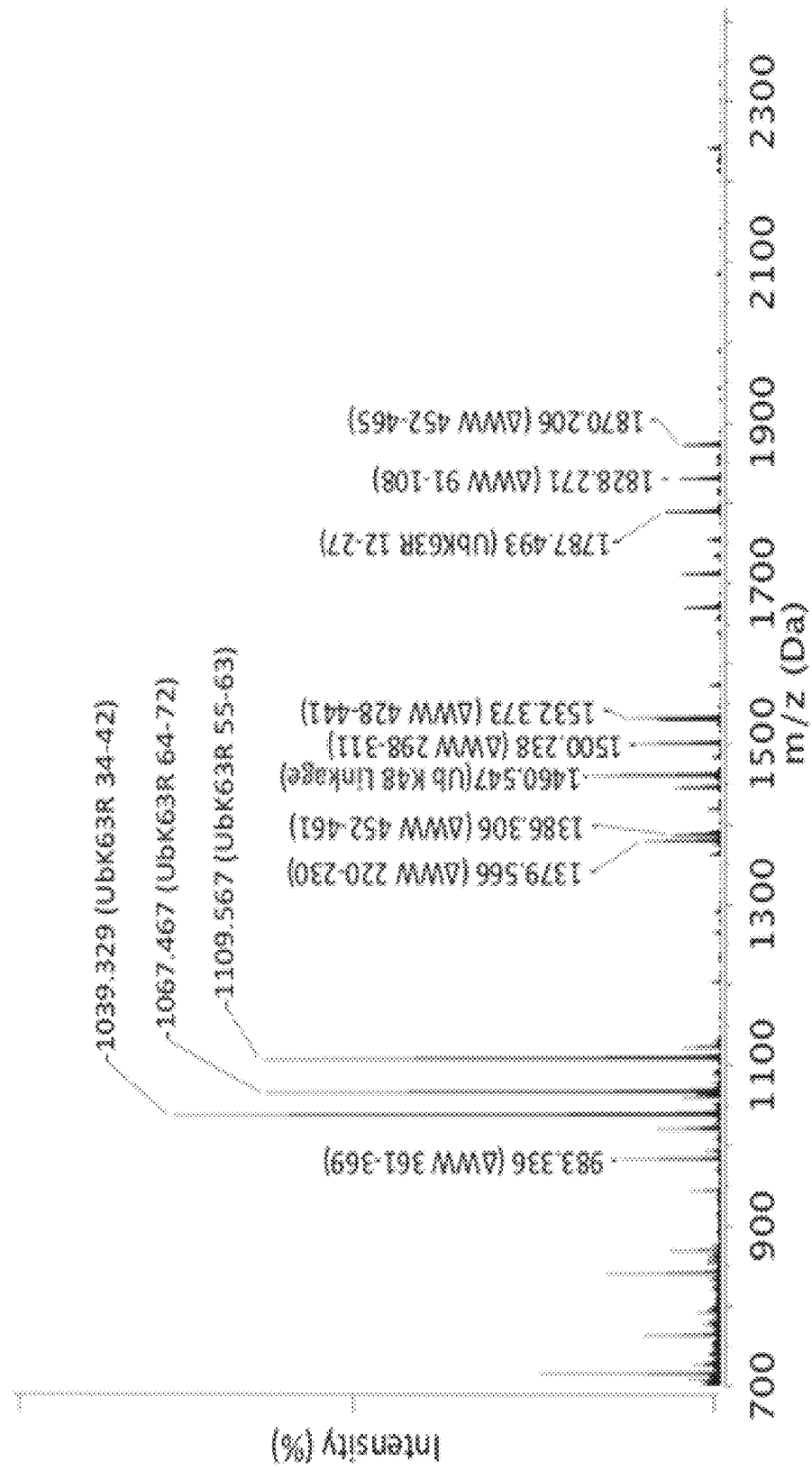

The reaction was time- and concentration-dependent with respect to Tagged-Ub-MES (FIG. 1B and FIG. 14), and the ubiquitinated Sic60-GFP could be visualized by Coomassie staining. In addition, similar to the native ubiquitination, we observed autoubiquitination of Rsp5, as judged by Coomassie staining. Remarkably, Sic60-GFP was not labeled by Tagged-Ub-MES in the absence of Rsp5, despite the presence of 27 nucleophilic lysines in Sic60-GFP (FIG. 1B, lane 2), indicating the high chemical specificity of the reaction. Since the discovered system bypasses the need for ATP, E1, and E2 for ubiquitination reaction, the system is referred to herein as the "Bypassing System" (ByS).

Example 2

Protein Ubiquitination by Rsp5/ByS Depends on the Catalytic Cysteine of Rsp5 and Enzyme/Substrate Recognition After experiment indicated that Rsp5 ubiquitinates Sic60-GFP in the presence of Tagged-Ub-MES (Example 1), further experiments were conducted to test the transthiolation of tagged-Ub-MES with the catalytic $Cys^{777}$ of Rsp5 to produce catalytically active Rsp5~Ub thioester. First, data were collected to monitor the ubiquitination of Sic60-GFP by Rsp5 in the Bypassing System (Rsp5/ByS) by catalytic or other solvent exposed surface cysteines in Rsp5.[20] In particular, several Rsp5 mutants were constructed and tested:

Rsp5 C777A in which the catalytic $Cys^{777}$ is mutated to alanine;

Rsp5Δ3C in which three non-catalytic surface cysteines are removed (C455A, C517S, and C721A mutations); and Rsp5Δ4C in which all surface cysteines including the catalytic cysteine are removed (C777A, C455A, C517S, and C721A mutations).

Data collected indicated that only the native Rsp5 and Rsp5Δ3C ubiquitinated Sic60-GFP under the ByS conditions (FIG. 2A). Notably, Rsp5 C777A that contains three non-catalytic surface cysteines (e.g., $Cys^{455}$, $Cys^{517}$, and $Cys^{721}$) could not ubiquitinate Sic60-GFP or itself (FIG. 2A, lane 5), indicating that protein ubiquitination via Rsp5/ByS strictly depends on the catalytic cysteine of Rsp5.

Further, experiments were conducted to investigate the ubiquitination of Sic60-GFP via Rsp5/ByS and characterize the specific binding between the Rsp5 and Sic60-GFP. First, mutant Rsp5 and Sic60-GFP proteins were designed and produced that lack key interacting elements: (1) Rsp5ΔWW in which three WW domains of Rsp5 are deleted and (2) $Sic60^{P4}$-GFP in which PY motif was mutated (e.g., PPPY→PPPA).[21,22] Data collected from experiments indicated that ablation of these interaction motifs decreased ubiquitination of Sic60-GFP in the native protein ubiquitination reaction, e.g., due to the disruption of enzyme-substrate interactions.[18] Similarly, ubiquitination of Sic60-GFP via Rsp5/ByS was decreased when Rsp5ΔWW or $Sic60^{P4}$-GFP were used (Lane 5-10 of FIG. 2B). The decrease in the ubiquitination of Sic60-GFP was not due to the lack of enzymatic activity, since both native Rsp5 and Rsp5ΔWW were autoubiquitinated (Lanes 4, 6, 8, and 10 in FIG. 2B Coomassie staining). Taken together, these results indicate that the ubiquitination of Sic60-GFP via Rsp5/ByS depends on the enzyme-substrate recognition.

Example 3

Rsp5 Mediated Ubiquitination Under ByS Conditions Exploits the Native Mechanism

While not being bound by theory, one possibility accounting for the observed ubiquitination via Rsp5/ByS is a proximity-based transfer reaction in which Rsp5~Tagged-Ub intermediate adopts a catalytic architecture that is distinct from that of the native system.[23] In this scenario, ubiquitin charged to the catalytic cysteine of Rsp5 randomly collides with, and is transferred to, nearby substrate lysine residues of Sic60-GFP due to the innate conformational flexibility of Rsp5.[24-26] Further, recent findings indicate that the catalytic cysteine of Rsp5 and the target lysine of Sic60-GFP become proximal even in the absence of E1, E2, ATP, and loaded ubiquitin, which are detectable by chemical cross-linkers under certain conditions.[18] Under this theory, the observed protein ubiquitination via Rsp5/ByS does not reflect the native enzymatic reaction, but is rather a proximity driven ubiquitin transfer.

Figure 3A:
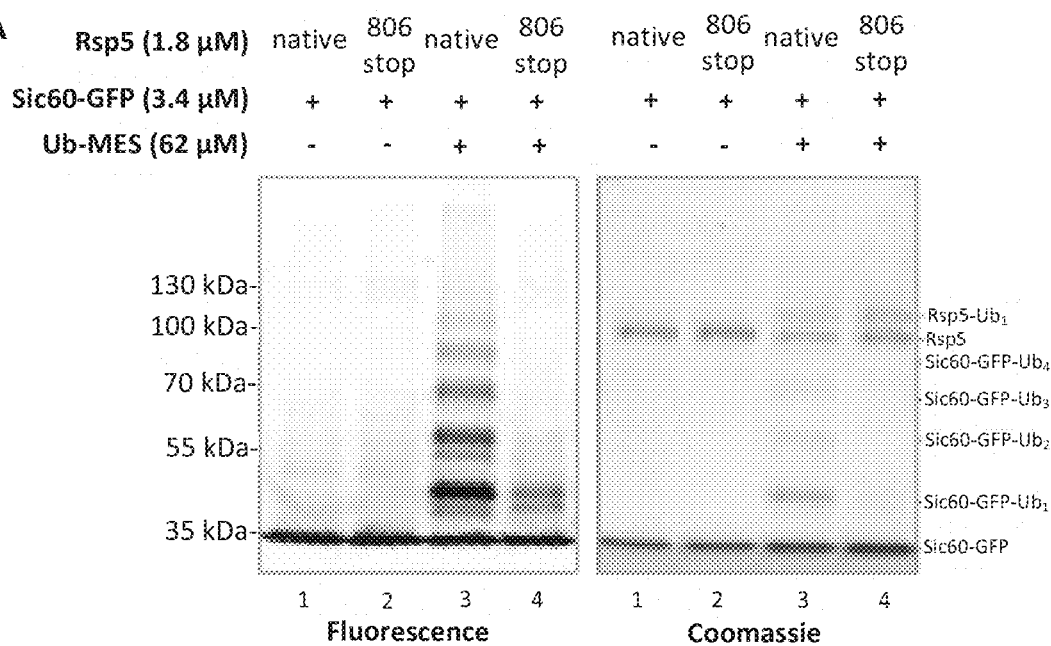
FIG. 3A-3B shows ubiquitination via Rsp5/ByS recapitulate intrinsic mechanism of Rsp5 (FIG. 3A) Ubiquitination of GFP-Sic60 via Rsp5/ByS is dependent on the last four C-terminal amino acids of Rsp5. The ubiquitination of Sic60-GFP via $Rsp5^{806stop}$/ByS is analyzed by in-gel fluorescence scanning, after 4 hours of the reaction time.
Figure 3B:
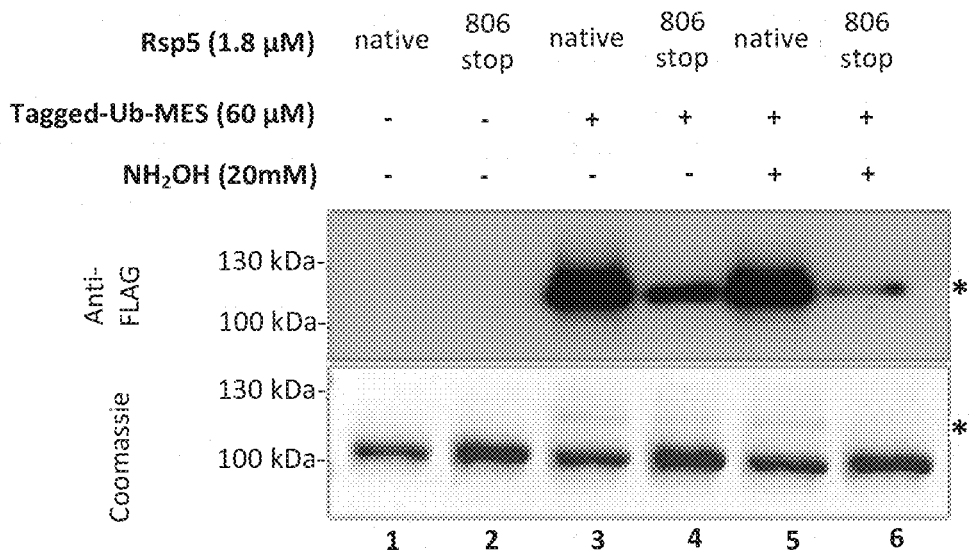

Accordingly, during the development of embodiments the technology provided herein, experiments were conducted to prepare and test a mutant $Rsp5^{806stop}$, in which the last four C-terminal residues of Rsp5 are deleted. In the native ubiquitination reaction, the $Rsp5^{806stop}$ mutant does not transfer the ubiquitin onto the protein substrates, although it can still receive ubiquitin from E2~Ub and form an inactive $Rsp5^{806stop}$~Ub thioester.[27] Recently, Kamadurai et al. demonstrated that the $Phe^{806}$, which is located at the C-lobe of the Rsp5, is involved in the interaction of C-lobe with N-lobe to form a bilobal composite catalytic site of Rsp5 to ligate ubiquitin onto the substrate.[23] Results showed that ubiquitination of Sic60-GFP via $Rsp5^{806stop}$/ByS was severely impaired similar to $Rsp5^{806stop}$ in the native ubiquitination cascade (FIG. 3A, lane 4). In addition, similar to the native ubiquitination reaction, $Rsp5^{806stop}$ did form $Rsp5^{806stop}$~Ub thioester adducts (FIG. 3B, lane 4), as judged by the sensitivity of $Rsp5^{806stop}$~Ub band to hydroxylamine (FIG. 3B, lane 6). This indicates that Rsp5/ByS ubiquitinates Sic60-GFP via the intrinsic catalytic mechanism of Rsp5 utilized in the native ubiquitination cascade.

Example 4

Rsp5 Synthesizes K63-linked Polyubiquitin Chains Without E2 Enzymes

Figure 4B:
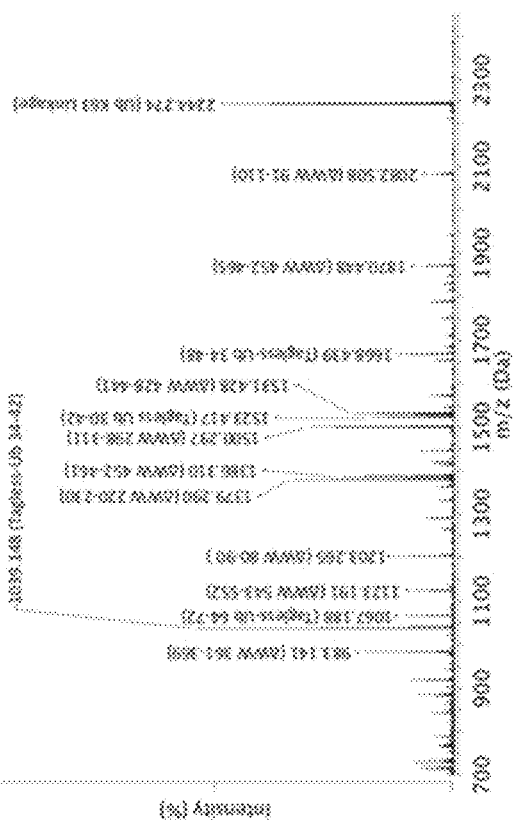
FIG. 4A-4D shows Rsp5/ByS forms K63-linked polyubiquitin chains.
Figure 4A:
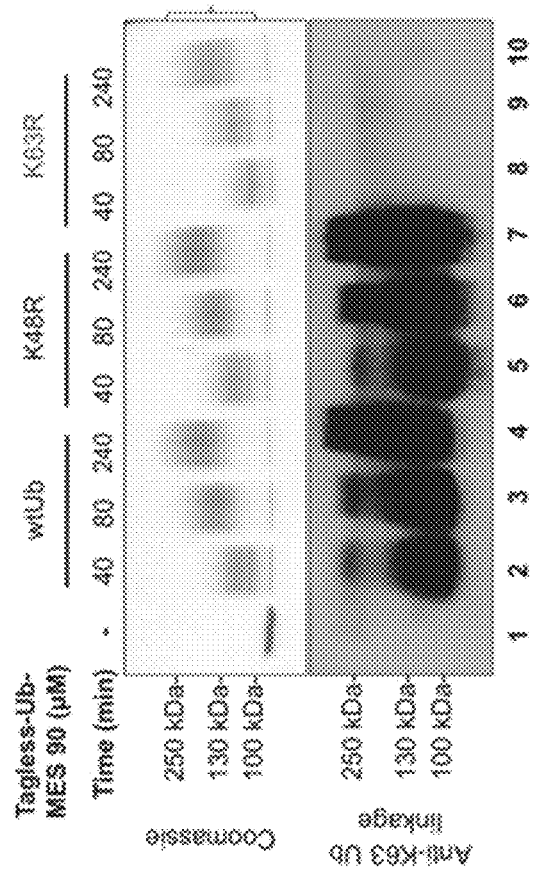
Figures 4C, 4D:
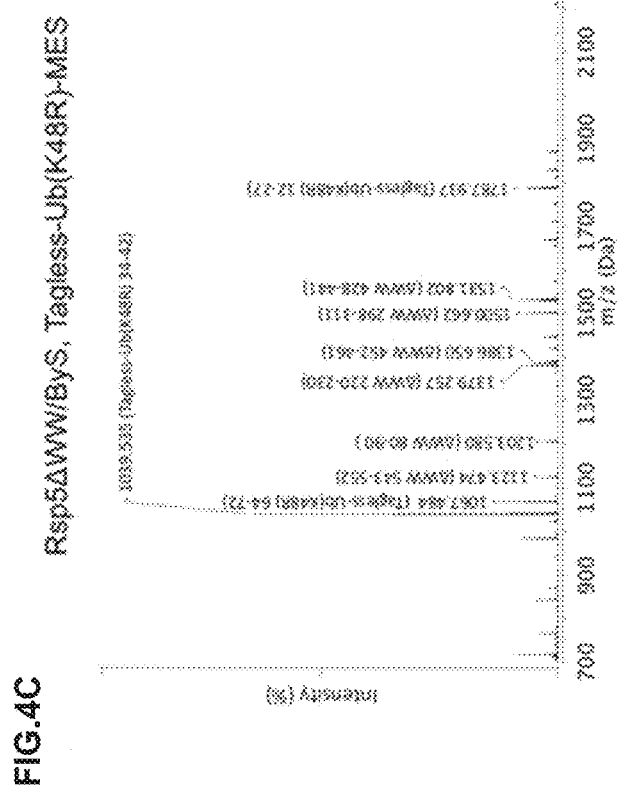

As shown in the above Examples, Rsp5/ByS ubiquitinates Sic60-GFP via the intrinsic catalytic mechanism. Accordingly, experiments were conducted to test the role of Rsp5 in forming K63-linked polyubiquitin chains under ByS reaction conditions with the Tagless-Ub-MES (e.g., Ub-MES containing native ubiquitin) variants to monitor the formation of polyubiquitin chains. Data were collected from experiments testing the following Tagless-Ub-MES variants: (1) Tagless-Ub(wt)-MES; (2) Tagless-Ub(K48R)-MES; and (3) Tagless-Ub(K63R)-MES. The formation of K63-linked polyubiquitin chains at different time points was then evaluated using K63-linkage specific anti-ubiquitin antibodies (FIG. 4A) and MALDI-TOF analysis (FIG. 4B-D). K63-linked polyubiquitin chains were produced under ByS reaction conditions when Rsp5 was treated with Tagless-Ub(wt)-MES or Tagless-Ub(K48R)-MES (FIG. 4A, lane 2-7). Treatment of Rsp5ΔWW with Tagless-Ub(K63R)-MES, however, did not produce K63-linked polyubiquitin chains (FIG. 4A, lane 8-10).

Figure 16:
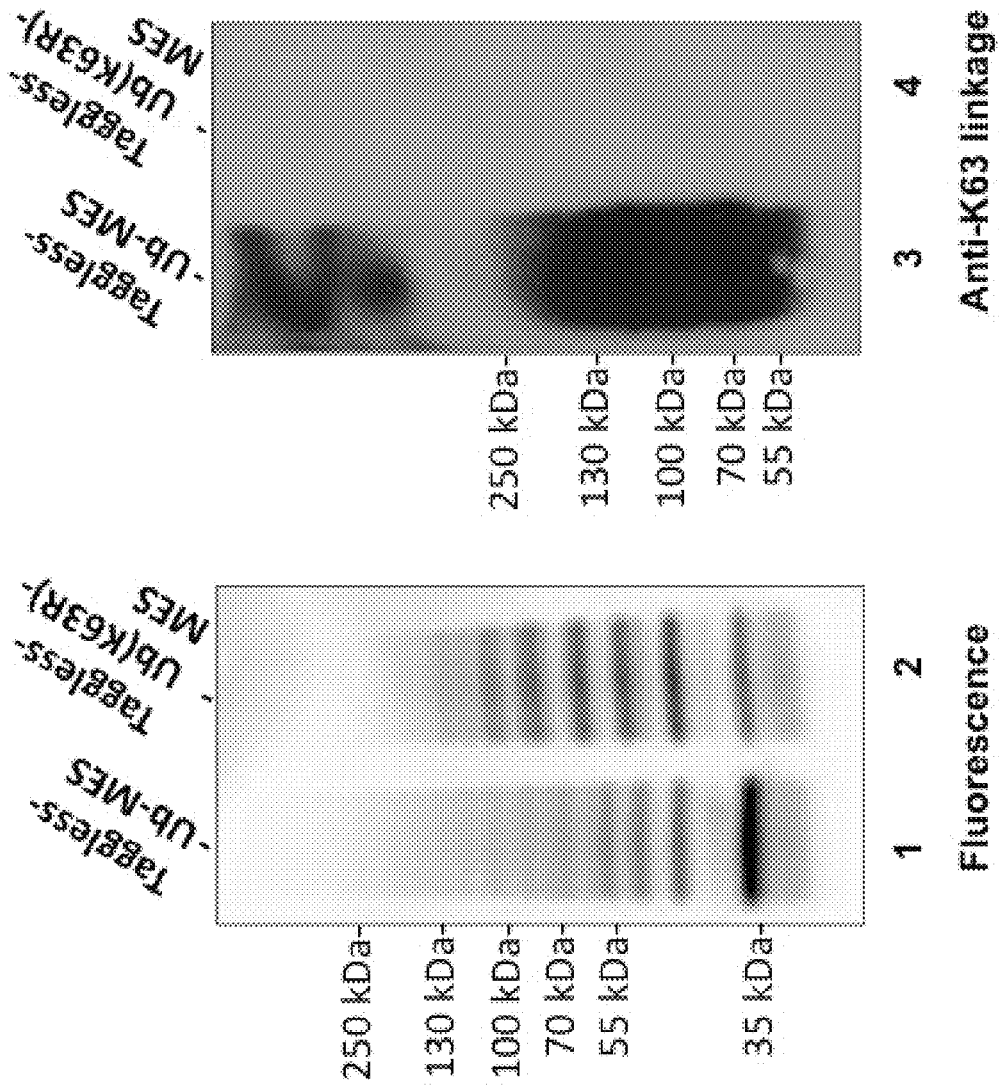
FIG. 16 shows Rsp5/ByS catalyzes K63-specific polyubiquitin chain synthesis on the Sic60-GFP substrate. Full length Rsp5 (5 μM), Sic60-GFP (10 μM) and Tagged- or Tagless-Ub-MES (40 μM) in ubiquitination buffer I were incubated 6 hours at room temperature. The ubiquitinated Sic60-GFP that has C-terminal 6× His tag was immobilized on nickel beads and eluted by imidazole (250 mM). The eluate was resolved by SDS-PAGE (4-20%) and the amount of K-63 linked polyubiquitin chains on Sic60-GFP was probed using K-63 specific antibodies.

Further experiments were conducted in which polyubiquitin chains were isolated from a gel (e.g., the region at approximately 100-250 kDa, which contained the most ubiquitin chains as judged by coomassie (FIG. 4A, lane 4, 7 and 10)), digested with trypsin in-gel, and analyzed using MALDI-TOF. Similar to the Western blotting results, data collected indicated a prevailing K63-linkage signal for the reaction mixtures of Rsp5ΔWW treated with Tagless-Ub (wt)-MES or Tagless-Ub(K48R)-MES (FIGS. 4B and C, respectively), but not with the Tagless-Ub(K63R)-MES (FIG. 4D). Moreover, when Tagless-Ub(K63R)-MES was used, K48-linked chains formed (as detected by MALDI-TOF), which is a known biochemical property of Rsp5 in the native cascade (FIG. 4D).[30,31] Besides K63 and K48 isopeptide linkages, other major linkage signals of polyubiquitin chains were not detected in MALDI-TOF experiments except for a weak signal of K11-polyubiquitin linkage for Tagless-Ub(K63R)-MES. The ability of Rsp5 to utilize $Lys^{11}$ of ubiquitin for polyubiquitin chain synthesis has been previously documented, thus further supporting the overall similarities of the ByS system and the native ubiquitination reaction.[31] Similar results were observed when polyubiquitin chains were prepared using the native ubiquitination cascade with Rsp5ΔWW and wtUb, Ub(K48R), and Ub(K63R) (FIG. 15). Rsp5/ByS was also confirmed to produce K63-linked polyubiquitin chains on the Sic60-GFP protein substrate (FIG. 16).

Figure 17A:
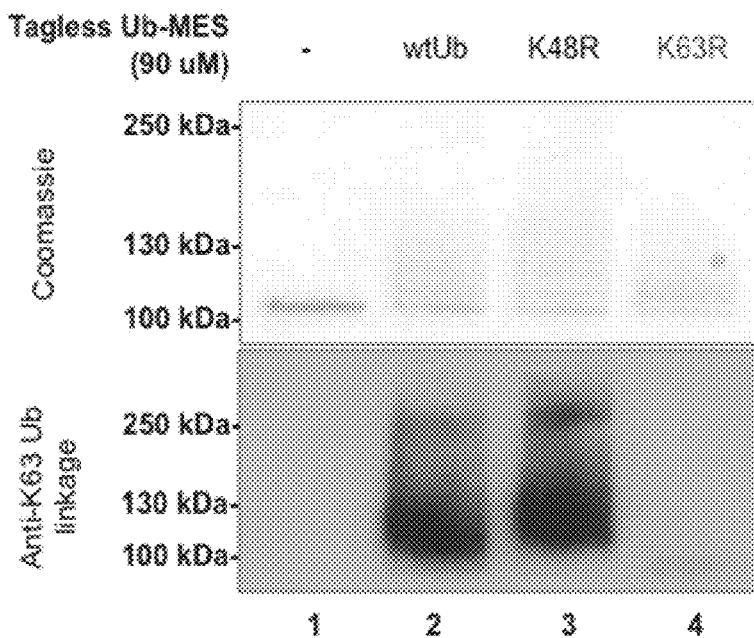

Rsp5ΔWW was used for these experiments because it was more active in autoubiquitination assays compared to the full length Rsp5, therefore polyubiquitin chains could be formed more efficiently. However, we have made similar observations for the full length Rsp5/ByS, suggesting that WW domains of Rsp5 are not critical for the assembly of polyubiquitin chains with specific linkages in ByS reaction conditions (FIG. 17).

Figure 18D:
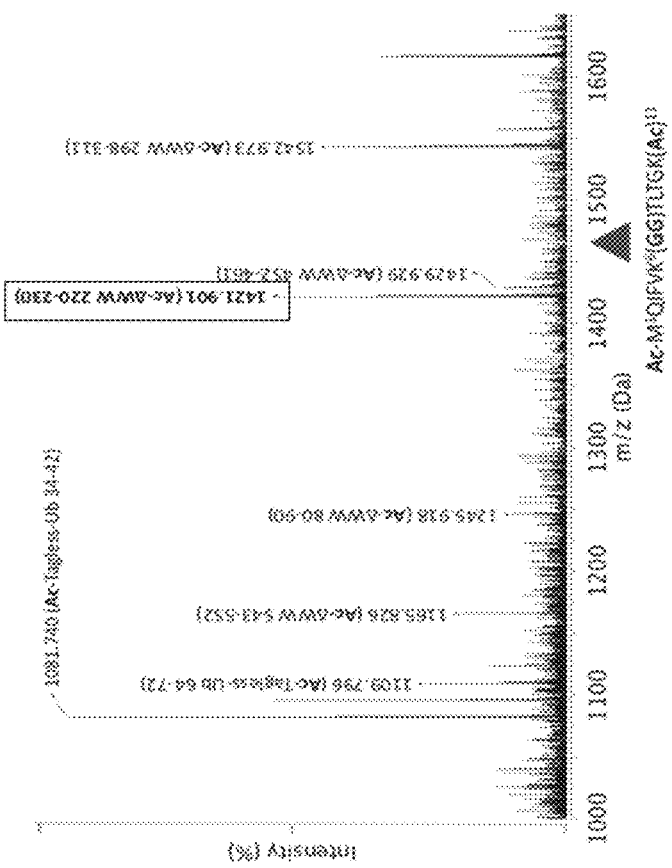
Figure 18C:
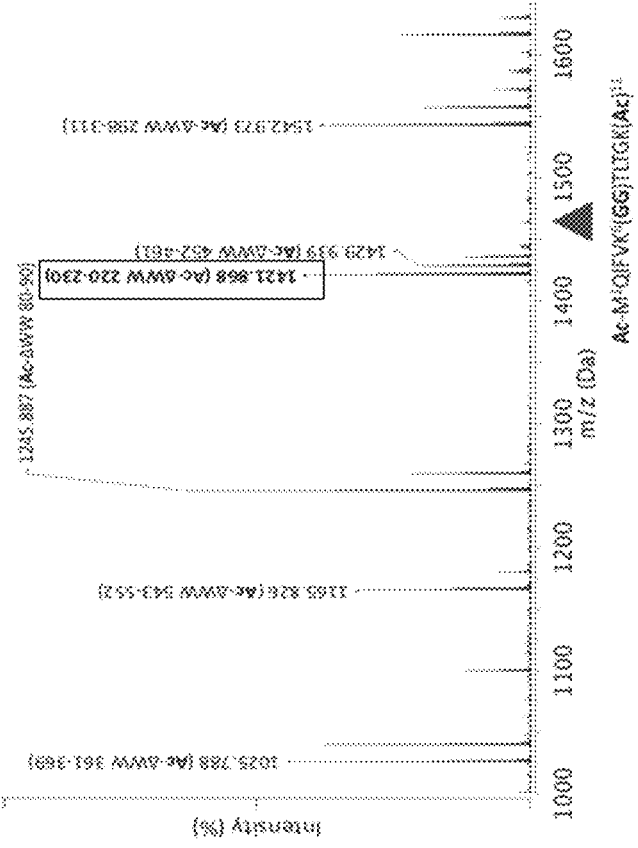
Figure 19A:
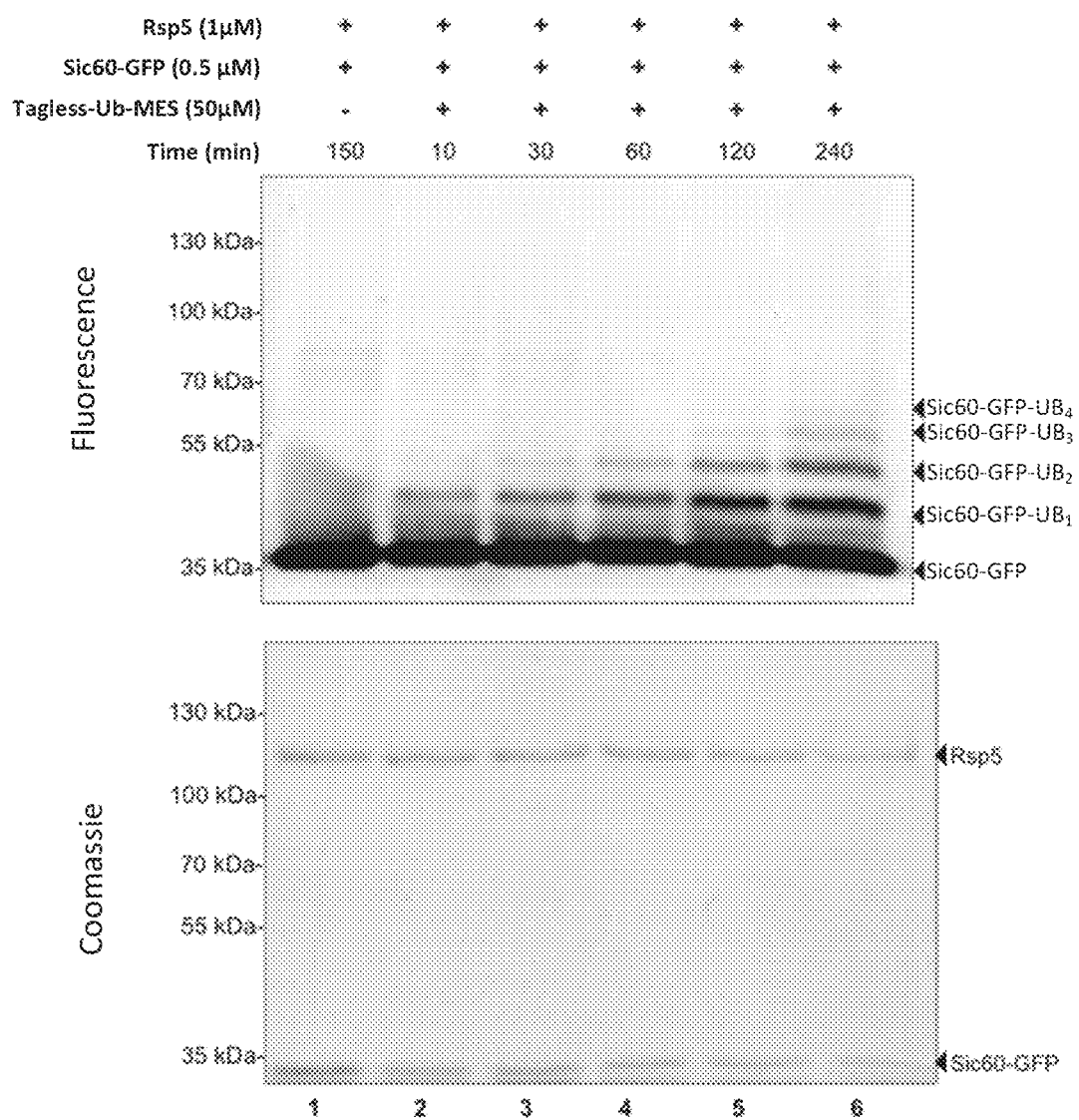
FIG. 19A-19E shows protein ubiquitination via Rsp5/ByS with Tagless-Ub-MES. Reaction mixtures containing indicated proteins in Ubiquitination Buffer I were treated with Tagless-Ub-MES to initiate the reaction. Reaction mixtures were incubated at room temperature for indicated times. Reactions were terminated with 6× Laemmli buffer, resolved by 7.5% SDS-PAGE gel and imaged by in-gel fluorescence scanning.
Figures 19B, 19C:
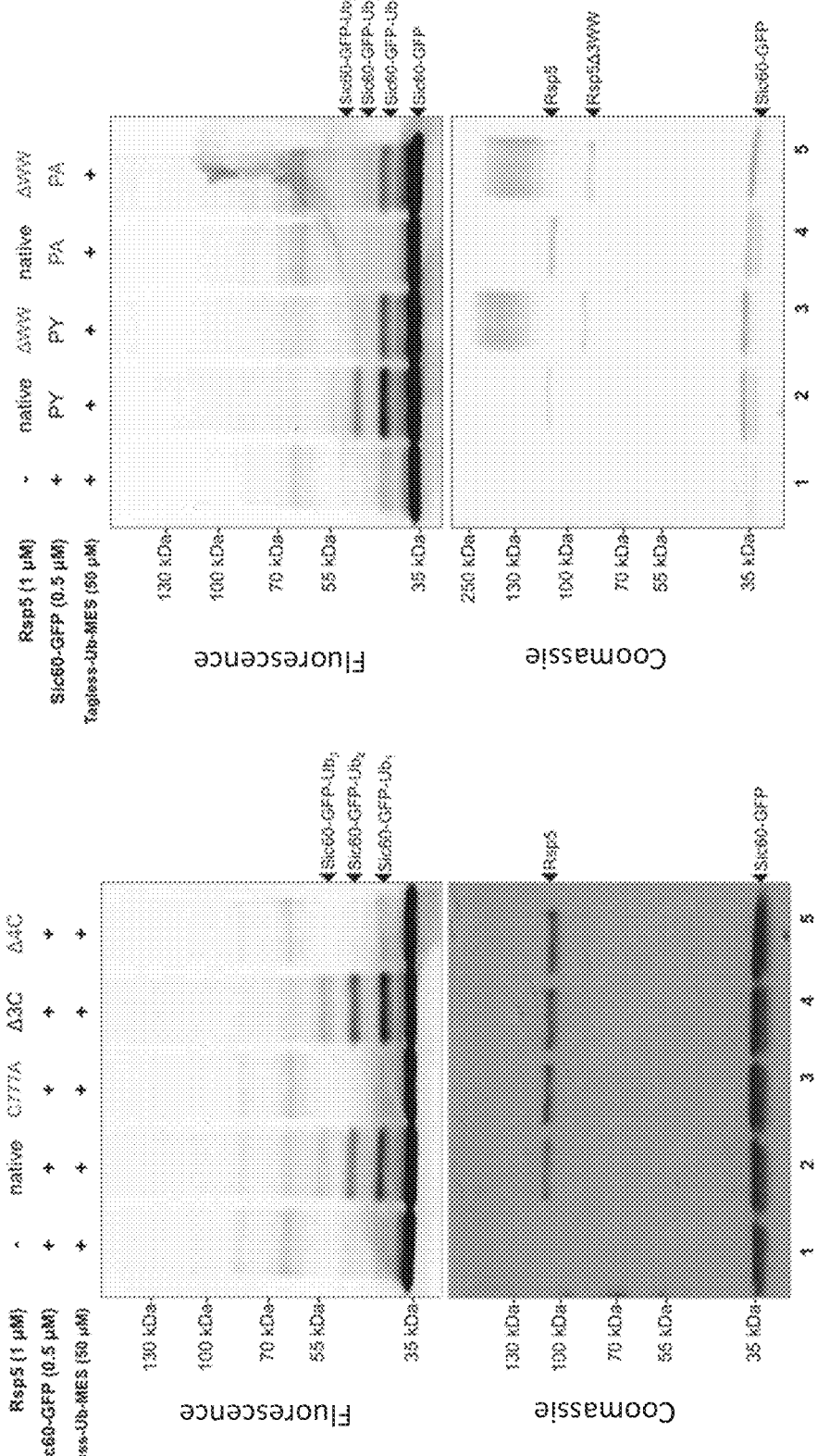
Figure 19E:
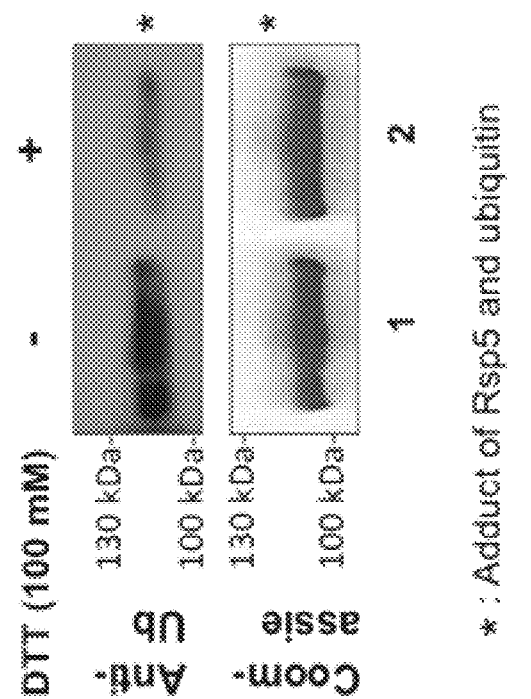
Figure 19D:
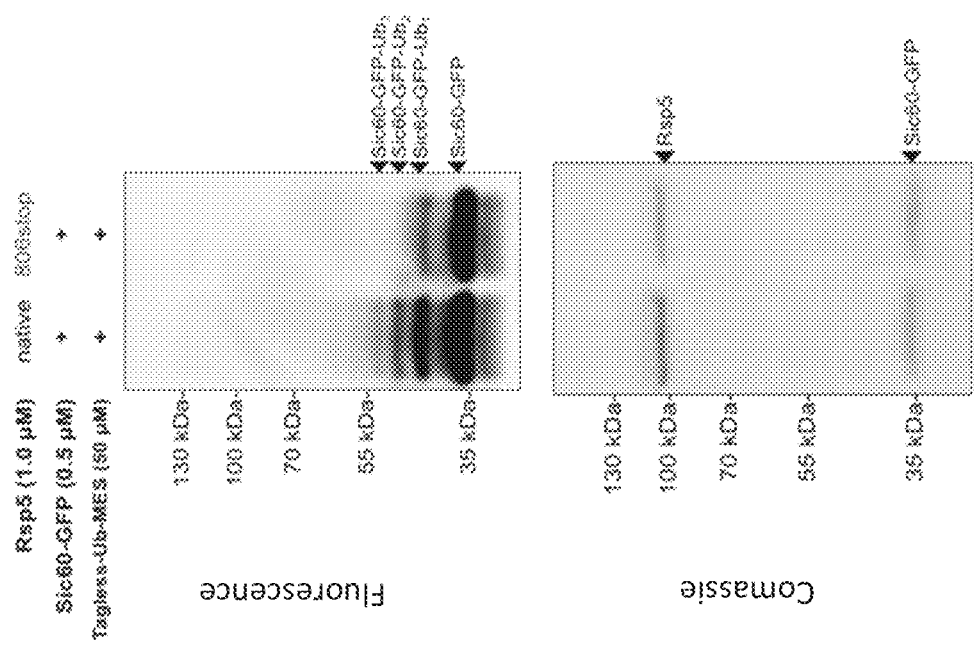
Figure 20A:
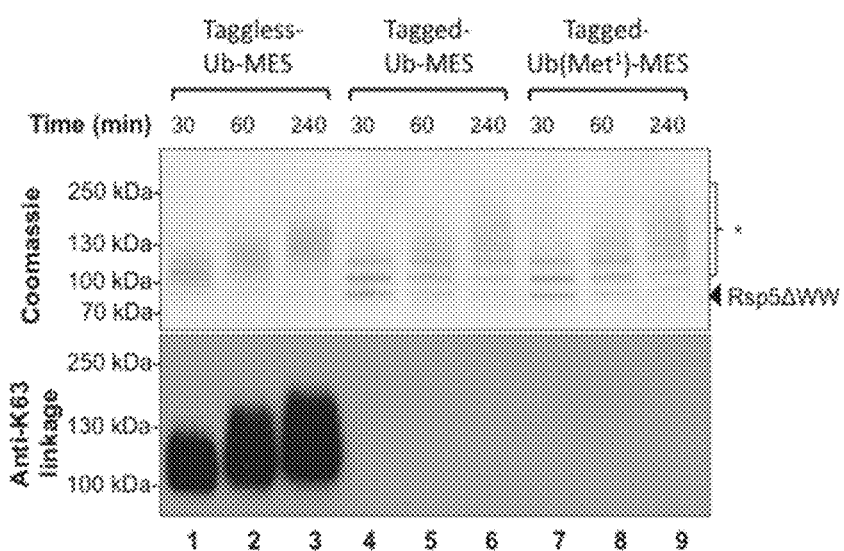
FIG. 20A-20D shows tagged-Ub(Met$^1$)-MES forms lower amount of K-63 linked polyubiquitin chains. Polyubiquitinated Rsp5ΔWW was prepared as in FIG. 3A-3B.
Figure 20B:
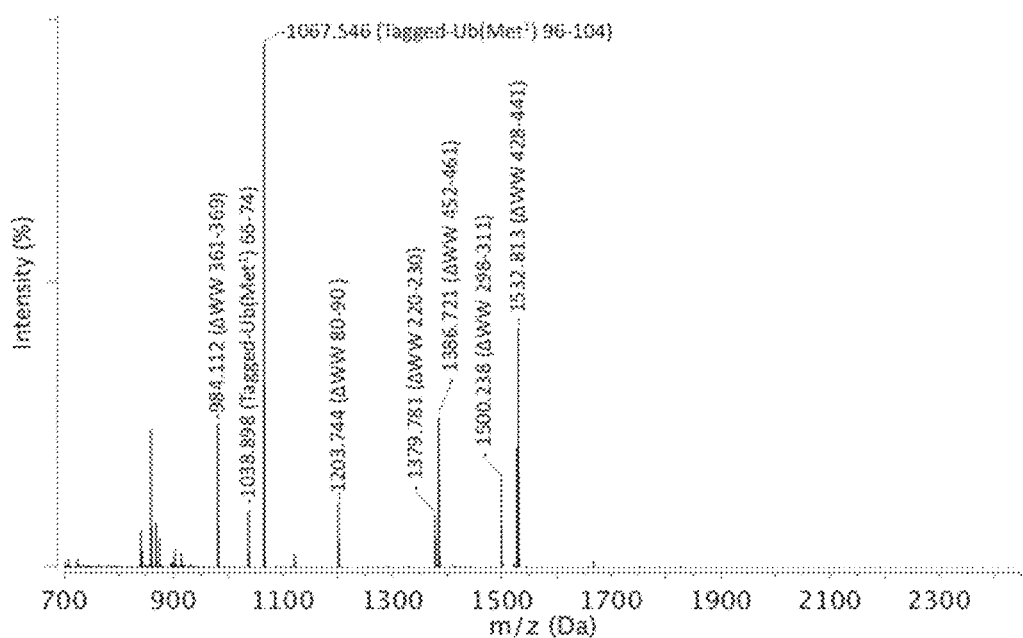
Figure 20C:
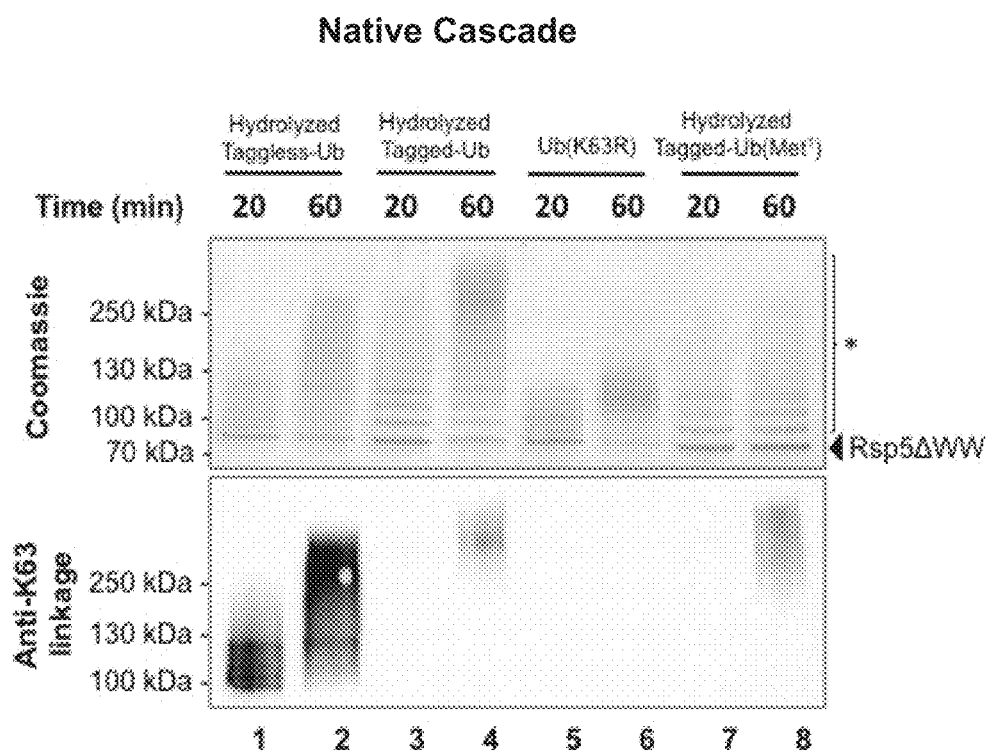
Figure 20D:
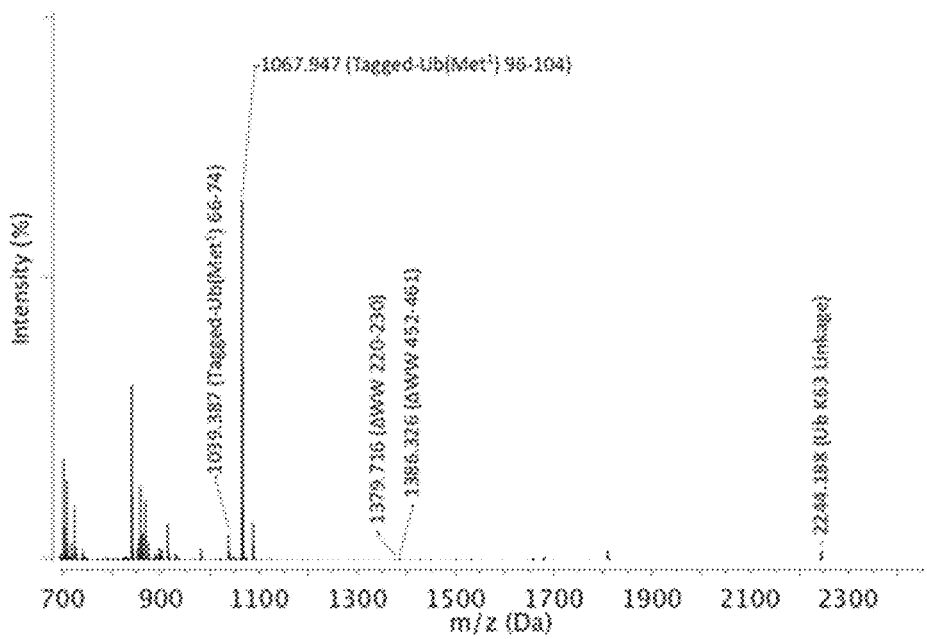

Analysis of the experimental data indicated that one of the tryptic peptides from Rsp5ΔWW(e.g., $^{220}$QYSSFEDQYGR$^{230}$, m/z=1379.402, FIG. 4B, FIG. 27C) and a K6-linkage peptide of polyubiquitin chain (e.g., $^{1}$MQIFVK$^{6}$(GG)TLTGK$^{11}$, m/z=1379.677, FIG. 28B) have very similar m/z ratios, and thus it was difficult to distinguish between these peptides in our MALDI-TOF experiments. To resolve this issue, the tryptic peptides of Rsp5ΔWW and lane 4 were acetylated with acetic anhydride and analyzed by MALDI-TOF (FIGS. 18C and D, FIG. 31). The tryptic peptide of Rsp5ΔWW has only one free amine at the N-terminus, whereas that of K6-linked polyubiquitin chain has both an N-terminal amine and a C-terminal lysine. MALDI-TOF analysis of acetylated tryptic peptides of both Rsp5ΔWW (FIG. 18C) and polyubiquitin chain formed by Rsp5/ByS with Tagless-Ub-MES (FIG. 18D) showed the signal that corresponds to singly acetylated peptide of Rsp5ΔWW (Ac-$^{220}$QYSSFEDQYGR$^{230}$, calculated average m/z=1421.424), but did not produce a signal for the doubly acetylated K6-linkage Ub peptide (Ac-MQIFVK$^{6}$(GG)TLTGK(Ac)$^{11}$, calculated average m/z=1464.464). Furthermore, signal from the $^{220}$QYSSFEDQYGR$^{230}$ peptide was accompanied by another signal from Rsp5 peptide that corresponds to $^{452}$EYVELYTQWR$^{461}$ (calculated average m/z=1386.6688).

Figure 17B:
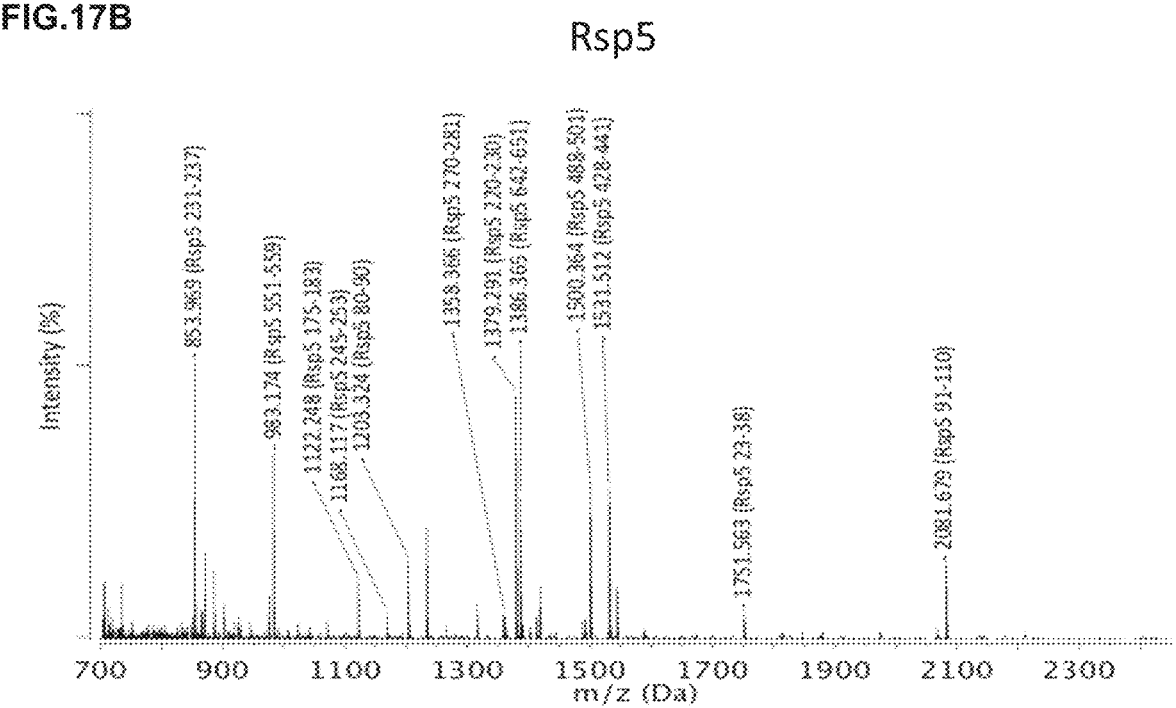
Figure 17E:
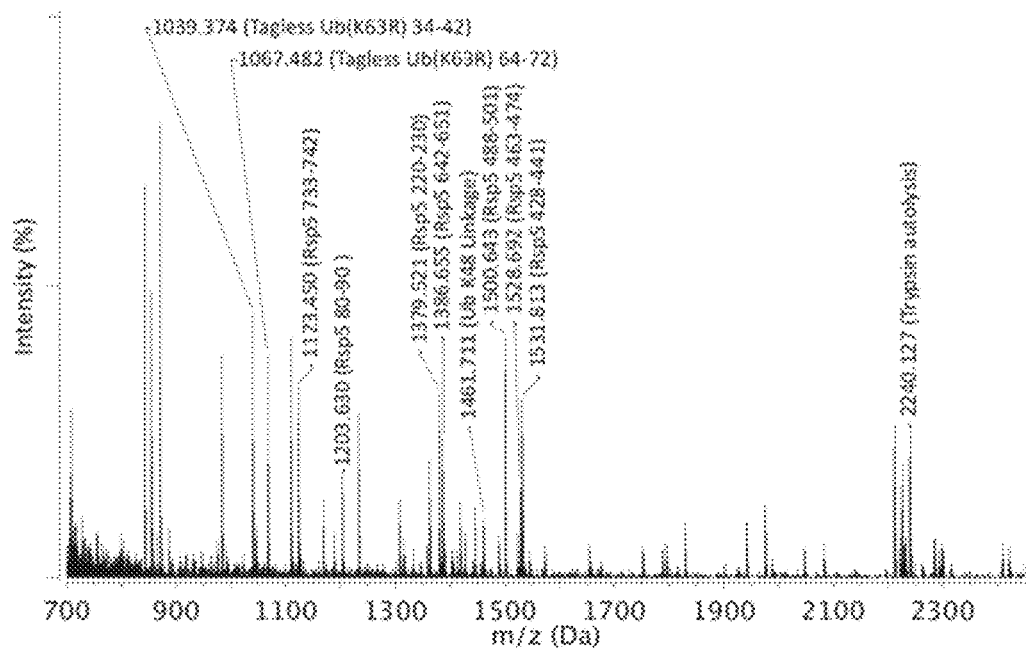

The signal ratio for these peptides was the same for both Rsp5 and Rsp5ΔWW in all MALDI experiments even without ubiquitination (FIGS. 17B and 18A). This further suggests that both of these peptides originate from the same protein sample, e.g., Rsp5 or Rsp5ΔWW. These observations coupled with the peptide acetylation experiments indicated that the observed peptide signal with m/z=1379.290 (FIG. 4B) was a tryptic peptide derived from Rsp5ΔWW, and not from K6-linked polyubiquitin chain. Taken together, the data from these experiments indicated that Rsp5/ByS synthesizes K63-specific polyubiquitin chains in vitro in the absence of E1, E2, and ATP. Moreover, the experiments provide direct evidence that E2 enzymes are dispensable for the Rsp5 catalyzed Ub-Ub isopeptide bond formation with K63 specificity in vitro.

Example 5

N-Terminal Tags in Ub-MES Inhibit Polyubiquitin Chain Synthesis by Rsp5 in Both ByS and Native Ubiquitination Reactions During the development of embodiments of the technology provided herein, data were collected that indicated that the N-terminally modified Ub-MES (Tagged-Ub-MES, FIG. 27) interfered with the formation of K63-linked polyubiquitin chains by Rsp5 both under ByS and the native cascade conditions (FIG. 5). To test the effect of N-terminal tag on the polyubiquitin chain synthesis, experiments were conducted in which Tagged- and Tagless-Ub were prepared by basic hydrolysis of the corresponding Ub-MES thioesters as previously described.[32] Subsequently, the Tagged-Ub and Tagless-Ub constructs were purified and used in autoubiquitination reactions under the native ubiquitination conditions with E1, E2, Rsp5ΔWW, and ATP. The incubation time of each reaction was controlled to produce similar amount of higher molecular weight bands, as judged by Coomassie staining. Then, the formation of K63-linked polyubiquitin chains was examined with K63-linkage specific antibodies. The western blotting experiments demonstrated that Tagged-Ub and Tagged-Ub-MES significantly interfered with the formation of K63-linked polyubiquitin chains, under both native ubiquitination cascade and ByS reaction conditions (FIG. 5A). Tagless-Ub did not interfere with the formation of K63-linked polyubiquitin chains, indicating that the reaction conditions for the hydrolysis of Tagged-Ub-MES thioester are not the contributing factor to the inactivity of the prepared Tagged-Ub in the polyubiquitin chain formation reaction.

To further validate these observations, the gel region between 100 kDa to 250 kDa (FIG. 5A, lane 3, 6, 9 and 12) from the native and ByS ubiquitination reactions was excised, digested by trypsin, and analyzed by MALDI-TOF (FIG. 5B-E). As shown by the data, the m/z signal corresponding to K63-linkage was significantly diminished when Tagged-Ub or Tagged-Ub-MES was used in native or ByS reaction conditions. Further, the MALDI-TOF data did not indicate that there were any dominant Ub-linkages in the case of Tagged-Ub or Tagged-Ub-MES, indicating that the N-terminal modification of Tagged-Ub construct may stimulate non-specific multi-ubiquitination (FIG. 32B). Other than polyubiquitin chain synthesis, Tagless-Ub-MES displayed biochemical properties identical to those of Tagged-Ub-MES in ByS conditions (FIG. 19).

The original Tagged-Ub-MES construct comprises a 3× FLAG-6× His tag immediately followed by $Glu^2$ of ubiquitin (FIG. 27); therefore, $Met^1$ of ubiquitin is replaced with a histidine residue. $Met^1$ of ubiquitin is proximal to $Lys^{63}$ of ubiquitin (~7Å), which in turn is close to the negatively charged $Glu^{64}$ residue.[33] Thus, in the Tagged-Ub-MES constructs hydrophobic methionine side chain is replaced with the polar histidine side chain, which may lead to the inhibition of the isopeptide bond ligation via $Lys^{63}$. Without being bound by theory, other possible reasons for the inhibition of K63-linked polyubiquitin chain formation may include physical obstruction between N-terminal tag of the ubiquitin and the ubiquitin binding to the C- or N-lobe of HECT E3.

Thus, to test if the lack of $Met^1$ in Tagged-Ub-MES is responsible for the inhibition of polyubiquitin chain formation, a Tagged-Ub($Met^1$)-MES was prepared that has $Met^1$ inserted after the N-terminal tag. The data indicated that the absence of $Met^1$ was not a major contributor to the observed inhibition of polyubiquitin chain synthesis. Even after the insertion of $Met^1$, N-terminal tag on the ubiquitin causes significant inhibition of K63-linked polyubiquitin chains in both ByS and native cascade (FIG. 20). Taken together, the experiments indicated that N-terminal 3× FLAG-6× His tag on the ubiquitin inhibits the formation of K-63 linked polyubiquitin chains in bypassing and in native ubiquitination systems. Thus, these observations indicate that N-terminal tag in Tagged-Ub-MES interferes with K-63 polyubiquitin chain formation in the native and bypassing systems Overall, these data indicate that caution has to be exercised when conducting cell-based transfection experiments with N-terminally modified ubiquitin. Based on the in vitro experiments, N-terminal ubiquitin modifications may interfere with the formation of polyubiquitin chains and lead to non-specific multi-ubiquitination of intracellular proteins, which may lead to different cellular phenotypes. Although the inhibition of protein turnover both in vivo and in vitro by N-terminally tagged ubiquitin has described before,[34] the technology provided herein is novel in unambiguously demonstrating that N-terminal modification of ubiquitin inhibits K63-specific chain formation by HECT E3s in vitro.

Further, even though N-terminal tag of Ub-MES inhibits polyubiquitin chain formation reactions, it is still active in substrate ubiquitination and autoubiquitination assays. This indicates that embodiments of the provided Ub~MES probes may comprise fluorescent labels, biotin, or other tags at the N-terminus and provide compositions suitable for assay development and proteomic study purposes.

Example 6

Comparison of ByS System With the Native Ubiquitination System

Figure 21:
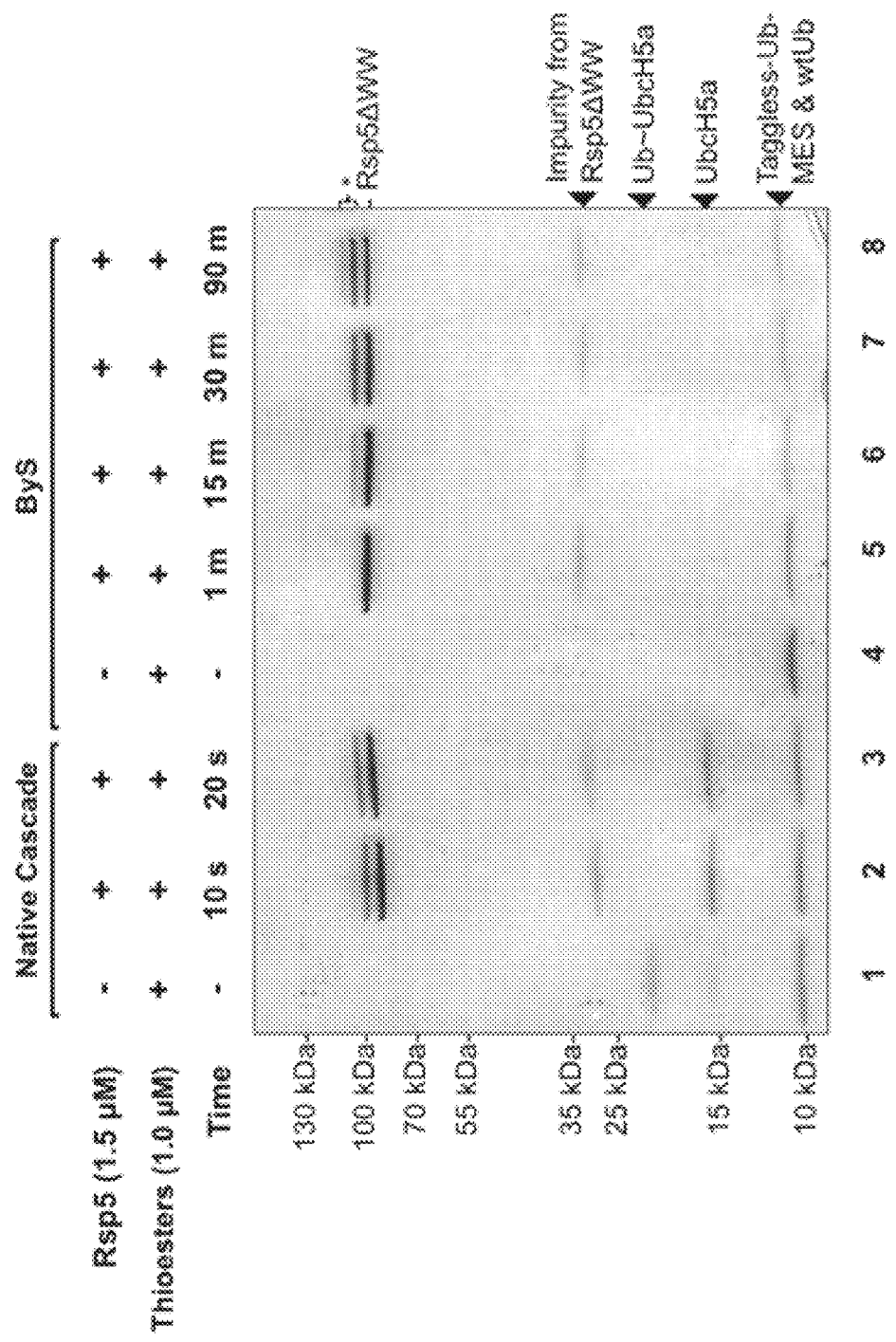
FIG. 21 shows comparison of the ubiquitination efficiency in ByS and native systems using pulse-chase experiments. Ub~UbcH5a or Tagless-Ub-MES in ubiquitination buffer II were treated with Rsp5ΔWW to initiate ubiquitination reactions, and incubated at room temperature for indicated times, followed by quenching with 6× non-reducing Laemmli loading buffer. Reaction mixtures were resolved by SDS-PACE (4-20% gel) and the amount of ubiquitinated proteins as well as unreacted thioesters were visualized with Coomassie staining. Procedure: 10 μL of solution of UbcH5a~Ub (2.0 μM) or Tagless-Ub-MES (2.0 μM) in ubiquitination buffer II was treated with 10 μL of Rsp5ΔWW (3.0 μM) in ubiquitination buffer II to initiate reaction. Bands corresponding to ubiquitinated Rsp5ΔWW is marked with "*". UbcH5a~Ub preparation is described herein.
Figure 22:
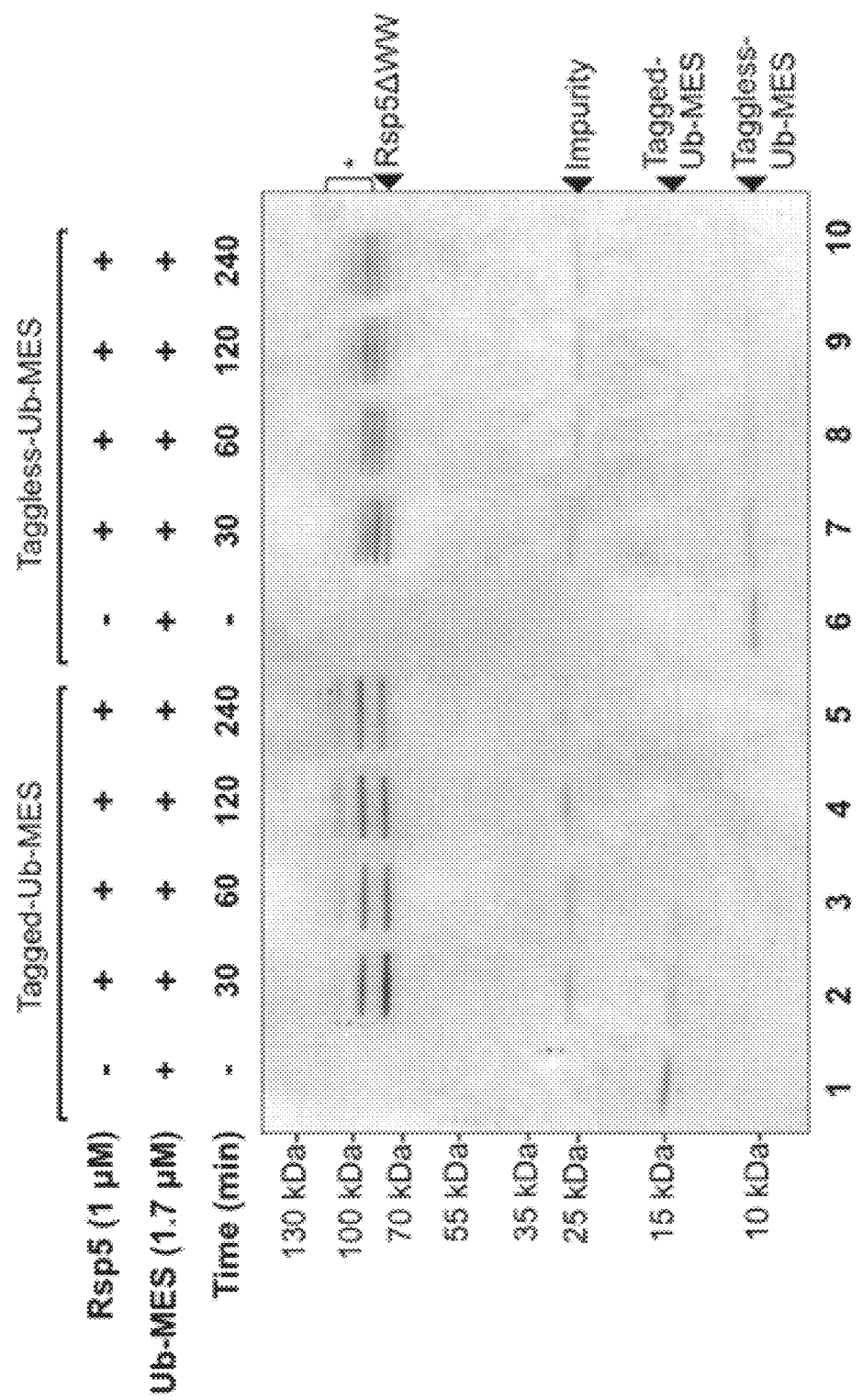
FIG. 22 shows Rsp5 autoubiquitination with Tagged- and Tagless-Ub-MES. The solution of Tagged- and Tagless-Ub-MES was treated with Rsp5ΔWW to initiate the reaction. The reaction mixture was incubated at room temperature for indicated times, quenched with 6× non-reducing Laemmli buffer, resolved by SDS-PAGE (4-20% gel) and the amount of ubiquitinated proteins along with unreacted thioesters imaged by Coomassie staining The band corresponding to ubiquitinated Rsp5ΔWW is marked with "*".

Next, during the development of embodiments of the technology provided herein, experiments were conducted to compare the ubiquitination efficiency of the native system and ByS system. Since in the ByS system E2~Ub thioester is replaced with Ub~MES thioester, it was expected that Ub~MES will have much lower binding affinity to Rsp5, and perhaps slower transthiolation kinetics, which overall will contribute to the lower ubiquitination efficiency of the ByS. To conduct a direct comparison, pulse-chase experiments conducted,[26] and the consumption of Ub~UbcH5a and Tagless-Ub-MES thioesters, which are direct substrates of Rsp5ΔWW in the native and ByS systems, respectively, was monitored (FIG. 21). The observations indicated that a native cascade is more efficient at protein ubiquitination than the ByS system. Also observed was complete consumption of Ub~UbcH5a thioester after 10 seconds of the reaction time, while Tagless-UbMES was not consumed after 90 minutes. Similarly, the formation of monoubiquitinated Rsp5 was observed after 10 seconds in the native system, yet in the bypassing system monoubiquitinated Rsp5 was not observed at 1 minute of reaction time as judged by coomassie staining. In addition, since earlier it was found that the N-terminal tag of the ubiquitin inhibits the formation of K-63 linked polyubiquitin chains, experiments were conducted to assess if the same N-terminal tag affects the activity of Tagged- and Taggless-Ub-MES probes in autoubiquitination assays with Rsp5 ΔWW (FIG. 22). To analyse the ubiquitination efficiency, consumption of Tagless- and Tagged-Ub-MES by Rsp5ΔWW in the ByS system was monitored. Both thioesters were consumed after 60 minutes as judged by Coomassie. In the case of Tagged-Ub-MES, a major band of monoubiquitinated Rsp5 ΔWW was formed; in the case of Tagless-Ub-MES, multi- and poly-ubiquitinated forms of Rsp5 were observed. This is perhaps related with the fact that N-terminal tag in Tagged-Ub-MES inhibits polyubiquitin chain synthesis. Without being bound by theory, it is noted, however, that Tagged- and Taggless-Ub-MES thioesters usually contain some amount of Tagged-Ub and Tagless-Ub that originate from the residual hydrolysis of thioesters during their preparation. Hydrolyzed products are more difficult to separate from the ubiquitin thioesters with conventional HPLC methods. It therefore is not possible to exclude a model in which hydrolyzed products act as non-productive competitors in the system, which may make precise kinetic studies difficult.

Example 7

Kinetic Characterization of the Bypassing System

During the development of embodiments of the technology provided herein, experiments were conducted to assess enzymatic activity of HECT E3s in ByS quantitatively. In particular, a robust protocol was used to quantify the remaining amount of Ub-MES using fluorescein labeled cysteine (FCys, Scheme S1). It was contemplated that FCys undergoes a native chemical ligation reaction with the residual Ub-MES and the amount of the fluorescently labelled ubiquitin correlates with the amount of residual in the reaction mixture (FIG. 6A).[35,36]

In some embodiments, a typical protocol includes the addition of 2× FCys stop buffer that contains Urea (10 M) and FCys (2 mM) to the bypassing system reaction mixture, followed by incubation for 16 hours at 37° C. In the absence of Rsp5ΔWW, the amount of Tagless-Ub-MES did not change over 120 minutes (FIG. 6B, top).

Figure 23A:
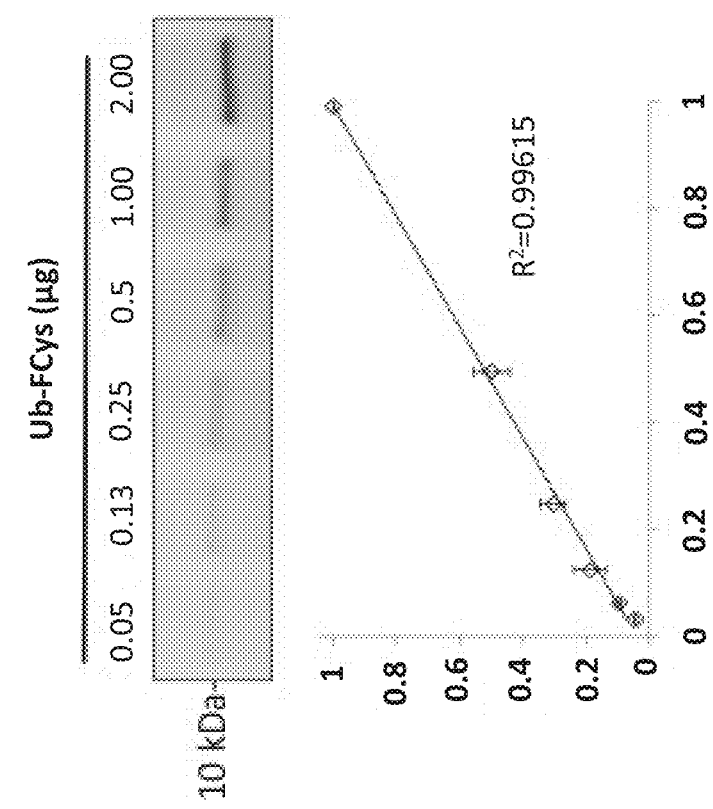
FIG. 23A-23B shows (FIG. 23A) MS analysis of ligation product between Tagless-Ub-MES and FCys. The Tagless-Ub-MES (100 μM) was treated with 2× FCys stop buffer for 16 hours. The reaction was desalted using Zeba spin column and the eluate was analyzed by ESI-MS. Although we observed the disulfide adduct at m/z 9650.51, the reducing SDS loading buffer contains DTT, which cleaves disulfide bond.
Figure 23B:
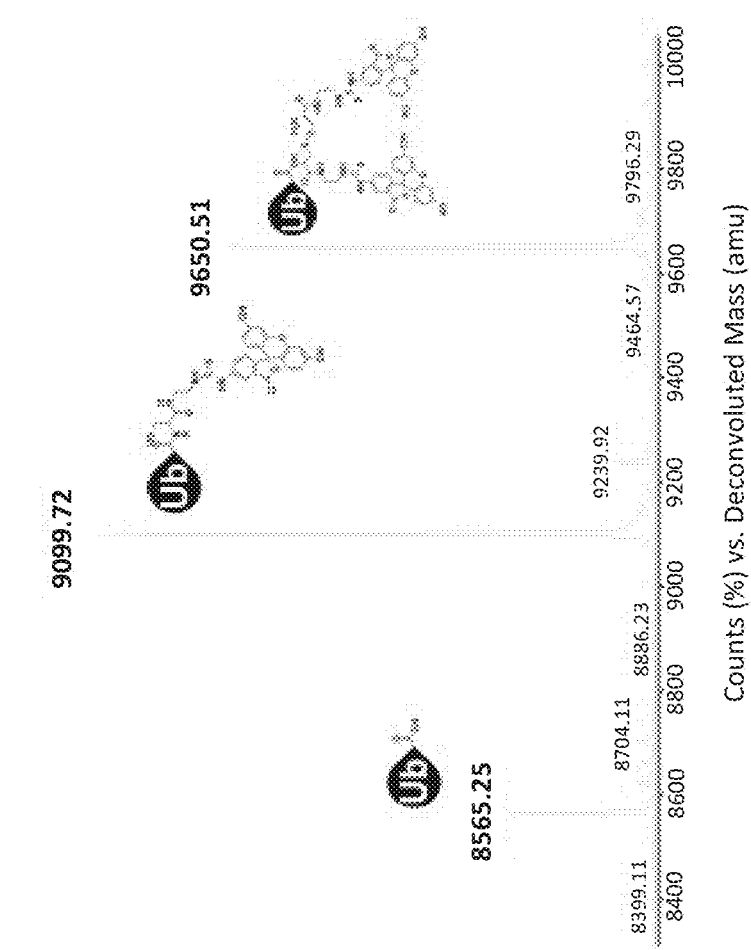
Figure 24A:
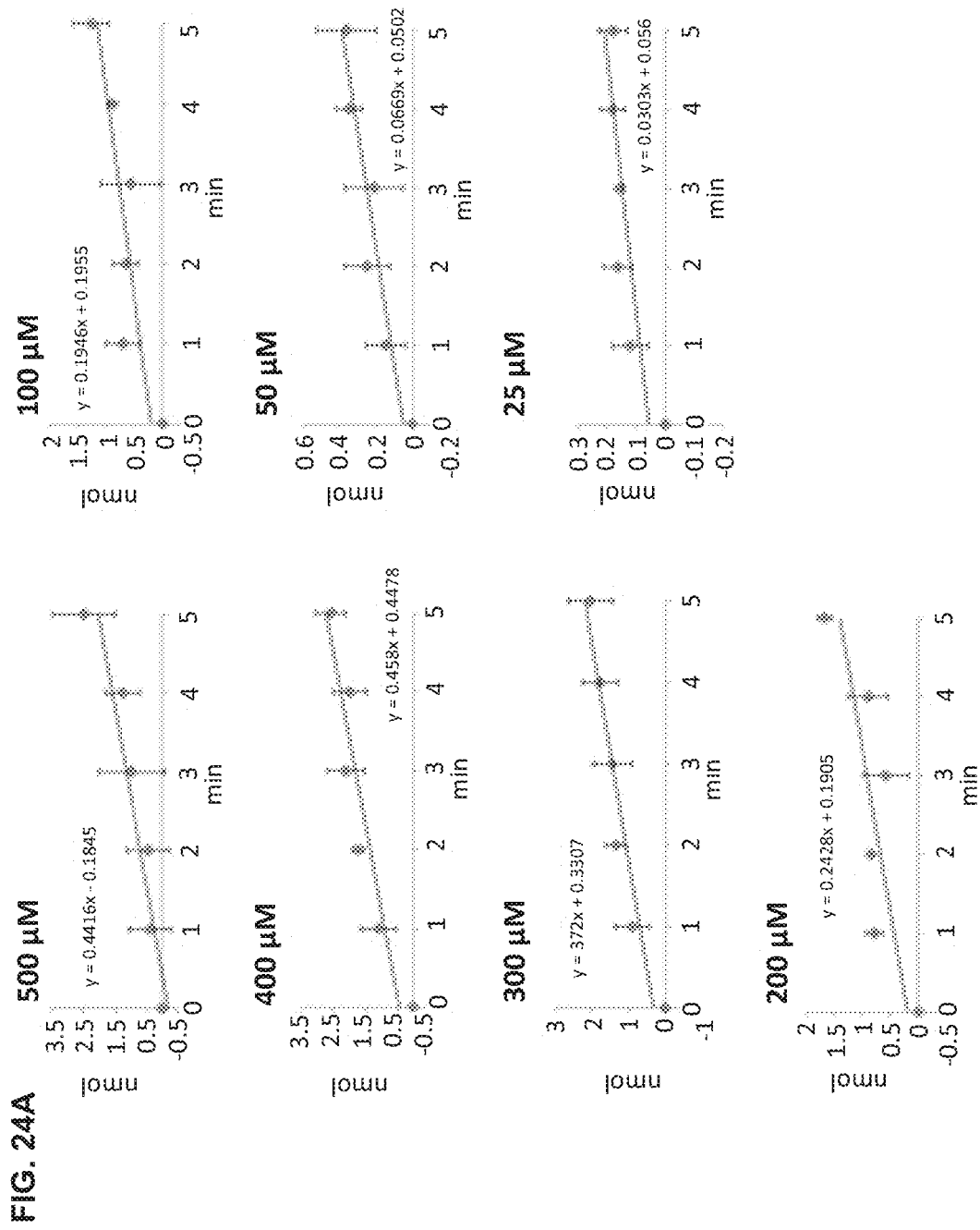
FIG. 24A-24B shows initial rates of reactions at different concentration of Ub-MES and Rsp5ΔWW.
Figure 24B:
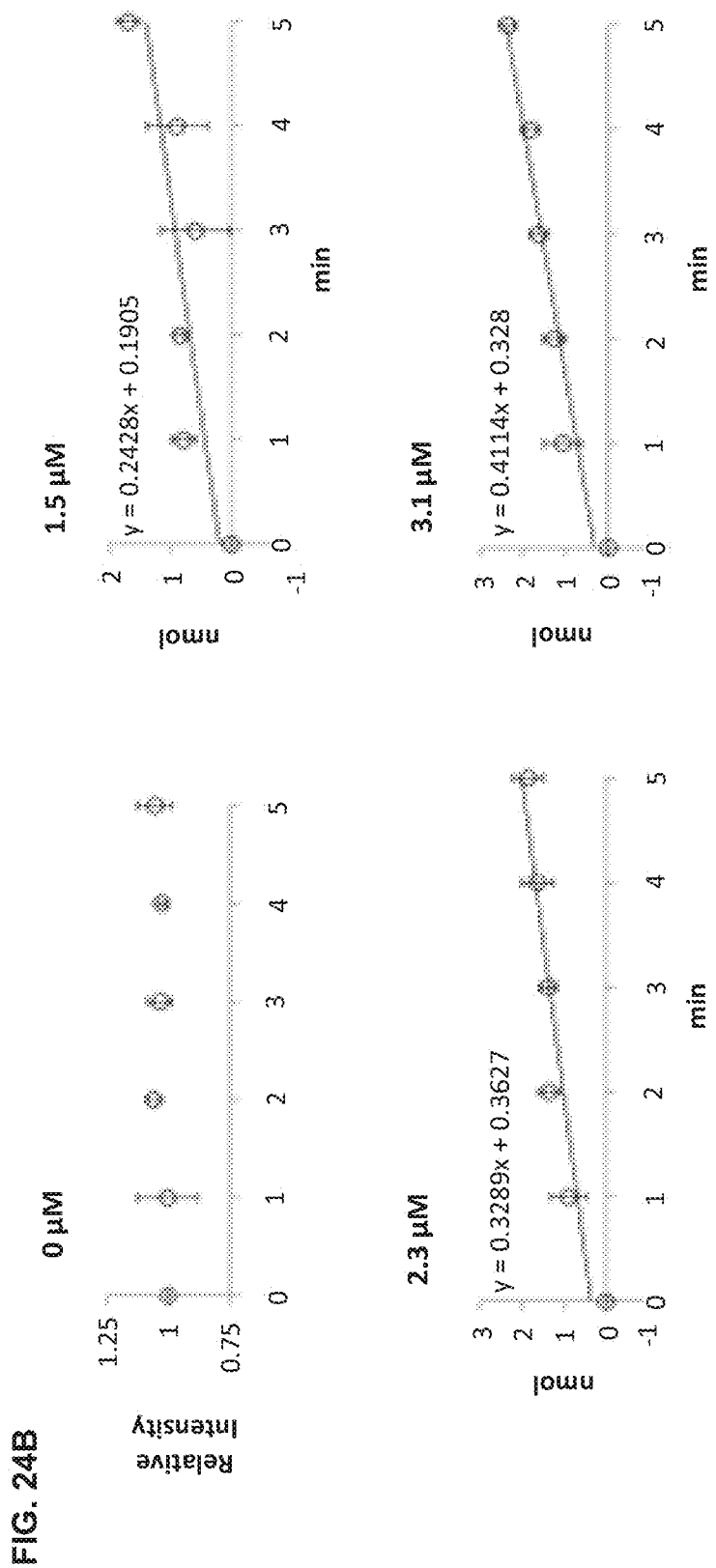

Experiments confirmed that under these reaction conditions the conjugation reaction yields Tagless-Ub-FCys by MS analysis (FIG. 23A). It was also observed that the fluorescence intensity of Tagless-Ub-FCys displayed linear correlation to the loading amount of Tagless-Ub-MES over a wide range of loading amounts (50 ng-2.0 μg, FIG. 23B). In the presence of Rsp5ΔWW, however, the amount of Tagless-Ub-MES was decreasing over time (FIGS. 6B and 6C) The initial reaction rates (0-5 min) of the Tagless-Ub-MES consumption by Rsp5 were measured at different concentrations of Tagless-Ub-MES or Rsp5, which indicated that the initial reaction rates depend on Tagless-Ub-MES and Rsp5 concentration with $k_{cat}$ and $K_m$ values of 0.491±0.089 $s^{-1}$ and 553.1±223 μM, respectively (FIG. 6D and FIG. 24).

Notably, the $k_{cat}$ and $K_m$ for Rsp5 were obtained using surrogate substrate Tagless-Ub-MES, and thus these reaction constants do not reflect $k_{cat}$ of Rsp5 in the native ubiquitination cascade. In the native cascade, E2~Ub is the direct substrate for Rsp5, which leads to higher ubiquitination efficiency due to the higher binding affinity of E2~Ub and optimized alignment and charge/electron distribution of reactive atoms for subsequent transthiolation reaction. Therefore, under the assumption that $k_{cat}$ of Rsp5 represents the efficiency of catalysis encompassing tranthiolation as well as isopeptide ligation steps, these values do not accurately represent the $k_{cat}$ values of Rsp5 in the native cascade.

Further, the developed assay measures the gross consumption of Ub-MES over time by Rsp5. In this reaction setup, each enzymatic turnover will generate multiple enzymatically active autoubiquitinated forms of Rsp5. Therefore, the obtained $k_{cat}$ and $K_m$ are collective values representing different Rsp5-Ub$_x$ variants.

Nevertheless, the developed protocol is particularly useful for quantitative assessment of the catalytic activity of HECT E3s by obtaining the surrogate $k_{cat}$ and $K_m$ values. For example, the relative effect of HECT E3 inhibitors/activators or point mutations that cripple transthiolation/isopeptide ligation steps can be easily monitored and compared with the developed protocol. Taken together, the introduced protocol using Ub-MES and FCys is useful for biochemical and drug discovery purposes.

Example 8

Naturally Occurring Small Molecule Thiols Can Replace E2 Enzymes in the Native E1→E2→E3 Ubiquitination Cascade In Vitro Data collected during the development of the technology described herein indicated that C-terminal ubiquitin thioesters such as Ub-MES directly react with Rsp5 in vitro. Thus, experiments were conducted to test these types of chemical reactions under physiological conditions. Earlier reports suggested that dithiothreitol (DTT) can undergo a transthiolation reaction with E1~Ub thioesters, producing C-terminal Ub~DTT thioester,[37,38] As such, experiments were conducted to test small molecule thiols, including naturally occurring thiol glutathione, as substitutes for E2 enzymes in the E1→E2→HECT E3 ubiquitination cascade and to assess the efficiency of HECT E3 autoubiquitination. The intracellular milieu contains high concentration of glutathione (0.5 to 10 mM).[39] Therefore, it was contemplated that the ubiquitin C-terminal glutathione (Ub~GSH) thioesters present inside cells may be ligated to proteins by E3 ligases that have catalytic cysteines, such as HECT E3 and RBR E3 ligases.

Experimental data collected indicated that treatment of E1, Rsp5ΔWW, ubiquitin, and ATP with small molecule thiols led to autoubiquitination of Rsp5ΔWW after 2 hours of reaction time (FIG. 7A). Autoubiquitination of Rsp5ΔWW was not observed in the absence of E2 enzyme or small molecule thiols, and dependended on the thiol concentration (FIG. 7A).

Taken together, these results indicate that the alternative, non-canonical ubiquitination cascade exists under physiological conditions. In this case, E1~Ub thioesters react with small molecule thiols such as glutathione (GSH) to undergo a transthiolation reaction, producing reactive C-terminal Ub~GSH thioesters that then react with downstream E3s containing catalytic cysteine leading to substrate ubiquitination (FIG. 7B).

Further, without being constrained by theory, it is contemplated that GSH mediated ubiquitination is controlled in cells by a system in which ubiquitin C-terminal hydrolases (UCHs) hydrolyze Ub-GSH thioesters to regenerate a free pool of ubiquitin and prevent uncontrolled protein ubiquitination. Indeed, it has been shown previously that UCHs hydrolyze C-terminal esters, amides, and thioesters of ubiquitin.[37,38,40] Also, recent reports demonstrate that the UCHs are implicated in many human diseases. As such, additional functions of UCHs may involve preventing non-specific protein ubiquitination.[41,42,43]

Example 9

ByS as a Platform for Fluorescent Assays to Screen for E3 Ubiquitin Ligases

According to the technology provided herein, one significant advantage offered by the "bypassing system" is providing fluorescent assays to screen for modulators (e.g., inhibitors or activators) of E3 ubiquitin ligases that have catalytic cysteines. Current approaches to screen for inhibitors of E3 ubiquitin ligases require ATP, ubiquitin, E1, E2, and E3 enzymes. Subsequently, the enzymatic activity of E3 ligase is detected by quantifying the amount of autoubiquitinated E3 with Tandem Ubiquitin Binding Entity that contains a fluorophore or with antibodies that bind polyubiquitin chains. Additional steps may include purification of autoubiqutinated E3s, which adds further complexity to the assay. Sometimes, FRET techniques are used in which antibody with FRET donor binds the epitope in E3 ligases, while the antibody with FRET acceptor binds to polyubiquitin chains or E3s. Overall, current assays have the following drawbacks:
1) They are very expensive because they require E1, E2, and E3 enzymes;
2) They produce significant numbers of false positives because the decrease in the autoubiquitination of E3s can result from the off-target inhibition of E1 or E2 enzymes by a small molecule. Therefore, when large number of small molecules is screened, a lot of secondary validation assays need to be conducted thus increasing the time and cost.
3) Once inhibitor of E3 is identified it is difficult to conduct subsequent SAR studies, because again structural analogues of the initial lead compound can produce off target effects by inhibiting E1 or E2 enzymes or respective E1~Ub, E2~Ub, and/or E3~Ub thioesters.
4) In contrast to kinase or other enzyme inhibitors, difficulties arise in quantitative kinetic characterization and establishing the mechanism of enzyme inhibition with identified leads, due to the presence of additional enzymes in the mixture. (FIG. 8).

Additional challenges include multiple wash steps that preclude the continuous, non-invasive monitoring of the enzymatic reaction. One current assay used by Progenra is outlined in FIG. 8.

In some embodiments, the technology provides technologies to quantify autoubiquitination of E3s (see, e.g., FIG. 9A). For example, the discovered reaction provides a unique opportunity to provide an assay for E3 ubiquitin ligases that have catalytic cysteines (this includes HECT E3s, Ring-Between-Ring E3s, and New E3 Ligases (NELs)). In the proposed approach, C-terminal ubiquitin thioester carries a fluorophore attached to the thioester ("UbiFlu" or "UbiFluor") (FIG. 9B). When the C-terminal ubiquitin thioester undergoes a transthiolation reaction with the catalytic cysteine of HECT E3, fluorophore is cleaved from the ubiquitin and released into the solution to form the catalytically active HECT E3~Ub thioester. During multiple enzymatic turnovers, more and more UbiFlu is consumed and more and more fluorescein released into the solution. Therefore the progress of the enzymatic reaction is monitored by measuring the decrease in the fluorescence of the UbiFlu, which reflects the consuption of UbiFlu. Such measurements are conducted, e.g., by in-gel fluorescent scanning.

An alternative method to detect the consumption of UbiFlu includes, e.g., a fluorescence polarization assay, since the molecular weight of the fluorophore changes significantly as fluorophore is cleaved from the high molecular weight ubiquitin. Such change in the molecular weight is detected with a fluorescent polarization assay. The proposed approach provides a number of experimental advantages that are outlined in FIG. 9C. Experiments conducted during the development of embodiments of the technology provided herein tested the UbiFlu reagent using Rsp5 as a model system.

Example 10

Preparation and Testing of UbiFlu

Figure 10A:
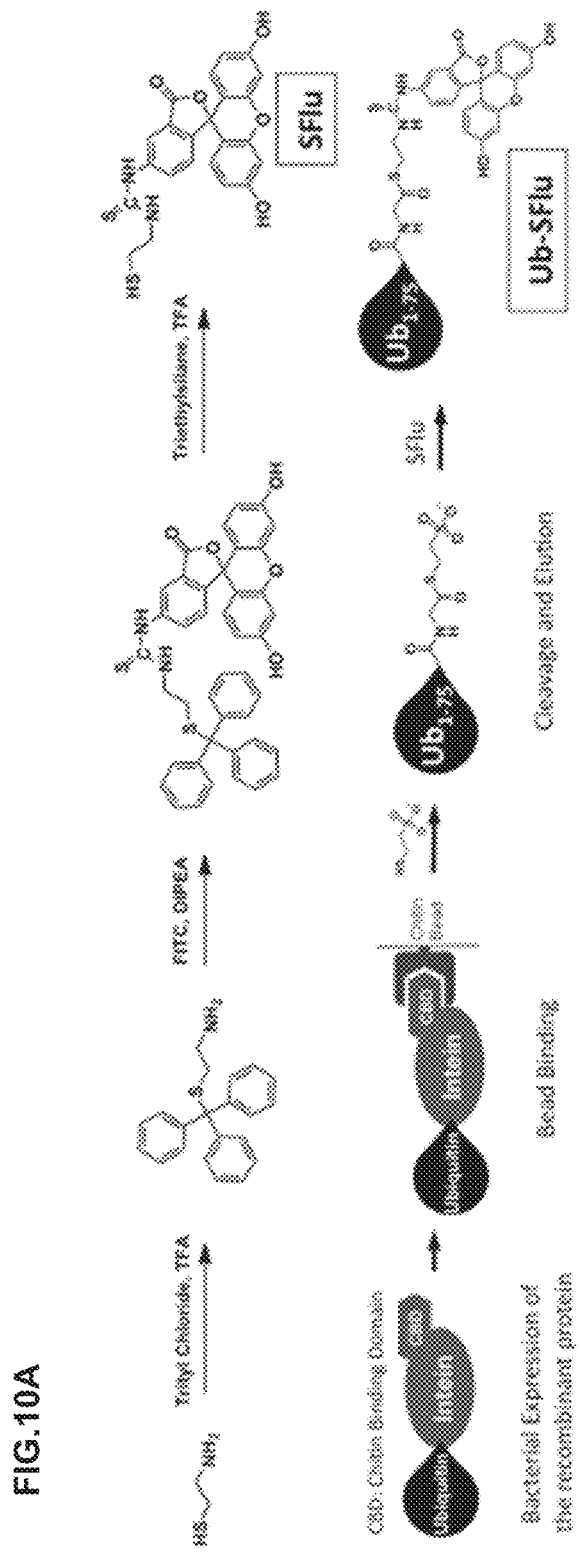
Figure 12A:
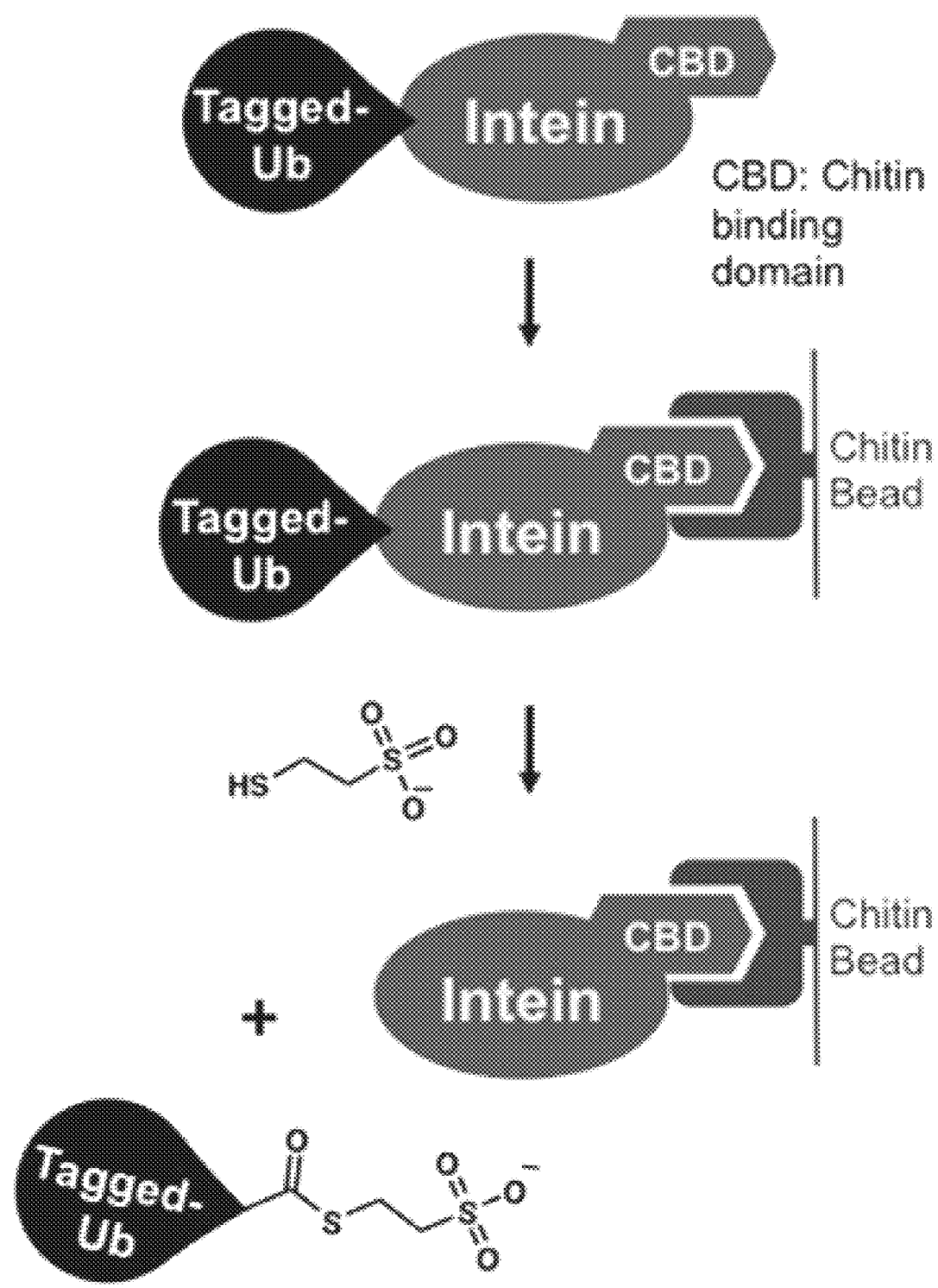
FIG. 12A-12E shows preparation of the 3× FLAG-6× His-ubiquitin$_{1-76}$-mercaptoethansulfonate (Tagged-Ub-MES).
Figure 12B:
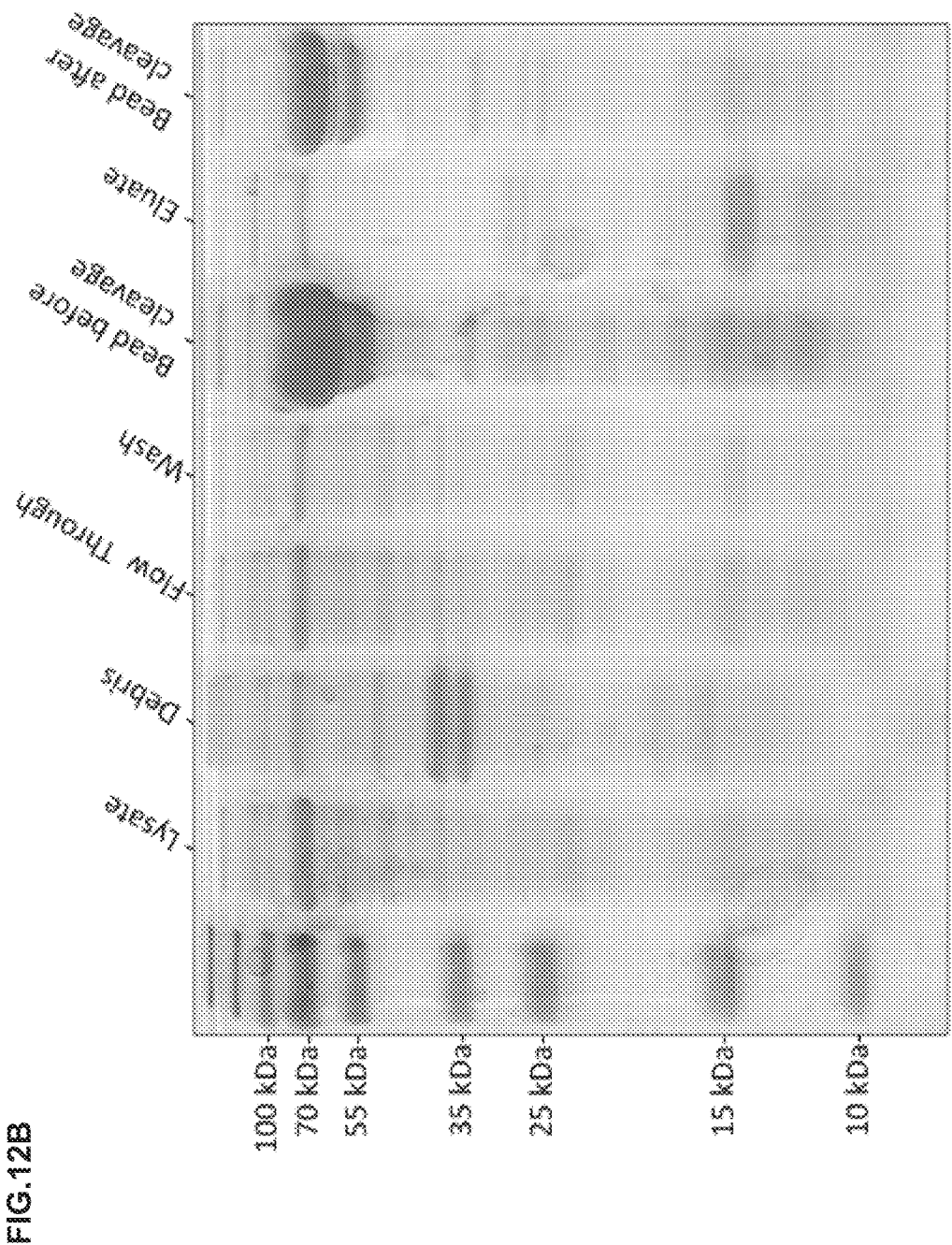
Figure 12C:
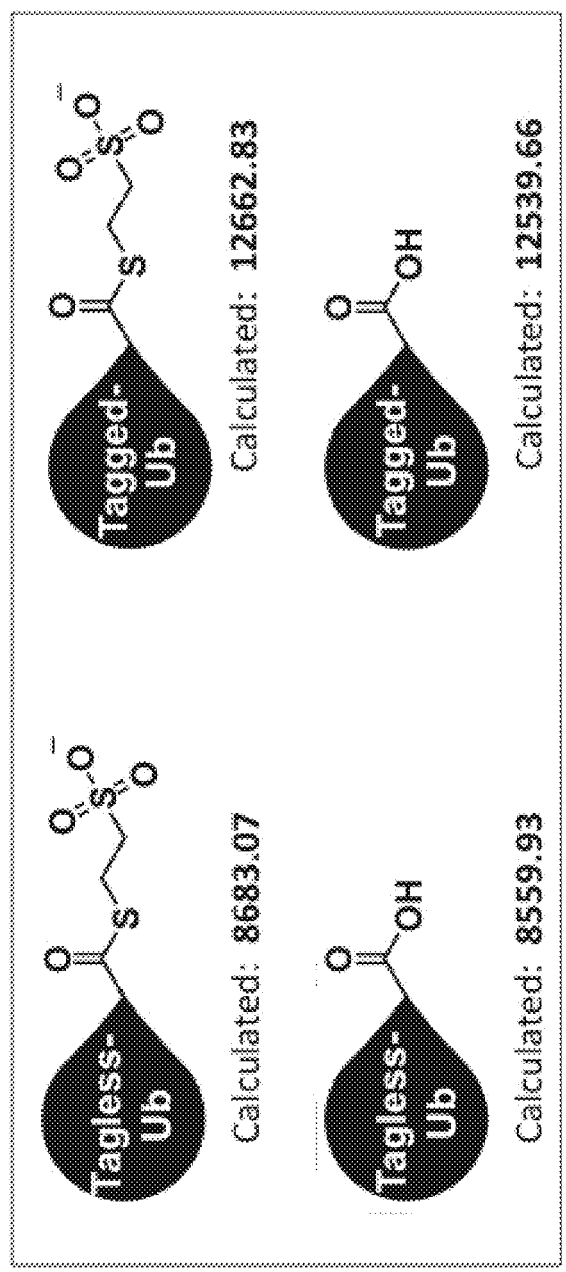
Figure 12D:
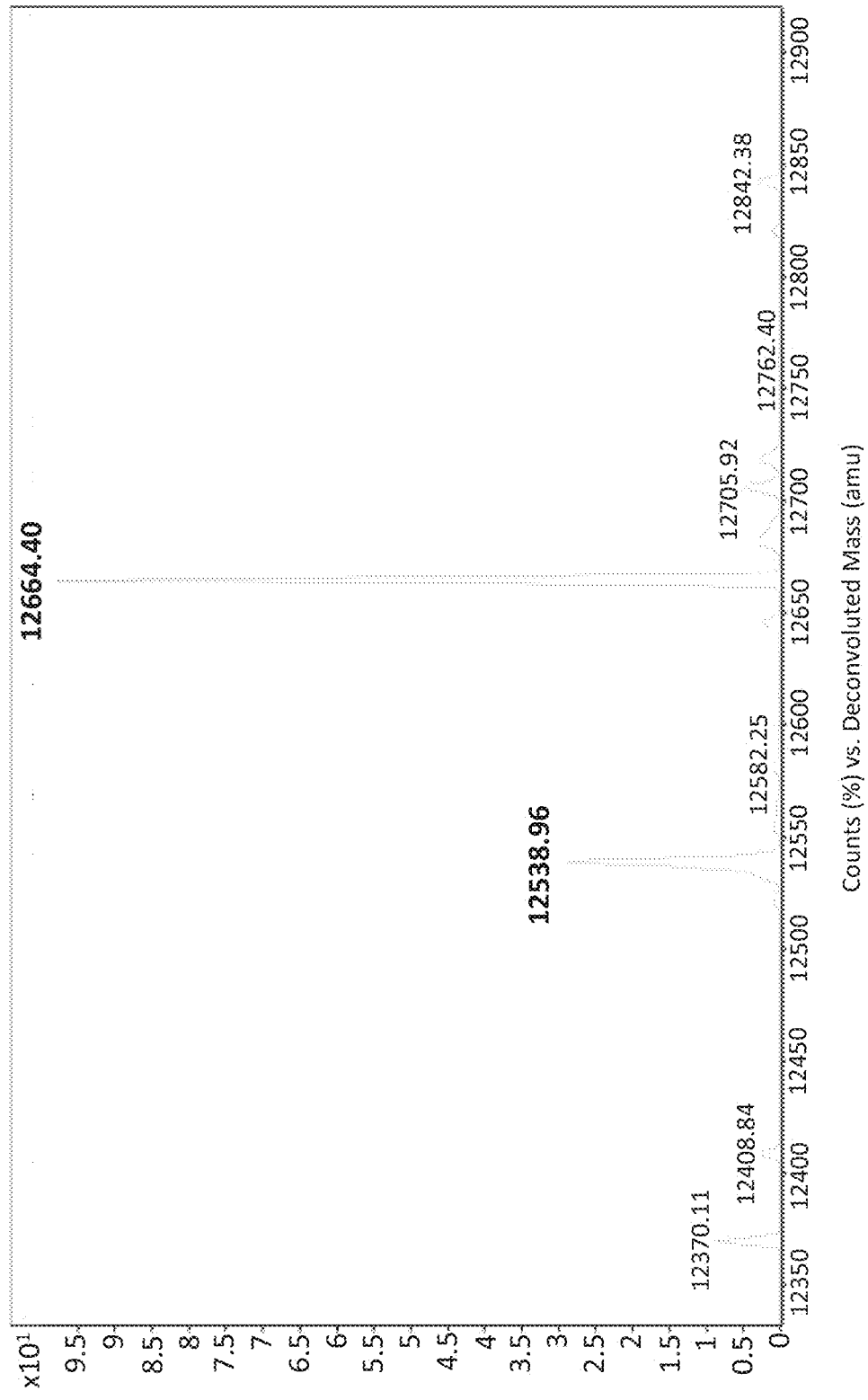
Figure 12E:
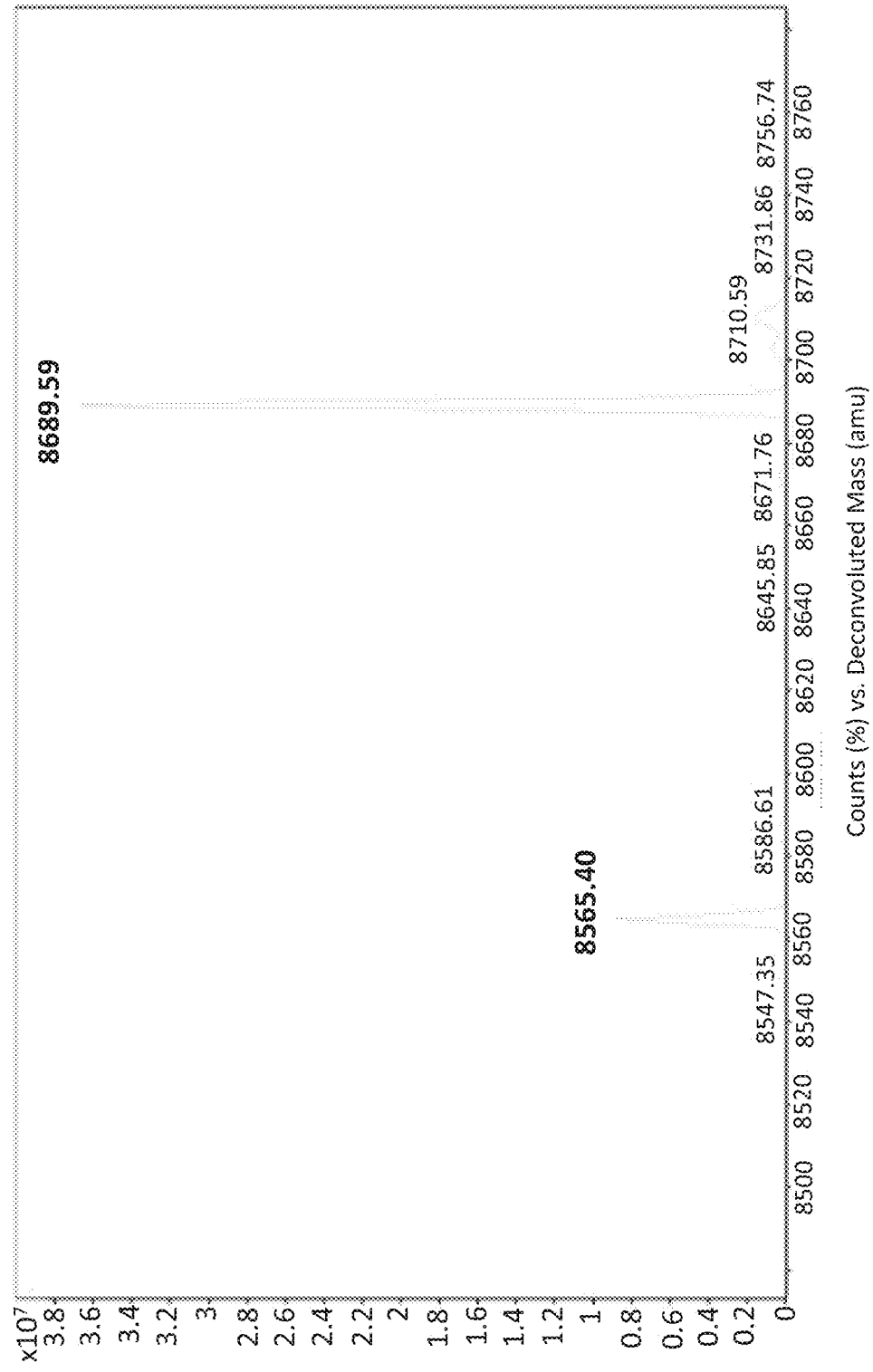

In some embodiments, UbiFlu was synthesized. An exemplary synthesis is shown in FIG. 10A. Ub-MES was prepared as previously described, e.g., using intein technology. Fluorescent thiol SFlu was prepared using standard synthetic chemistry methods (FIG. 10A). Transthiolation reaction was conducted using 1 mM Ub-MES and 10 mM SFlu in HEPES buffer, and the resulting UbiFlu was purified using desalting columns that eliminate excess small molecules. UbiFLu can be further purified using HPLC methods.

Subsequently, UbiFlu activity was tested using Rsp5 as a model HECT E3 ligase. Data collected indicated that upon incubation of Rsp5ΔWW with UbiFlu, the amount of fluorescent UbiFlu decreased and the amount of lower molecular weight fluorescein increased. At the same time, efficient autoubiqutination of Rsp5 was observed. Loss of UbiFlu fluorescence indicated that Rsp5ΔWW undergoes transthiolation reaction with UbiFlu, while autoubiqutinated bands of Rsp5 indicate enzymatic turnover. Further investigations showed that the decrease in the fluorescence of UbiFlu is time dependent, and can be quantified either by densitometry methods or by fluorescence polarization (FIG. 11).

The developed UbiFlu probes find use to screen for molecular entities that modulate (e.g., inhibit or activate) HECT E3, RBR E3, or NEL E3 ligases. Mutation of these ligases is known to cause many human diseases such as hypertensive disorders (Liddle's syndrome), neurological and/or neurodegenerative diseases (Angelman Syndrome, Parkinson's disease), cancers (e.g., MDM2, E6-AP), autoimmune, and development disorders (HECT E3 ITCH), and viral/bacterial infections. Accordingly, developing small molecule tools to study the function of these enzymes is of critical importance for both basic science and drug discovery purposes. To this end, UbiFlu probes provide a unique opportunity to study the effect of chemical entities (e.g., small molecules, peptides, peptidomimetics, antibodies, or other proteins) on the catalytic activity of HECT E3 or HECT E3~Ub thioesters. Activators of HECT E3s or HECT E3~Ub thioesters will increase the rate of UbiFlu consuption, while inhibitors of HECT E3s or HECT E3 thioesters will inhibit the consumption rate of UbiFlu. Changes in the rate of UbiFlu consumption can be detected using the fluorescence detection methods described herein. Thus, the developed assay can be used to discover initial drug leads to treat cancers, neurodegenerative disorders, viral and bacterial infections, hypertensive disorders, and autoimmune disorders.

Many different fluorophores besides fluorescein can be attached to the Ubiqutin-C-terminal thioester, which includes commonly used fluorophores in the field: rhodamines, coumarines, fluorescein, NBD fluororphore, etc.

Example 11

Fluorescence Polarization of 6 µM Ub-Flu with 1 µM Rsp5

During the development of embodiments of the technology provided herein, experiments were conducted to assess the used of the UbiFlu probe with Rsp5. In particular, Ub-Flu (6.0 µM) was mixed with ΔWW Rsp5 (1.0 µM) in 20 mM HEPES 7.5, 50 mM NaCl and then immediately added to a 384 well plate in triplicate (3×70 µL). Fluorescence polarization was observed with the Synergy 4 plate reader every 90 seconds. Polarization units were converted to pmol Ub-Flu. An aliquot of the same reaction mixture was quenched every 15 min for Coomassie and fluorescence gels.

Figure 34A:
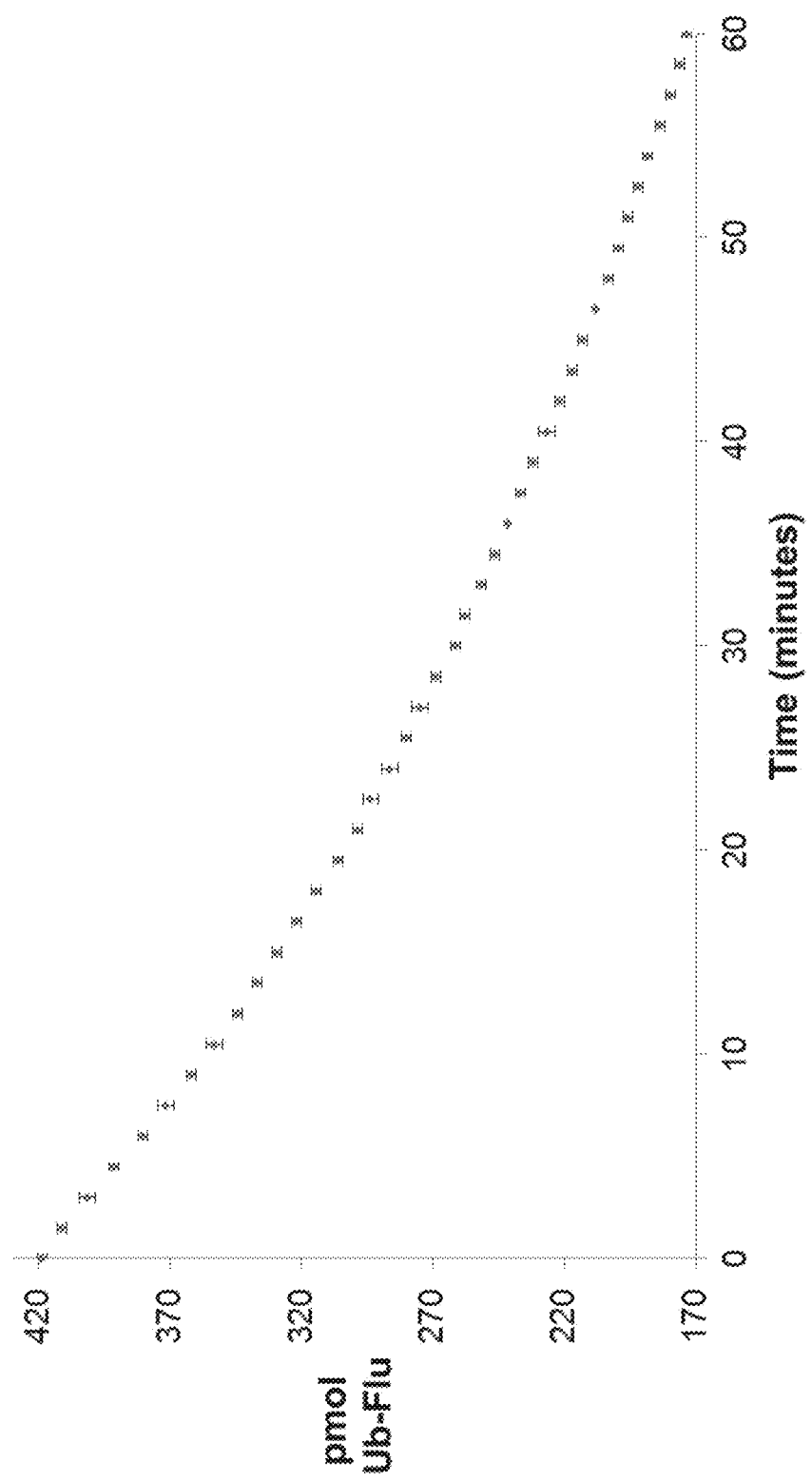
FIG. 34A-34C shows fluorescence polarization of 6 µM Ub-Flu with 1 µM Rsp5.
Figure 34B:
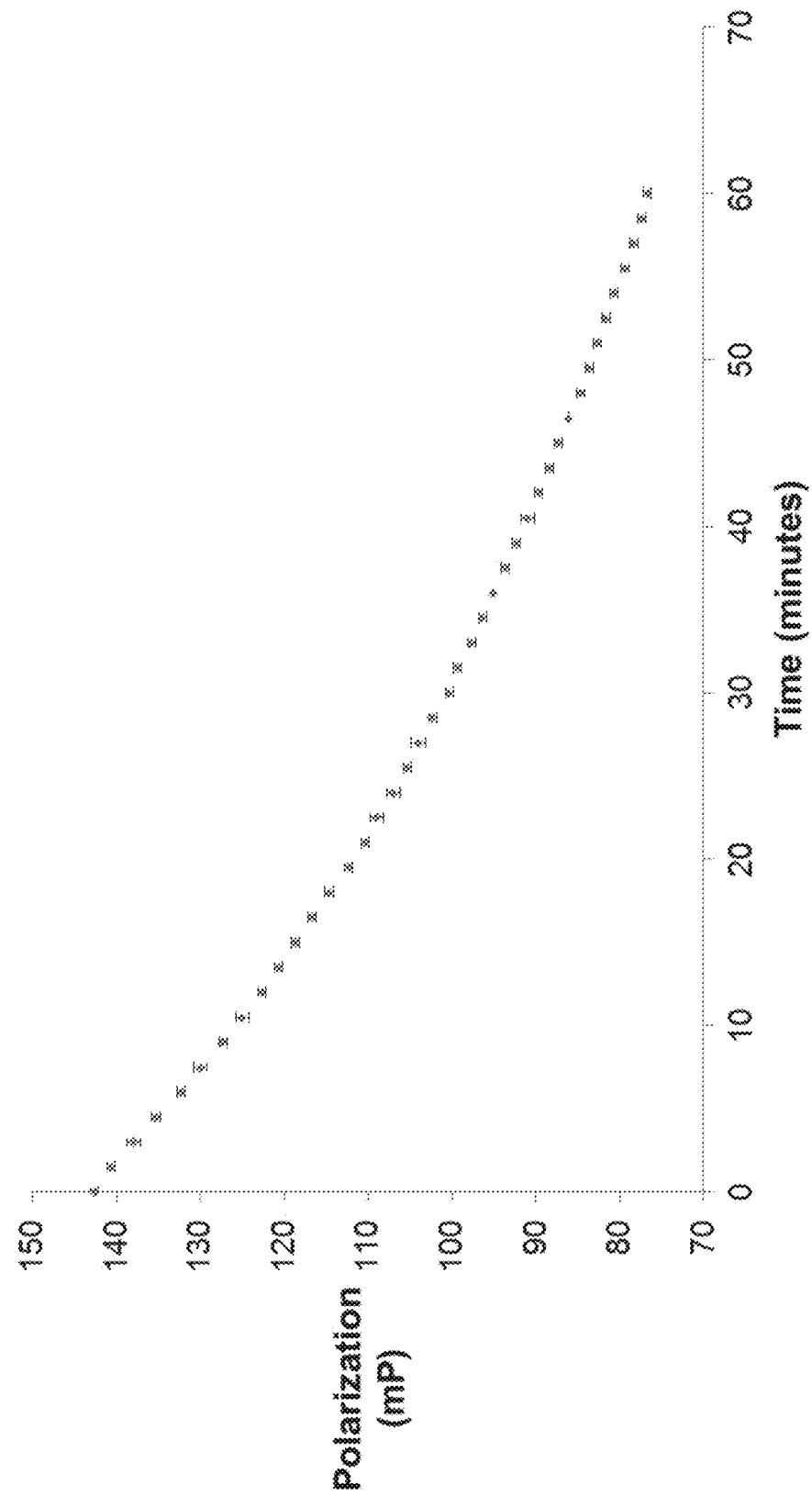
Figure 34C:
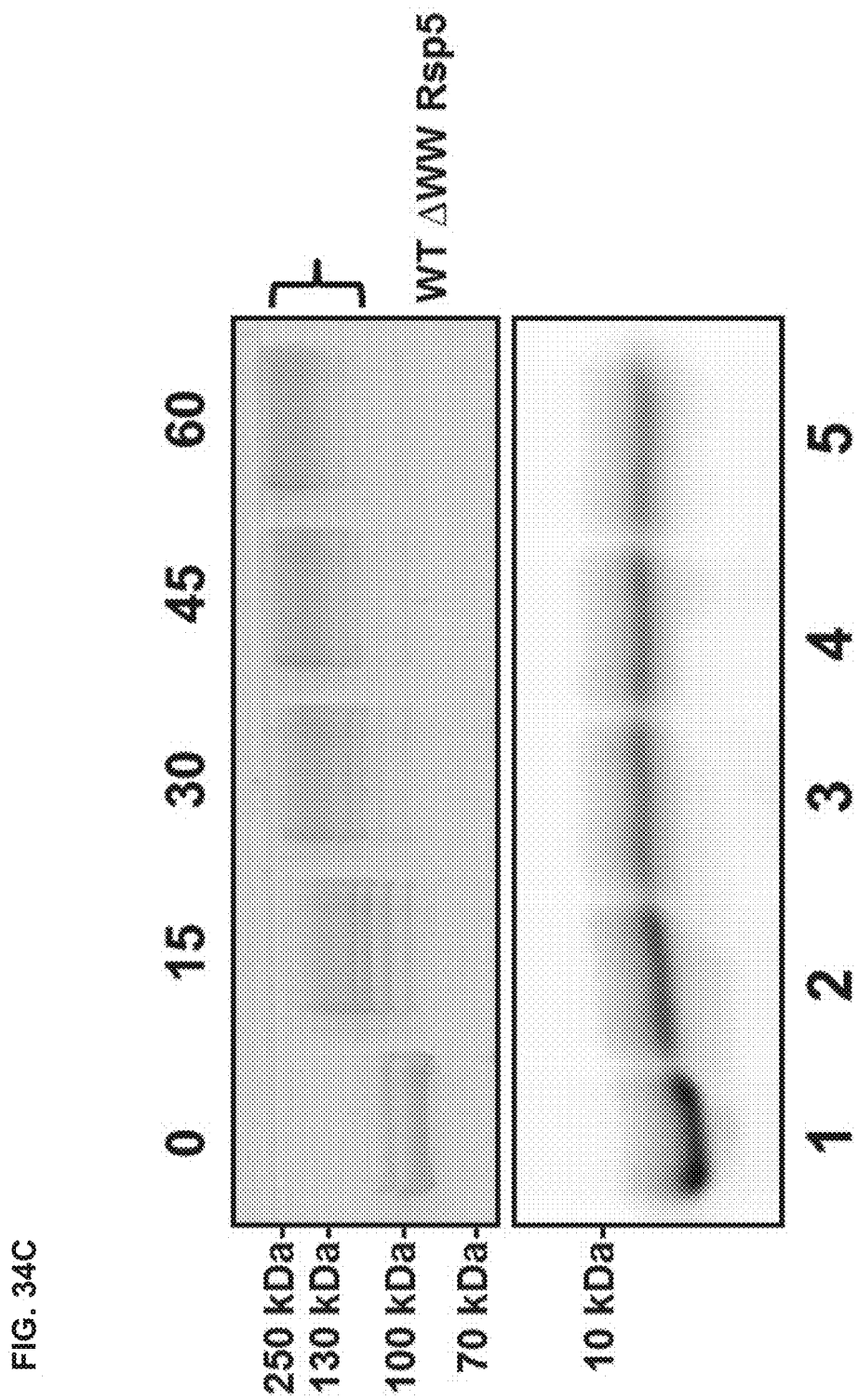

The data collected showed a decrease in fluorescence polarization over the course of approximately 60 minutes, indicating a decrease in the amount of Ub-Flu in the reaction (FIGS. 34A and 34B). Ubiquitination of the ΔWW Rsp5 substrate was monitored by gel electrophoresis (FIG. 34C).

Example 12

UbiFlu is a Mechanism Based Probe for HECT E3 Ligases

E3 ubiquitin ligases (e.g., HECT E3 ubiquitin ligases) are genetically implicated in many human diseases, e.g., in cancer and in neurological, hypertensive, and autoimmune disorders. As described herein, the ubiquitination reaction is complex and requires ATP, Ub, E1, E2, and E3 enzymes, which makes it difficult to study the biochemistry of E3 enzymes (e.g., HECT E3 enzymes) and to identify chemical probes of HECT E3s. Accordingly, during the development of embodiments of the technology provided herein, embodiments of the UbiFlu thioester (e.g., a conjugate of the C-terminus of ubiquitin (Ub) to a fluorescein-thiol) were designed and tested. Data collected during the experiments showed that UbiFlu is a mechanism-based probe that reacts with the catalytic cysteine of the HECT domain is a direct transthiolation reaction to produce a catalytically active HECT E3~Ub thioester and releasing a fluorescent thiol.

Materials and Methods

Buffers. Storage Buffer A: 25 mM NaCl, 12.5 mM HEPES pH 6.7; Storage Buffer B: 250 mM NaCl, 12.5 mM HEPES pH 6.0.

Fluorescence polarization. All fluorescence polarization experiments were conducted with the Synergy4 (BioTek) on Gen5 software (BioTek). The readings were taken under a kinetic protocol with time intervals set as indicated in a given experiment. Reactions (25 µL total volume unless otherwise indicated) were initiated by centrifuging enzyme from the side of a 1.5 mL microfuge tube into solution at the bottom of the tube. The solution was then mixed by gently pipetting and then added (20 µL) to a 384-well plate. The plate was centrifuged for 8 seconds, and then placed inside the Synergy4.

Single turnover assay. Four reactions are run with Rsp5 HECT (5 µM) and UbiFluor (0.25, 0.50, 0.75, or 1.0 µM) in 150 mM NaCl, 6 µM Tween-20, 0.5 mM TCEP, 50 mM HEPES pH 7.5. Each reaction is prepared with 25 µL total volume. The solutions are then mixed by gently pipetting and then added (20 µL) to a 384-well plate. The plate was centrifuged for 8 seconds, and then placed inside the Synergy4.

Multiturnover assay. Four reactions are run with Rsp5 HECT (1 µM) and UbiFluor (10, 12.5, 15, or 20 µM) in 150 mM NaCl. 6 µM Tween-20, 0.5 mM TCEP, 50 mM HEPES pH 7.5. Each reaction is prepared with 25 µL total volume. The solutions are then mixed by gently pipetting and then added (20 µL) to a 384-well plate. The plate was centrifuged for 8 seconds, and then placed inside the Synergy4.

Probe synthesis. Probes were synthesized according the scheme of FIG. 41.

Synthesis of trityl-protected cysteamine. To a mixture of cysteamine hydrochloride (1 g, 8.8 mmol) and trifluoroacetic acid (1.3 mL, 17.6 mmol) in $CH_2Cl_2$ (30 mL) was added tritylchloride (2.4 g, 8.8 mmol). The reaction mixture was stirred for 16 hours at room temperature. The reaction was quenched by adding 1 M NaOH solution (20 mL) and the organic phase was diluted with $CH_2Cl_2$ (50 mL), washed with brine (20 mL), and dried over magnesium sulfate. The white crystalline was obtained from ether/n-pentane precipitation (455 mg, 1.42 mmol, 16% yield). $^1$H NMR (400 MHz, $CDCl_3$); δ 7.43-7.42 (d, 6H), 7.29-7.26 (t, 3H), 7.21-7.19 (t, 3H), 7.16-7.11 (m, 3H), 2.62 (t, 2H), 2.23 (t, 2H). $^{13}$C NMR (400 MHz, $CDCl_3$); δ 144.4, 129.8, 128,6, 127.4, 67.7, 36.9, 29.4.

Synthesis of trityl-protected SFluor. To a mixture of trityl-protected cysteamine (330 mg, 1.0 mmol) and N,N-diisopropylethylamine (345.7 µl, 2.0 mmol) in DMF (5 mL), was added FITC (100 mg, 1.0 mmol). The reaction mixture was stirred at room temperature for 16 hours. The reaction was stirred under an $N_2$(g) stream to reduce the total volume to 1~2 mL. This solution was poured into 48 mL water (50 mM HEPES, pH 6.5) in a 50 mL Falcon tube. The precipitated product was centrifuged at 4000 rpm for 10 min. The precipitate was dissolved in 2~3 mL of MeOH and passed through a silica plug with 50~60 mL EA above the column bed. It is further washed with EA (8% MeOH) until all fluorescent material had eluted. The eluted material was concentrated under reduced pressure to give an orange powder (650 mg, 90% yield).

Synthesis of SFluor. To trityl-protected SFluor (100 mg, 0.141 mmol) in a 20 mL glass scintillation vial was added 1 mL of TFA solution (2.5% triethylsilane and 2.5% water). The mixture was lightly vortexed for two hours at room temperature and poured into diethyl ether (50 mL in a Falcon tube). The precipitated product was centrifuged (4,000 g, 10 min) to obtain an orange pellet (16.3 mg, 0.035 mmol, 83% yield). To purify this product by HPLC, the pellet was dissolved in acetonitrile/water (3:7) with 0.1% TFA (2 mL). A few drops of triethylamine were added to fully dissolve the solid. It was then purified with a gradient HPLC method (ramp from 30%-95% acetonitrile, column: Restek Pinnacle DB C18). The collected major peak was then lyophilized overnight to obtain an orange/red powder (20 mg, 31% yield).

UbMES Synthesis (E1 Enzyme Mediated Synthesis)

In a 50 mL conical vial, the following components were combined according to the given order of addition:

| | |
|---|---|
| 500 mM $NaPO_4$ pH 8.0 (10x buffer) | 2.336 mL (50 mM final concentration) |
| E1 enzyme UBE1 | final concentration 0.25 µM |
| ATP | 129 mg ATP disodium salt (final conc. 10 mM) |
| MESNa | 384 mg (final concentration 100 mM) |

| | |
|---|---|
| MgCl$_2$ | 234 µL 1M solution (final concentration 10 mM) |
| Ubiquitin | (20 mg (Sigma Aldrich), 100 µM final conc) |

Double distilled water was added to bring the final volume to 23.4 mL. The 50 mL conical tube was capped and then gently inverted a few times to mix the contents. It was then placed at 37° C. for 5 hours without any agitation. The solution was then removed from the incubator and concentrated from 23.4 mL to ~2 mL with an Amicon 3 kDa MWCO spin filter. The product was purified through a HiLoad Superdex 75 FPLC column equilibrated with Storage Buffer A (17 mg product obtained, 85% yield).

Ubiquitin-SFluor conjugation. Lyophilized SFluor was dissolved in a few milliliters of methanol and transferred to a tared 20 mL glass scintillation vial. The majority of methanol was removed with rotovap, and then the resulting solid was further dried under a N$_2$(g) stream for 30 minutes. The net mass of SFluor was then determined. SFluor was then dissolved in DMSO/H$_2$O (1:1) with a minimal amount of saturated aqueous NaHCO$_3$ (~30 µL sat. NaHCO$_3$ to 20 mg SFlu), which provides full solubility and changes the color of the solution from yellow to red. It may also be necessary to briefly sonicate the solution in order to fully dissolve SFluor. After setting up the reaction, the leftover SFluor solution is stored at −20° C.

To each of 4×2 mL microcentrifuge tubes, the following reagents were added according to the listed order of addition (final total volume=1111 µL):

| | |
|---|---|
| 1M HEPES pH 7.5 | 111 µL (100 mM final concentration) |
| 100 mM TCEP | 100 µL (9 mM final concentration) |
| 6M guanidinium chloride | 300 µL (1.62M final concentration) |
| 50 mM S-Flu | 300 µL (13.5 mM final concentration) |
| 700 µM Ub-MESNa | 300 µL (189 µM final concentration) |

After closing all 4 reaction tubes, they were covered in aluminum foil and set to lightly vortex for 120 minutes. At this point, Storage Buffer B (889 µL) was added to each tube to bring the total volume to 2.0 mL. The reaction solutions were added to a Slide-A-Lyzer Dialysis Cassette (3-12 mL size, 3,500 Da MWCO, Life Technologies) pre-hydrated in Storage Buffer B. Dialysis was performed in 2 L Storage Buffer 3×2 hours.

Dialyzed material was further purified through a HiLoad Superdex 75 FPLC column equilibrated with Storage Buffer B. UbiFlu elutes around 120 mL total elution volume, while ubiquitin elutes around 90 mL. The UbiFlu fractions were collected and concentrated with Amicon Ultra-15 Centrifugal Filter Units (to 50-100 µM). UbiFlu was aliquoted, snap frozen in N$_2$(l) and then stored at −80° C. (4.5 mg, 60% yield).

Results

As indicated by the data collected, the UbiFlu probe provides for monitoring the kinetics of the HECT transthiolation reaction. In particular, consumption of UbiFlu provides a signal that is monitored with a real-time fluorescent polarization assay to follow the progress of the transthiolation reaction. This bimolecular reaction is modeled by Michaelis-Menten kinetics and provides a technology to detect defects in the transthiolation and isopeptide bond ligation steps catalysed by HECT E3 enzymes. In some embodiments, UbiFlu finds use in assays for identifying chemical probes of HECT E3 enzymes. Thus, embodiments of UbiFlu and its ubiquitin-like protein analogues find use in quantifying the activity of other E2 and E3 enzymes that have catalytic cysteines for biochemistry or chemical probe discovery purposes.

Typically six components are required for the ubiquitination reaction: ATP, Ub, E1, E2, E3, and a protein substrate. Furthermore, mixtures of E1~Ub, E2~Ub, and E3~Ub thioesters, and various polyubiquitinated products are typically formed, and additional reagents are needed to detect polyubiquitinated reaction products. Assays typically involve used of labor intensive SDS PAGE gels to separate and quantify E1~Ub, E2~Ub, and E3~Ub thioesters, and the poly-ubiquitinated substrates. Accordingly, assays (e.g., drug discovery assays) suffer from false positives due to the off-target inhibition of E1 and E2 enzymes. Thus, there is an urgent need to develop simple and minimalist assays for E3 ligase activity.

Accordingly, experiments were conducted during the development of embodiments of the technology provided herein to test aspects of HECT E3 family ligases using embodiments of UbiFlu as provided herein. In particular, UbiFlu provides an analogue to Ub~MESNa and, as described herein, provides a fluorescence polarization (FP) readout of HECT E3 enzyme activity (e.g., formation of a thioester with Ub to form HECT~Ub before transferring it to the substrate protein). In some embodiments, enzyme activity is monitored in real-time. Data were collected from experiments using an embodiment of the UbiFlu probe comprising a fluorescein thiol (Fluor-SH) conjugated to the C-terminal ubiquitin Gly76 through a thioester prepared via a transthiolation reaction.

Figure 35:
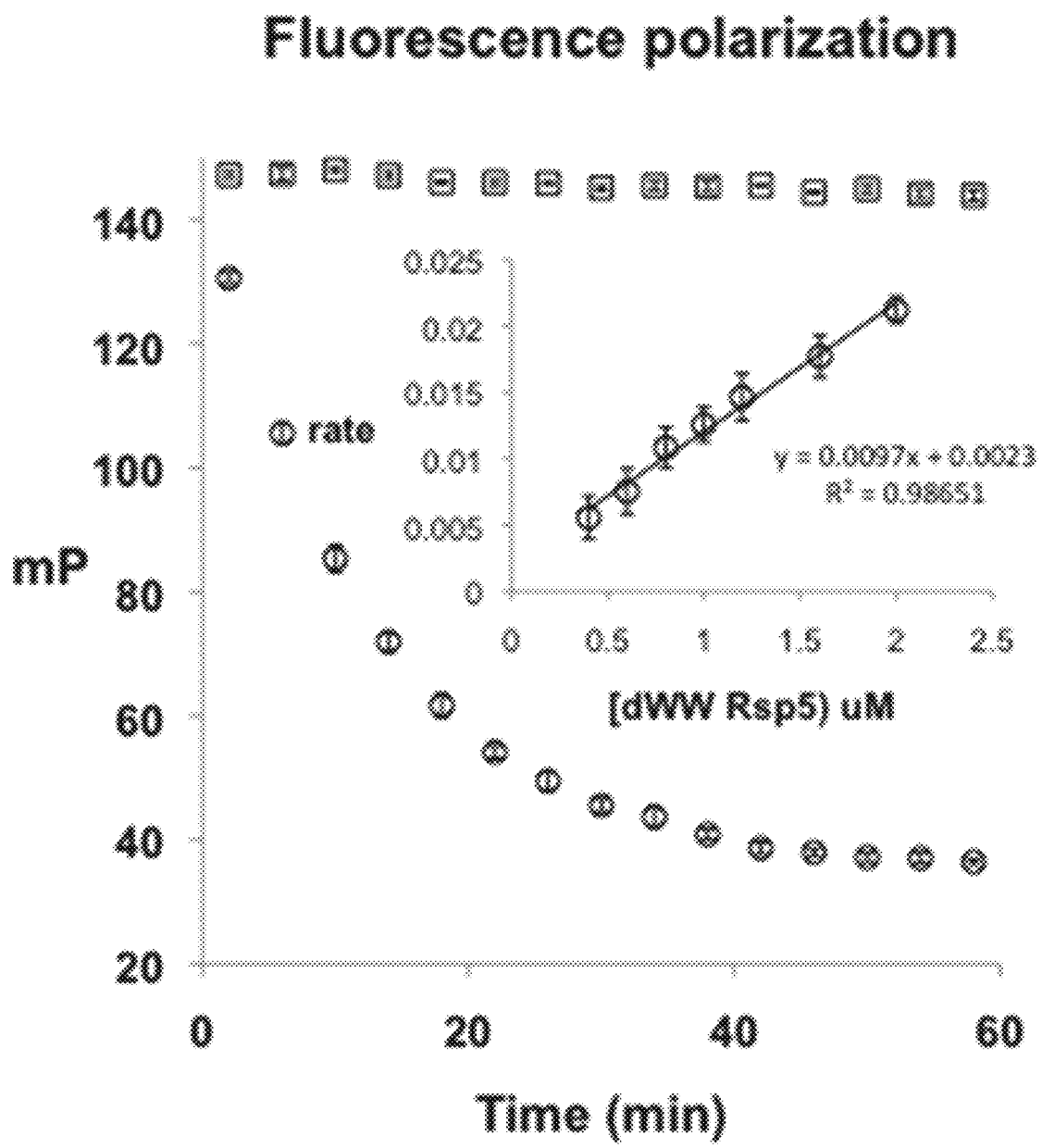
FIG. 35 shows Fluorescence polarization of reactions with UbiFlu (1 µM) and wild type ΔWW Rsp5 (5 µM, circles) or catalytically inactive ΔWW Rsp5 C777A (5 µM, squares) in a 384-well plate. Note: ΔWW Rsp5 is a 70.5 kDa enzyme lacking the WW domains between the C2 and HECT domains.

Data collected during experiments conducted in the development of embodiments of the technology provided herein indicated that, in the presence of UbiFlu, the catalytic cysteine of E3 ligase (e.g., HECT E3 ligase, e.g., Rsp5) undergoes transthiolation with the thioester to liberate Fluor-SH and to generate the catalytically active HECT~Ub thioester. As described herein, the transthiolation of UbiFlu with HECT E3 ligase is monitored in real-time with FP to observe catalysis (e.g., in a multiplex, parallel format, e.g., in a 384-well plate) without adding additional fluorescent reagents (FIG. 35).

The standard deviation for each FP measurement was less than 1% of the dynamic range (~1 mP/~106 mP)—thus, the UbiFlu measurements were remarkably precise and sensitive to changes in the catalytic activity of E3 enzymes.

Moreover, by changing the ratio of HECT E3 to UbiFlu, reactions were performed under single turnover (ST) conditions (e.g., using an excess of HECT E3) to measure transthiolation rates. Alternatively, reactions were performed under multiple turnover (MT) conditions (e.g., using an excess of UbiFlu) to detect defects in isopeptide bond ligation. By analyzing the reaction between UbiFlu and each of 16 Rsp5 alanine point mutants under ST and MT kinetic conditions, the data collected indicated that UbiFlu detects defects in transthiolation and ligation. Thus, it is contemplated that UbiFlu provides a technology for enzymatic studies and HECT E3 drug discovery. In some embodiments, UbiFlu finds use in identifying previously unknown residues important for Rsp5 catalysis and in screens to discover small molecule probes of HECT E3s.

Figure 38A:
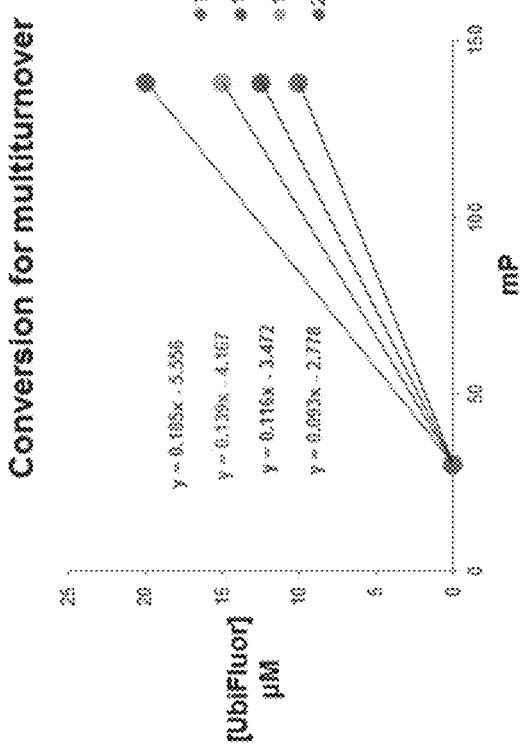
FIG. 38A-38B shows converting polarization to UbiFlu concentration.
Figure 38B:
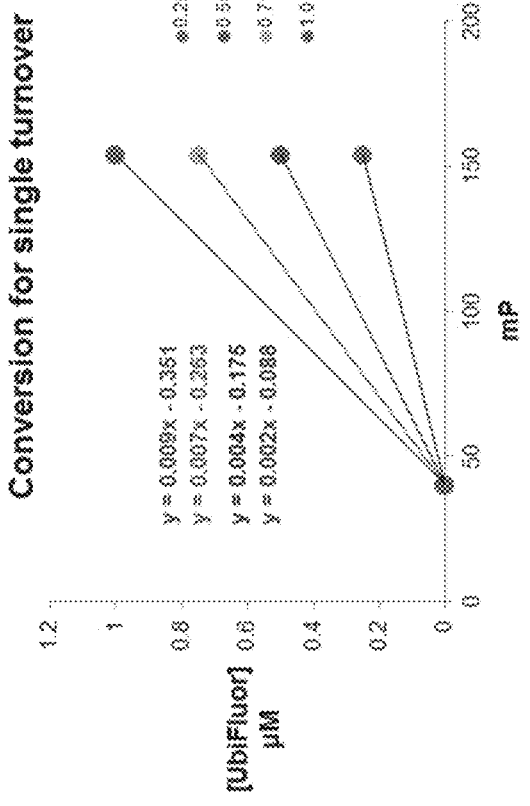

For example, experiments were conducted during the development of embodiments of the technology to collect data characterizing the well-studied *S. cerevisiae* HECT E3 Rsp5, which harbors a C2 domain, followed by three WW domains, and the C-terminal catalytic HECT domain. In some experiments, a ΔWW Rsp5 construct was used that lacks the three WW domains and autoubiquitinates in the presence of the excess of UbiFlu. In these experiments (e.g., using a minimal system that does not comprise substrate), data indicated that auto-ubiquitination occurred with wider multi turnover reaction conditions (FIG. 35). Under single turnover conditions, diminution of UbiFlu accumulation was observed with the simultaneous production of fluorescein and monoubiquitinated ΔWW Rsp5. In some embodiments, single turnover and multiturnover reactions are performed in a parallel format (e.g., 384 well plate) and monitored with kinetic fluorescence polarization (FIG. 35). To convert polarization values (mP) to units of UbiFlu concentration (µM), raw polarization data was converted according to a linear relationship observed between polarization and the ratio of UbiFlu to free SFluor and ubiquitin (FIGS. 36-38). It was observed that the pool of available UbiFlu was consumed more rapidly in the presence of excess enzyme, and initial velocities of consumption were linear with enzyme concentration under both conditions. Also, the overall progress curve for UbiFlu consumption agreed with gel-based measurements of the same reactions.

In some embodiments, the technology finds use in kinetic studies, e.g., using a construct comprising a catalytic HECT domain of Rsp5. The Rsp5 HECT domain undergoes weak auto-ubiquitination (e.g., weak auto-ubiquitination relative to the ΔWW Rsp5 construct) and instead ligates Ub onto the surface lysine of UbiFlu under multiturnover reaction conditions, producing Ubi-UbiFlu. It was contemplated that Ubi-UbiFlu may cause an apparent increase in the fluorescence polarization signal, thus causing an apparent decrease in UbiFlu consuption rates. Accordingly, experiments were conducted to assess if this interference is significant. In particular, experiments were performed using reactions conducted under multi-turnover reaction conditions in the presence of excess L-lysine. L-Lysine accepts Ub from Rsp5, and thus prevents the formation of Ubi-UbiFlu. Data collected indicated minimal differences in $k_{cat}/K_M$ values for Rsp5 between 0-50 mM lysine despite a significant decrease in the amount of Ubi-UbiFlu at 50 mM lysine. Based on these results, additional experiments were conducted using multi-turnover reaction conditions to assess reactions of UbiFlu and HECT domain in the absence of exogenous lysine.

UbiFlu consumption was measured in the presence of 8× SFlu and no inhibition was observed; thus, the liberated SFluor does not influence subsequent catalysis. Further, while fluorescence quenching occurs at UbiFlu concentrations greater than 200 µM, a linear correlation between polarization and the ratio of UbiFlu to free fluorophore and ubiquitin was observed, which allowed measurements to be obtained at those concentrations (FIG. 38).

Further, during the development of embodiments of the technology provided herein, experiments were conducted to characterize the enzymatic relationship between UbiFlu and HECT ligase, e.g., by collecting data to calculate kinetic (e.g., Michaelis-Menten) parameters. Since it has been shown that the C-lobe of HECT E3 engages in non-covalent interactions with the ubiquitin in both the HECT E3:E2~Ub complex and in the HECT E3~Ub thioester, it is contemplated that UbiFlu engages the HECT domain through non-covalent associations with the C-lobe using the same surface areas as in the native cascade.

According to the contemplated model, this association is governed by $k_{on}$ and $k_{off}$ rates, the rate of subsequent transthiolation is given by $k_1$, and the rate of the subsequent isopeptide ligation step by $k_2$. To analyze the reaction with Michaelis-Menten kinetics, initial reaction velocities at a given concentration of UbiFlu were measured for the first 15 minutes under conditions where linearity is indicated by an of $R^2>0.98$ and less than 10% UbiFlu has been consumed.

Thus, by treating the Rsp5 HECT domain with an excess of UbiFlu, data were collected and kinetic calculations produced a $k_{cat}$ of 0.091±0.010 s$^{-1}$ and a $K_M$ of 791.9±121 M$^{-1}$s$^{-1}$ (FIG. 36B). In some embodiments, kinetic parameters are evaluated under pseudo first-order conditions where the pseudo first-order rate constant is $k_{cat}$[HECT]$_0$/$K_M$. When the UbiFlu concentration is far below $K_M$, this constant can also be calculated under single turnover conditions, where HECT ligase is in excess. The $k_{cat}/K_M$ calculated for wild type Rsp5 HECT from multi-turnover pseudo first-order conditions was 93.8±13.4 M$^{-1}$s$^{-1}$, which agrees reasonably well with the same constant calculated from the Michaelis-Menten experiment (119±22 M$^{-1}$s$^{-1}$). This agreement with the Michaelis-Menten experiment indicates that, the pseudo first-order conditions are appropriate.

These data indicate that UbiFlu provides a technology to assess (e.g., quantitatively) residue-specific contributions to HECT E3 ligase catalysis.

During the development of embodiments of the technology, experiments were conducted under both single and multiturnover reaction conditions, since one condition measures the transthiolation rate ($k_1$) and the other detects changes in isopeptide ligation step ($k_2$). With excess ligase, the experimental assays are conducted under conditions where each ligase molecule reacts with at most one UbiFlu molecule. Therefore, rates observed under the single turnover condition directly assess the transthiolation of UbiFlu by the HECT catalytic cysteine. Since SFluor is liberated upon transthiolation, the fate of the resulting HECT~Ub (hydrolysis or ligation) does not affect the UbiFlu consumption rate under ST; an excess of ligase ensures that any ligation defect that could prevent the dissipation of HECT~Ub will not limit the consumption of UbiFlu. However, with excess UbiFlu under MT, the experimental assays are conducted under conditions where each ligase molecule has the opportunity to process more than one UbiFlu molecule. Any defect that prevents the discharge of the ubiquitin from the HECT E3~Ub thioester limits UbiFlu consumption because the HECT~Ub conjugate is unable to react with UbiFlu before discharging the thioester-linked Ub. Thus, the rates observed under a multiturnover condition are a composite of both transthiolation ($k_1$) and subsequent steps including isopeptide ligation step ($k_2$).

Further experiments were conducted to observe rates of UbiFlu consumption for specific point mutants under single or multiturnover reaction conditions. Data collected were used to identify residues that (1) affect transthiolation and that (2) only impact the mechanisms following transthiolation (e.g., ligation). Furthermore, while the rate of UbiFlu consumption varies with increasing concentrations of free lysine under MT conditions, the rate does not change under ST conditions. Thus, rates from ST conditions describe the transthiolation step while MT conditions describe steps following transthiolation, which include ligation to lysine.

And, further experiments were conducted during the development of embodiments of the technology to characterize the mechanism of UbiFlu reaction with HECT E3s. In particular, data were collected from monitoring reactions of UbiFlu with mutants of the catalytic Rsp5 HECT domain, e.g., experiments were conducted using UbiFlu to quantify defects in the enzyme activity of alanine scanning mutants around the Rsp5 HECT domain and, consequently, confirm that UbiFlu provides a technology to study HECT E3s.

It was contemplated that Rsp5 mutants defective in transthiolation with E2~Ub thioesters are less efficient in reacting with UbiFlu under single and multiple turnover conditions. In particular, it was contemplated that Rsp5 mutants defective in isopeptide ligation, but not in transthiolation with E2~Ub, are efficient and comparable with the wild type in reacting with UbiFlu under single turnover reaction conditions, but are less efficient at processing UbiFlu under multiple turnover reaction conditions. This lack of efficacy would be due to the accumulation of inactive HECT E3~Ub thioester, defective at discharging the Ub.

Previous structural studies have revealed how HECT domains (1) receive ubiquitin onto their catalytic cysteine from an upstream E2~Ub thioester; and (2) how the subsequent HECT~Ub thioester transfers Ub to the acceptor lysine of substrate. A HECT domain features an N-terminal lobe (N-lobe, ~250 residues) tethered to a C-terminal lobe (C-lobe, ~110 residues) that bears the catalytic cysteine and rotates to accomplish steps (1) and (2). During transthiolation (1), the C-lobe rotates to bring the HECT catalytic cysteine, proximal to the E2~Ub thioester bond to accomplish transthiolation. In this ternary complex, E2 binds a V-shaped hydrophobic groove on the N-lobe of the catalytic HECT domain and ubiquitin in E2~Ub thioester makes precise contacts with the Leu771 patch of the HECT C-lobe. The L771A mutation on Rsp5 disrupts the interaction of ubiquitin with the C-lobe of the HECT domain in the ternary E2~Ub/Rsp5 complex and inhibits the transthiolation reaction of the E2~Ub thioester with the catalytic cysteine of Rsp5.

Next, the C-lobe of HECT~Ub thioester rotates into a distinct conformation where the surfaces of ubiquitin are sandwiched between the N- and C-lobes to form an active site that catalyzes the transfer of Ub from HECT~Ub thioester onto an acceptor lysine. Within this "sandwich conformation", the initial contacts between the Ub and the C-lobe are maintained throughout the catalysis, starting from receiving the ubiquitin from E2~Ub and concluding with the release of the ubiquitin onto the lysine of the substrate. Moreover, specific interactions between the N and C-lobes of HECT in the isopeptide ligation conformation are critical for the ligation of Ub onto acceptor lysine. Another feature of HECT catalysis is the processivity site, which involves a second non-covalent ubiquitin binding site on the N-lobe of HECT. Mutation of residues critical to conformations of either (1) or (2) stalls the passage of Ub to either the catalytic cysteine of HECT or to the lysine of the substrate. Disruption of the ubiquitin binding to the processivity site, on the other hand, inhibits the kinetics of poly ubiquitin chain synthesis.

Accordingly, experiments were conducted during the development of embodiments of the technology to collect, data relating to transthiolation and ligation kinetics using UbiFlu. First 16 alanine mutants of the Rsp5 HECT domain were produced for use in these experiments. These Rsp5 HECT domain mutants are defective in transthiolation of E2~Ub or in isopeptide ligation, e.g., Rsp5 mutants that are transthiolation deficient demonstrate a transthiolation defect in a single turnover reaction with UbFluor and Rsp5 mutants that are defective in ligation are less efficient at processing UbiFlu under multiturnover reaction conditions.

Figure 39C:
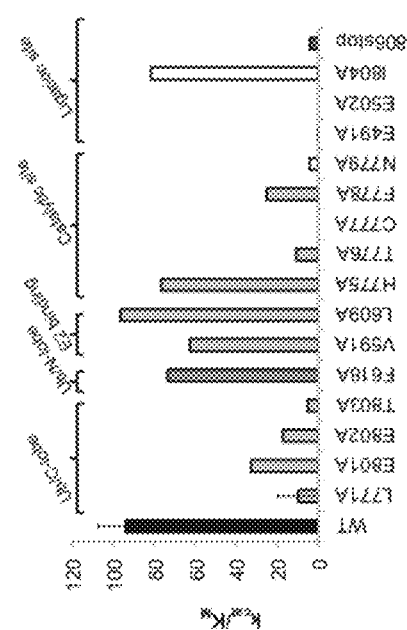
FIG. 39A-39C shows that UbiFlu detects biochemical defects in HECT E3 ligases.
Figure 39B:
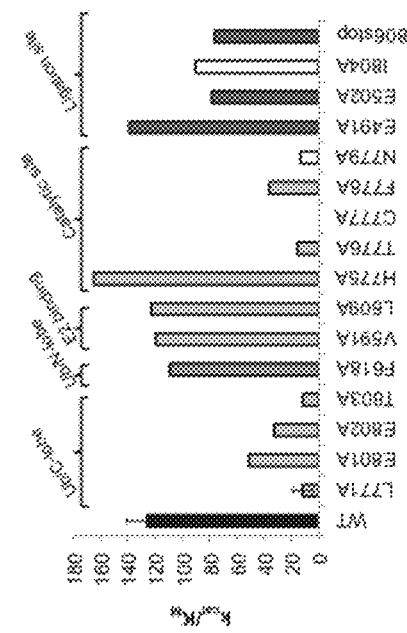
Figure 39A:
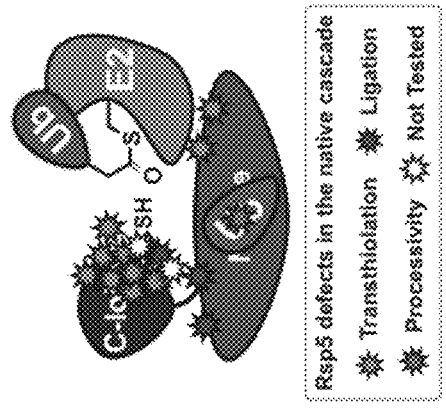

Data were collected from testing all 16 Rsp5 HECT mutants with UbiFlu under single and multiple turnover conditions to observe defects in transthiolation or ligation (FIG. 39). Further, experiments were conducted to test mutations at known Ub:HECT interfaces (e.g., based on the known crystal structures of HECT E3~Ub, HECT E3:E2~Ub, and HECT E3:Ub). Data collected indicated that mutations at the Ub:C-lobe interface severely attenuated single and multiturnover rates. Rsp5 residues L771, E801, E802, and T803 form critical interactions with ubiquitin during its residence on the HECT domain from transthiolation to ligation in the native ubiquitination reaction. Accordingly, severe attenuation of single and multiturnover UbiFlu reactions was observed with each of the related point mutants (FIG. 39B-C). In contrast, ubiquitin encounters its HECT N-lobe binding site during the extension of poly ubiquitin chains after it has passed through transthiolation. Accordingly, a E618A mutation at the N-lobe of Rsp5, which is known to disrupt non-covalent ubiquitin binding to the N-lobe and inhibit processivity (formation of >4 Ub in a chain), did not inhibit UbiFlu processing under single or multiturnover conditions. The observed low (e.g., insignificant) inhibition of UbiFlu processing under multiturnover conditions was consistent with the reaction conditions, <10% of UbiFlu is consumed, only ubiquitinated UbiFlu is formed, and Ub chains greater than 4 Ub were not observed.

Thus, data collected during the experiments indicated that the ubiquitin of UbiFlu encounters the HECT domain C-lobe for transthiolation between and HECT E3, similar to the ubiquitin of the Ub~E2 thioester in the native cascade, e.g., as contemplated by the model described herein. Furthermore, the V591A and L609A mutations in Rsp5 that disrupt E2~Ub binding to Rsp5 and inhibit transthiolation step did not cause observable transthiolation or ligation defects since the UbiFlu experimental system observed in the experiments lacks the E2 enzyme.

Transthiolation of E2~Ub to form HECT~Ub is also attenuated by mutating the HECT catalytic cysteine C777 or the residues surrounding it, such as T776 and F778, which are conserved across HECT ligases. With UbiFlu, the same Rsp5 mutants (T776A, F778A) register low $k_{cat}/K_M$ values under single and multiturnover reactions compared to the wild type. Given these defects, it was thus surprising that Rsp5 H775A, which was also reported to be defective in the native transthiolation cascade, demonstrated robust $k_{cat}/K_M$ under single and multiturnover conditions. The co-crystal structure of an E2~Ub-HECT transfer complex shows the corresponding histidine of the Rsp5 human homologue Nedd4L forming interactions with Ub G76 and L119 of the UbcH5c. This structure indicates that this histidine residue is important for anchoring E2~Ub thioester to HECT E3 for subsequent transthiolation step. Since H775A Rsp5 mutant was similarly efficient in reacting with UbiFlu that lacks E2 enzyme, under single and multiturnover reaction conditions, it is contemplated that the role of H775 in Rsp5 is to anchor the E2 enzyme of the E2~Ub thioester to the C-lobe of Rsp5 for the subsequent transthiolation reaction.

Experiments were conducted using UbiFlu to identify residues of HECT E3 important for the isopeptide ligation step. It is contemplated that, to transfer Ub to a substrate, HECT domain must adopt the "sandwich conformation" where the surfaces of Ub, N-, and C-lobes congregate to form a composite active site that catalyzes transfer of the ubiquitin onto the lysine of the protein substrate. Thus, when residues that form and stabilize this proposed site (E491, E502, and F806) are mutated to alanines, HECT~Ub is unable to transfer Ub in the native ubiquitination cascade. In accordance with this contemplation, it was observed that the same mutants were virtually unreactive under multiturnover conditions with UbiFlu but processed UbiFlu under the single turnover reaction conditions, indicating that transthiolation rates are not affected (e.g., properties which are similar to the native ubiquitination cascade). During these studies it was also discovered that N779 residue of Rsp5, which is conserved in Nedd4 family of HECT E3s and majority of other HECT E3s, also affects transthiolation rates and inhibits UbiFlu processing under the single and multiple turnover reaction conditions, indicating that these residues are important for catalysis. Interestingly, this residue is conserved in HECTs, but its catalytic role was not previously evaluated.

Figure 40:
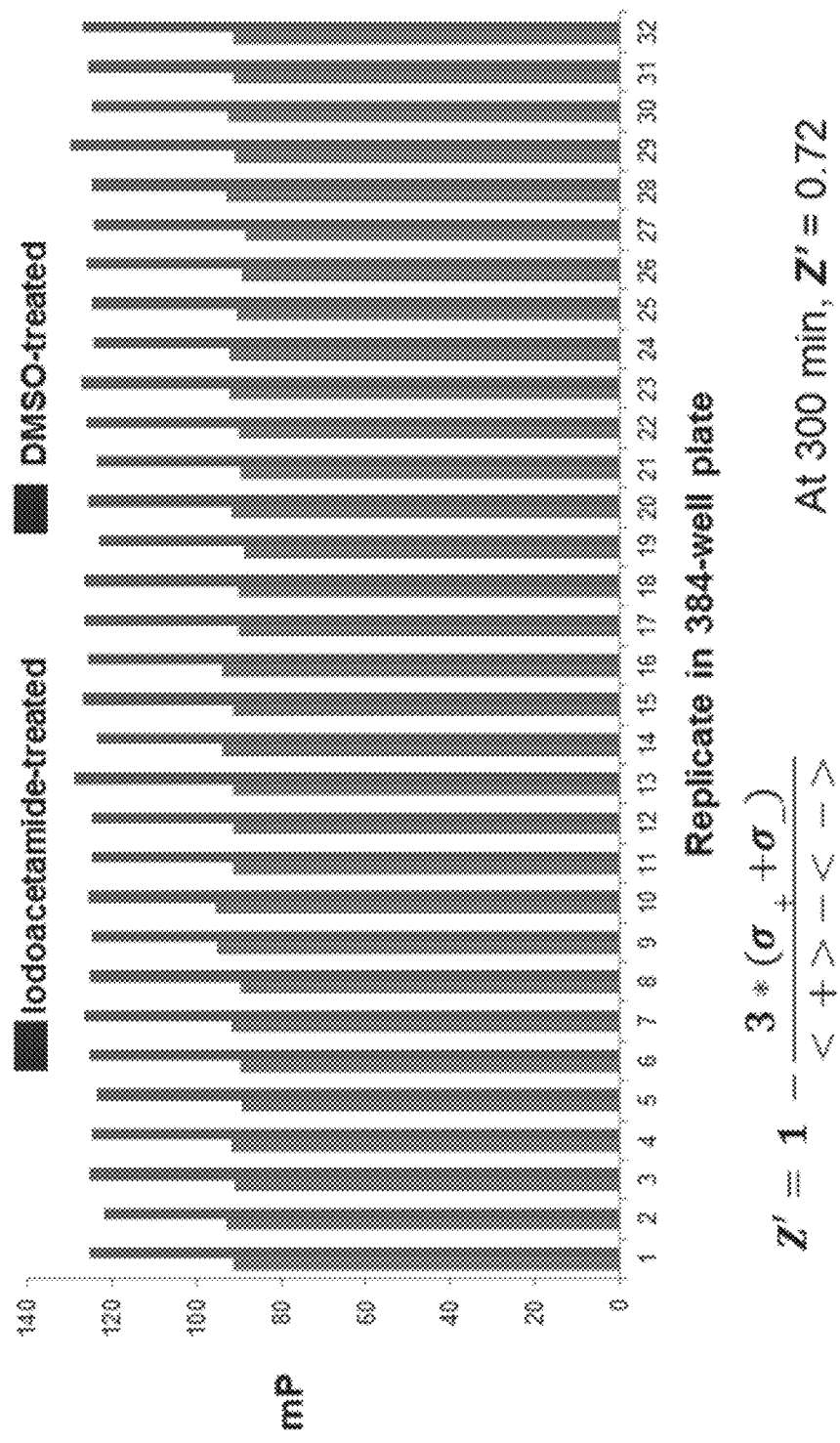
FIG. 40 shows that UbiFlu produces different products under single vs multiturnover conditions. Nedd4-1 HECT (0.5 μM) was incubated in a 384 well plate in 50 mM HEPES pH 7.5, 50 mM NaCl at 25° C. with DMSO (0.2%) or DMSO with iodoacetamide, (1 mM) for 1 hour. UbiFlu (5 μM) was then added and incubated with enzyme for 5 hours before endpoint fluorescence polarization readings were recorded with the Analyst GT.

In summary, the technology provides a class of probes named UbiFlu (or "UbiFluor"), e.g., that find use in some embodiments for studies of ubiquitination, e.g., to study ubiquitin ligases, to study E3 ligases, e.g., HECT E3 ligases. As indicated by experiments conducted during the development of embodiments of the technology provided herein, UbiFlu quantitatively measures the enzymatic activity of HECT E3s and detects defects in trans-thiolation or isopeptide ligation. Data collected during these experiments indicates that UbiFlu recapitulates critical aspects of the native mechanism of protein ubiquitination by HECT ligase including the C-lobe:Ub interaction, involvement of residues flanking the catalytic cysteine, and adoption of a sandwich conformation for ligation. This eliminates and/or minimizes the concern that UbiFlu undergoes "non-specific" transthiolation with the catalytic cysteine of HECT E3s, which would preclude its use as a mechanism-based probe for HECT E3s. It is contemplated that finds use to design assays for HTS screens to discover chemical probes for ubiquitination, e.g., ubiquitin enzymes such as, e.g., E3, e.g., HECT E3s. As a proof of concept, iodoacetamide was used in experiments conducted during the development of embodiments of the technology to show that UbiFlu detects small molecule inhibitors of HECT E3s (FIG. 40).

Example 13

UbiFlu Finds Use in Studying E3 Ligases in General

During the development of embodiments of the technology provided herein, experiments were conducted to test the use of UbiFlu with other E3 ligases, e.g., Nedd4-1, WWp1, and RBR E3 pParkin.

Figure 42A:
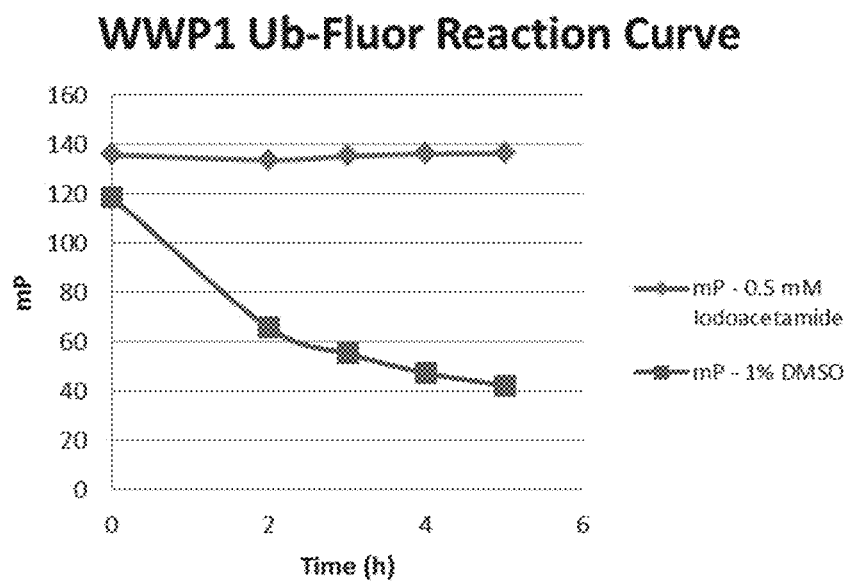
FIG. 42A-42B shows the use of UbiFlu with WWP1 E3 ligase. Data were plotted either mP vs. time (FIG. 42A) or [UbiFlu] remaining vs. time (FIG. 42B).
Figure 42B:
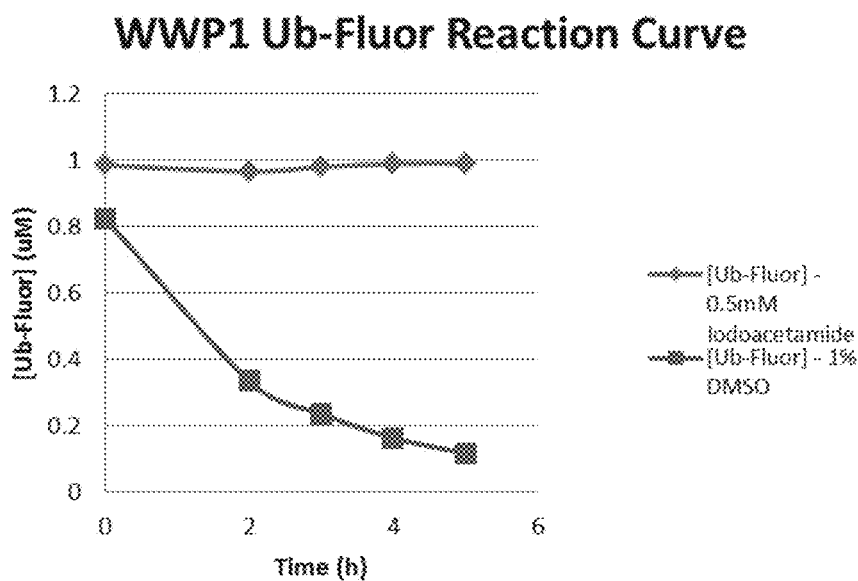

In particular, 0.1 μM WWP1 was added to 1 μM UbiFlu in 150 mM NaCl, 6 μM Tween-20, 50 mM HEPES pH 7.5 and incubated at 27° C. The plate was read at 0, 2, 3, 4 and 5 hours. Data were plotted either as mP vs. time (FIG. 42A) or [UbiFlu] remaining vs. time (FIG. 42B).

Figure 43A:
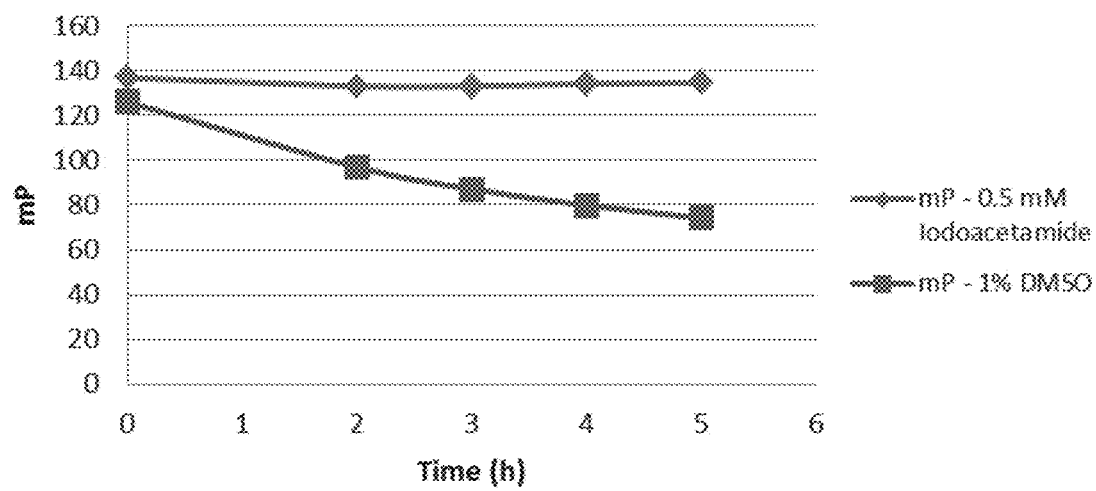
FIG. 43A-43B shows the use of UbiFlu with phosporylated pParkin E3 ligase. Data were plotted either as mP vs. time (FIG. 43A) or [UbiFlu] remaining vs. time (FIG. 43B).
Figure 43B:
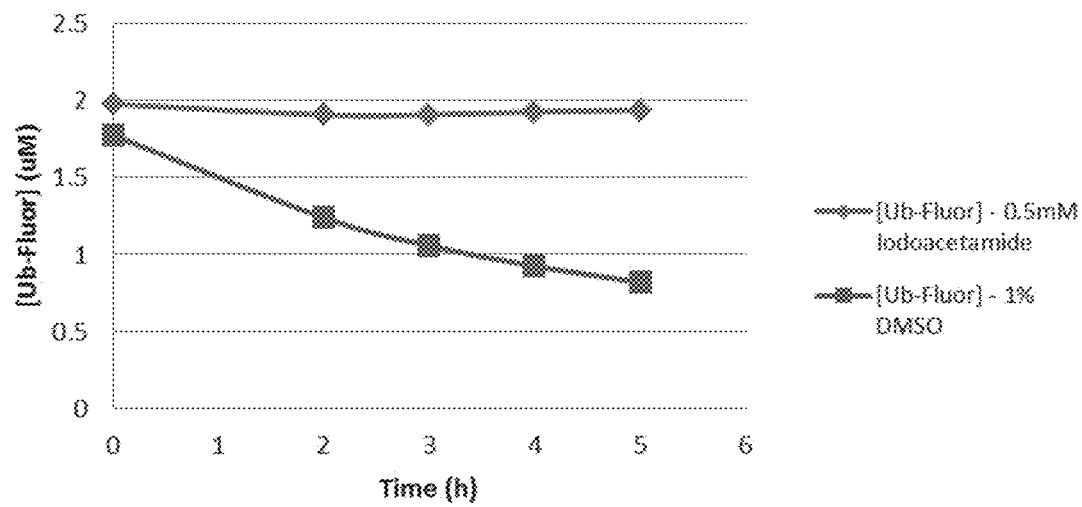

Further, 0.2 μM pParkin (S65 phosphorylated) was added to 2 μM UbiFlu in 150 mM NaCl, 6 μM Tween-20, 50 mM HEPES pH 7.5 and incubated at 27° C. The plate was read at 0, 2, 3, 4, and 5 hours. Data were plotted either as mP vs. time (FIG. 42A) or [Ub-Flu] remaining vs. time (FIG. 43B).

Figure 44A:
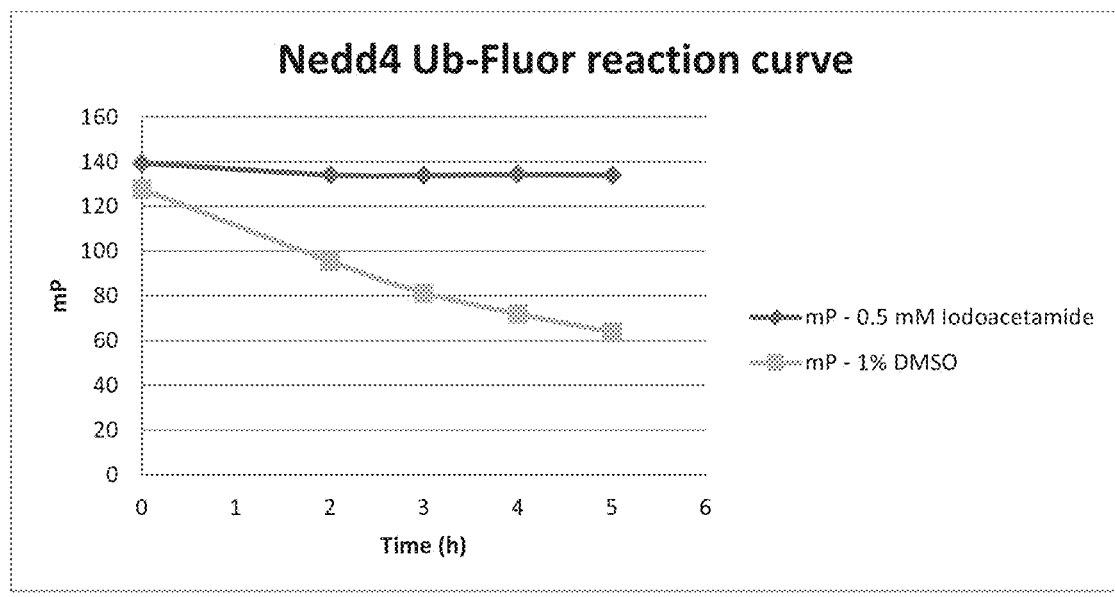
FIG. 44A-44B shows the use of UbiFlu with Nedd4-1 E3 ligase. Data were plotted either as MP vs. time (FIG. 44A) or [UbiFlu] remaining vs. time (FIG. 44B).
Figure 44B:
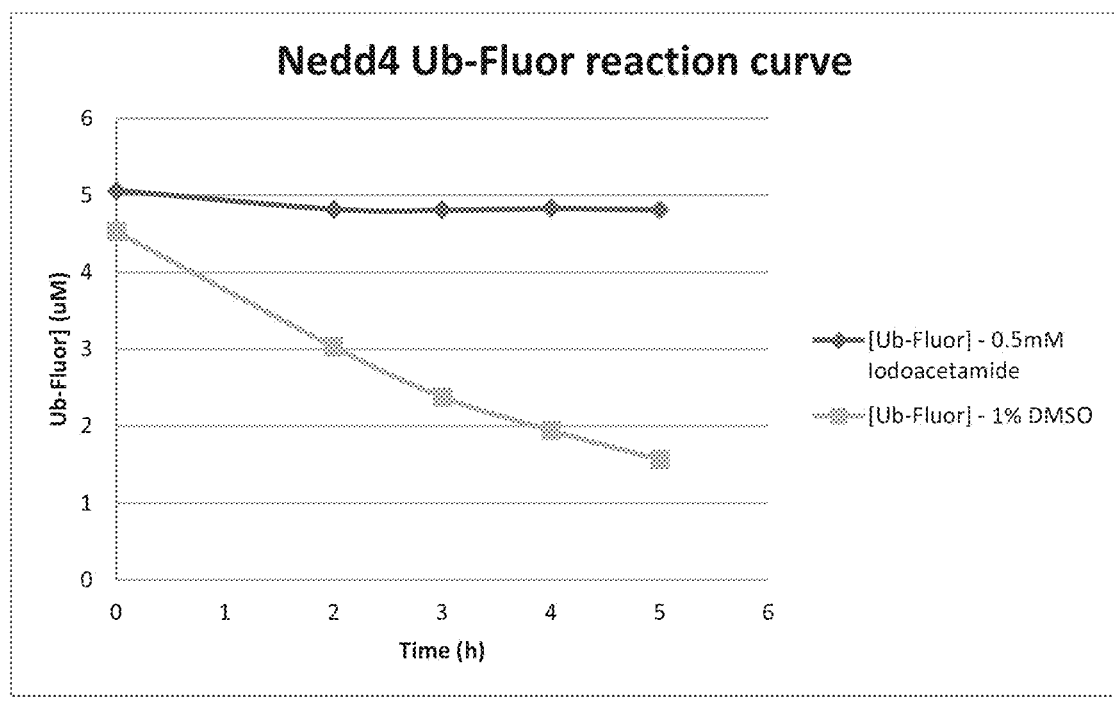
Figure 45:
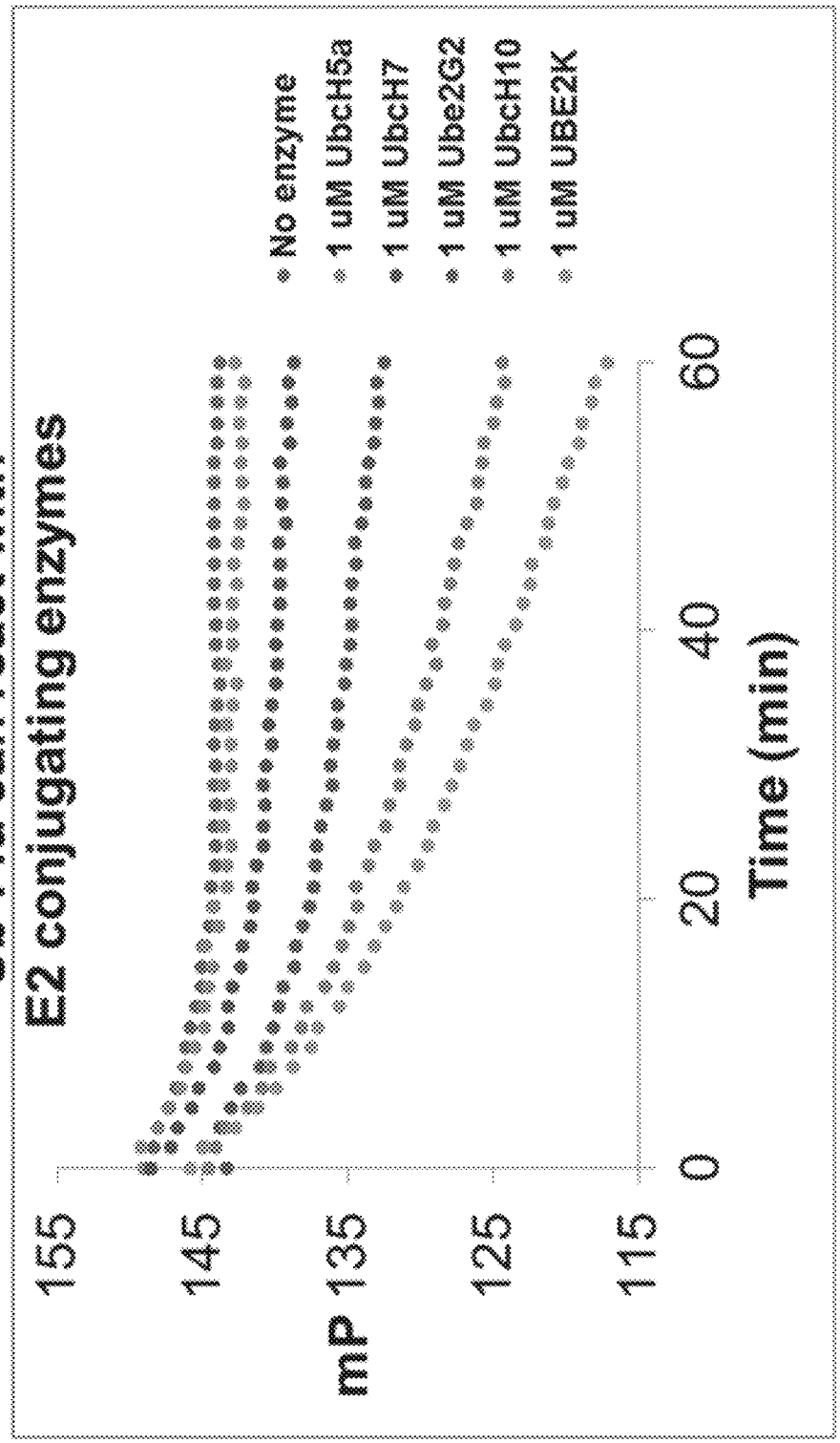
FIG. 45 is a plot showing that UbFluor reacts with ubiquitin conjugating E2 enzymes that comprise catalytic cysteines. Data are shown as polarization (mP) versus time for five E2 enzymes, from top to bottom on the plot, respectively: UbcH5a, UbcH7, Ube2G2, UbcH10, UBE2K.

Finally, 0.5 μM Nedd4 was added to 5 μM UbiFlu in 150 mM NaCl, 6 μM Tween-20, 50 mM HEPES pH 7.5 and incubated at 27° C. The plate was read at 0, 2, 3, 4, and 5 hours. Data were plotted either as mP vs. time (FIG. 44A) or [UbiFlu] remaining vs. time (FIG. 44B).

Example 14

Ub-Flu Reacts With E2 Conjugating Enzymes

During the development of embodiments of the technology provided herein, experiments were conducted that indicated that UbFluor reacts with ubiquitin conjugating E2 enzymes. In these experiments, UbiFluor (6.0 μM) was mixed with enzyme (1.0 μM) in 20 mM HEPES 7.5, 50 mM NaCl and then immediately added to a 384 well plate (70 μL). Fluorescence polarization was observed with the Synergy 4 plate reader every 90 seconds. Thus, these data indicated that UbFluor finds use to detect the enzymatic activity of E2 enzymes. Alternatively, UbFluor finds use to detect enzymatic turnover of E2 enzymes in the presence of E3 ligases that are known to activate thioester for the reaction with the lysine of the substrate protein. The use of UbFluor to assay E3 and E2 enzymes thus finds use in various disease applications.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method of screening for modulators of E3 ligase activity, the method comprising:
   a) providing a test composition comprising an E3 ligase, a ubiquitin C-terminal thioester fluorophore, and a molecule to test for the ability to modulate the activity of the E3 ligase;
   b) monitoring the fluorescence of the fluorophore in the test composition;
   c) comparing the fluorescence of the fluorophore in the test composition to the fluorescence of a control composition comprising the E3 ligase and the ubiquitin C-terminal thioester fluorophore, but not comprising the molecule to test; and
   d) identifying the molecule to test as a molecule that modulates the activity of E3 ligase when the fluorescence of the fluorophore in the test composition is different than the fluorescence of the fluorophore in the control composition.

2. The method of claim 1, wherein the E3 ligase is NEDD4, NEDD4L, ITCH, WWP1, WWP2, SMURF1, SMURF2, NEDL1, NEDL2, E6AP, HECTD2, KIAA0614, TRIP12, G2E3, EDD, HACE1, HECTD1, UBE3B, UBE3C, KIAA0317, HUWE1, HECTD3, HERC1, HERC2, HERC3, HERC4, HERC5, HERC6, SopA, NleL, ARIH1, ARIH2, CUL9, ANKIB1, PARK2, RNF144A, RNF144B, RBCK1, RNF19A, RNF19B, RNF31, RNF216, RNF14, RNF217, or a NEL E3.

3. The method of claim 1, wherein the E3 ligase is associated with a disease.

4. The method of claim 3, wherein the disease is a hypertensive disorder, a neurodegenerative disease, a cancer, an autoimmune disorder, a development disorder, a viral infection, a metabolic disorder, or a bacterial infection.

5. The method of claim 1, wherein the ubiquitin C-terminal thioester fluorophore comprises a ubiquitin covalently attached to a linker and a linker covalently attached to the fluorophore.

6. The method of claim 1, wherein monitoring the fluorescence of the fluorophore comprises monitoring fluorescence polarization.

7. The method of claim 1, further comprising calculating a kinetic parameter of E3 ligase activity.

8. The method of claim 1, wherein the composition further comprises a small molecule thiol.

9. The method of claim 1, wherein a plurality of molecules are tested for the ability to modulate the activity of the E3 ligase in a high-throughput screening assay.

10. A method of measuring the activity of an E3 and/or an E2 enzyme, the method comprising:
    a) providing a test composition comprising an E3 and/or an E2 enzyme and a ubiquitin C-terminal thioester fluorophore;
    b) monitoring the fluorescence of the fluorophore in the test composition; and
    c) calculating the activity of the E3 and/or E2 enzyme using the fluorescence of the fluorophore as a function of time.

11. The method of claim 10, wherein monitoring the fluorescence of the fluorophore comprises monitoring fluorescence polarization.

12. The method of claim 10, wherein the composition further comprises a small molecule thiol.

13. The method of claim 10, wherein the ubiquitin C-terminal thioester fluorophore comprises a ubiquitin covalently attached to a linker and a linker covalently attached to the fluorophore.

14. The method of claim 10, wherein fluorescence is monitored in real-time to measure reaction kinetics.

* * * * *